US 6,683,093 B2

(12) United States Patent
Barta et al.

(10) Patent No.: US 6,683,093 B2
(45) Date of Patent: *Jan. 27, 2004

(54) AROMATIC SULFONE HYDROXAMIC ACIDS AND THEIR USE AS PROTEASE INHIBITORS

(75) Inventors: Thomas E. Barta, Evanston, IL (US); Daniel P. Becker, Glenview, IL (US); Louis J. Bedell, Mt. Prospect, IL (US); Terri L. Boehm, Ballwin, MO (US); Jeffery N. Carroll, Collinsville, IL (US); Gary A. DeCrescenzo, St. Charles, MO (US); Yvette M. Fobian, Labadie, MO (US); John N. Freskos, Clayton, MO (US); Daniel P. Getman, Chesterfield, MO (US); Joseph J. McDonald, Ballwin, MO (US); Madeleine H. Li, Vernon Hills, IL (US); Susan L. Hockerman, Chicago, IL (US); Carol Pearcy Howard, Fenton, MO (US); Steve A. Kolodziej, Ballwin, MO (US); Deborah A. Mischke, Defiance, MO (US); Joseph G. Rico, Ballwin, MO (US); Nathan W. Stehle, Ballwin, MO (US); Michael B. Tollefson, O'Fallon, MO (US); William F. Vernier, St. Louis, MO (US); Clara I. Villamil, Glenview, IL (US); Darren J. Kassab, Wildwood, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/989,943

(22) Filed: Nov. 21, 2001

(65) Prior Publication Data

US 2003/0073718 A1 Apr. 17, 2003

Related U.S. Application Data

(63) Continuation-in-part of application No. 09/570,731, filed on May 12, 2000.

(51) Int. Cl.[7] .................... A61K 31/445; C07D 401/12
(52) U.S. Cl. .................. 514/316; 514/317; 514/324; 514/330; 544/147; 546/186; 546/187; 546/202
(58) Field of Search ................. 514/316, 317, 514/324, 330; 544/147; 546/186, 187, 202

(56) References Cited

U.S. PATENT DOCUMENTS

| | | | | |
|---|---|---|---|---|
| 4,595,700 | A | 6/1986 | Donald et al. | 514/616 |
| 5,932,595 | A | 8/1999 | Bender et al. | 514/317 |
| 6,013,649 | A | 1/2000 | Freskos et al. | 514/237.8 |
| 6,300,514 | B1 | 10/2001 | Takahashi et al. | 560/17 |
| 6,541,489 | B1 * | 4/2003 | Barta et al. | 514/330 |

FOREIGN PATENT DOCUMENTS

| | | | |
|---|---|---|---|
| EP | 0 266 182 | 5/1988 | ......... C07D/307/32 |
| EP | 0 606 046 | 7/1994 | ......... C07D/213/42 |
| EP | 0 780 386 | 6/1997 | ......... C07D/309/08 |
| EP | 0 930 067 | 7/1999 | .......... A61K/31/40 |
| EP | 1 081 137 | 3/2001 | ......... C07D/211/96 |
| JP | 4-338331 | 11/1992 | ......... A61K/31/365 |
| WO | WO 90/05719 | 5/1990 | ......... C07C/323/62 |
| WO | WO 93/20047 | 10/1993 | ......... C07C/317/44 |
| WO | WO 94/02466 | 2/1994 | ......... C07D/221/14 |
| WO | WO 94/24140 | 10/1994 | .......... C07H/13/04 |
| WO | WO 95/09841 | 4/1995 | ......... C07C/323/60 |
| WO | WO 95/13289 | 5/1995 | ............ C07K/5/062 |
| WO | WO 95/29892 | 11/1995 | ....... C07D/207/327 |
| WO | WO 96/06074 | 2/1996 | ......... C07C/259/06 |
| WO | WO 96/11209 | 4/1996 | ............ C07K/5/06 |
| WO | WO 97/20824 | 6/1997 | ......... C07D/241/04 |
| WO | WO 97/24117 | 7/1997 | .......... A61K/31/19 |
| WO | WO 98/37877 | 9/1998 | .......... A61K/31/16 |
| WO | WO 98/38163 | 9/1998 | ......... C07C/323/60 |
| WO | WO 99/09000 | 2/1999 | ......... C07C/235/00 |
| WO | WO 99/25687 | 5/1999 | ......... C07D/211/66 |
| WO | WO 99/42436 | 8/1999 | ......... C07C/239/14 |
| WO | WO 00/46221 | 8/2000 | ......... C07D/405/12 |
| WO | WO 00/50396 | 8/2000 | ......... C07D/211/66 |
| WO | WO 00/59874 | 10/2000 | ......... C07C/259/06 |
| WO | WO 00/69821 | 11/2000 | ......... C07D/211/66 |

OTHER PUBLICATIONS

U.S. patent application Ser. No. 10/142,737, Barta et al., filed May 10, 2002.

Brown, "Synthetic Inhibitors of Matrix Metalloproteinases"; *Matrix Metalloproteinases*, pp. 243–261.

Dack et al. "Preparation of N–hydroxytetrahydro . . . " CA 131:44740 (1999).

Denis et al., *Invest. New Drugs*, 15A, 175–185 (1997).

Gearing et al. *Nature*, 376, 555–557 (1994).

(List continued on next page.)

*Primary Examiner*—Ceila Chang
(74) *Attorney, Agent, or Firm*—Harness, Dickey & Pierce, P.L.C.

(57) ABSTRACT

This invention is directed to aromatic sulfone hydroxamates (also known as aromatic sulfone hydroxamic acids) and salts thereof that, inter alia, tend to inhibit matrix metalloproteinase (also known as matrix metalloprotease or MMP) activity and/or aggrecanase activity. This invention also is directed to a treatment method that comprises administering such a compound or salt in an MMP-inhibiting and/or aggrecanase-inhibiting effective amount to an animal, particularly a mammal having (or disposed to having) a pathological condition associated with MMP activity and/or aggrecanase activity.

93 Claims, No Drawings

OTHER PUBLICATIONS

Kenyon, BM, et al., A Model of Angiogenesis in the Mouse Cornea; *Investigative Ophthalmology & Visual Science*, vol. 37, No. 8 (Jul. 1996).

Knight et al., *FEBS Lett*. 296(3):263 (1992).

Luckow et al., *J. Virol.*, 67:4566–4579 (1993).

McClure et al. "Matrix metalloprotease . . . " CA 131:125454 (1999).

McGeehan et al., *Nature* 370, 558–561 (1994).

Mitchell et al., *J. Clin. Invsest.*, 97(3) 761–768 (1996).

Rasmussen et al., *Pharmacol. Ther.*, 75(l): 69–75 (1997).

Reboul et al., *J. Clin Invest.*, 97(9), 2011–2019 (1996).

Schwartz et al., *Progr. Med. Chem.*, 29:271–334 (1992).

Tang, *ADAMTS*: a novel family of extracellular matrix proteases, *The International Journal of Biochemistry & Cell Biology 33* (2001) pp. 33–44.

Woessner, "The Matrix Metalloproteinase Family", *Matrix Metalloproteinases*, (1999) p. 1–14.

* cited by examiner

AROMATIC SULFONE HYDROXAMIC ACIDS AND THEIR USE AS PROTEASE INHIBITORS

CROSS-REFERENCE TO RELATED PATENT APPLICATIONS

This patent claims priority as a continuation-in-part to U.S. patent application Ser. No. 09/570,731 (filed May 12, 2000), which, in turn, claims priority to U.S. patent application Ser. Nos. 09/311,837 (filed May 14, 1999) and 09/256,948 (filed Feb. 24, 1999), which, in turn, claim priority to U.S. patent application Ser. Nos. 09/191,129 (filed Nov. 13, 1998), 09/186,410 (filed Nov. 5, 1998), 60/066,007 (filed Nov. 14, 1997), 60/095,347 (filed Aug. 4, 1998), 60/095,501 (filed Aug. 6, 1998), and 60/101,080 (filed Sep. 18, 1998). The entire texts of the above-referenced patent applications are incorporated by reference into this patent.

FIELD OF THE INVENTION

This invention is directed generally to proteinase (also known as "protease") inhibitors, and, more particularly, to aromatic sulfone hydroxamate compounds (also known as "aromatic sulfone hydroxamic acid compounds") and salts thereof (particularly pharmaceutically acceptable salts) that, inter alia, inhibit matrix metalloproteinase (also known as "matrix metalloprotease" or "MMP") and/or aggrecanase activity. This invention also is directed to pharmaceutical compositions of such compounds and salts, and methods of using such compounds and salts to prevent or treat conditions associated with MMP and/or aggrecanase activity, particularly pathological conditions.

BACKGROUND OF THE INVENTION

Connective tissue is a required component of all mammals. It provides rigidity, differentiation, attachments, and, in some cases, elasticity. Connective tissue components include, for example, collagen, elastin, proteoglycans, fibronectin, and laminin. These biochemicals make up (or are components of) structures, such as skin, bone, teeth, tendon, cartilage, basement membrane, blood vessels, cornea, and vitreous humor.

Under normal conditions, connective tissue turnover and/or repair processes are in equilibrium with connective tissue production. Degradation of connective tissue is carried out by the action of proteinases released from resident tissue cells and/or invading inflammatory or tumor cells.

Matrix metalloproteinases, a family of zinc-dependent proteinases, make up a major class of enzymes involved in degrading connective tissue. Matrix metalloproteinases are divided into classes, with some members having several different names in common use. Examples are: MMP-1 (also known as collagenase 1, fibroblast collagenase, or EC 3.4.24.3); MMP-2 (also known as gelatinase A, 72 kDa gelatinase, basement membrane collagenase, or EC 3.4.24.24), MMP-3 (also known as stromelysin 1 or EC 3.4.24.17), proteoglycanase, MMP-7 (also known as matrilysin), MMP-8 (also known as collagenase II, neutrophil collagenase, or EC 3.4.24.34), MMP-9 (also known as gelatinase B, 92 kDa gelatinase, or EC 3.4.24.35), MMP-10 (also known as stromelysin 2 or EC 3.4.24.22), MMP-1 I (also known as stromelysin 3), MMP-12 (also known as metalloelastase, human macrophage elastase or HME), MMP-13 (also known as collagenase 111), and MMP-14 (also known as MT1-MMP or membrane MMP). See, generally, Woessner, J. F., "The Matrix Metalloprotease Family" in *Matrix Metalloproteinases*, pp. 1–14 (Edited by Parks, W. C. & Mecham, R. P., Academic Press, San Diego, Calif. 1998).

Excessive breakdown of connective tissue by MMPs is a feature of many pathological conditions. Inhibition of MMPs therefore provides a control mechanism for tissue decomposition to prevent and/or treat these pathological conditions. Such pathological conditions generally include, for example, tissue destruction, fibrotic diseases, pathological matrix weakening, defective injury repair, cardiovascular diseases, pulmonary diseases, kidney diseases, liver diseases, and diseases of the central nervous system. Specific examples of such conditions include, for example, rheumatoid arthritis, osteoarthritis, septic arthritis, multiple sclerosis, a decubitis ulcer, corneal ulceration, epidermal ulceration, gastric ulceration, tumor metastasis, tumor invasion, tumor angiogenesis, periodontal disease, liver cirrhosis, fibrotic lung disease, emphysema, otosclerosis, atherosclerosis, proteinuria, coronary thrombosis, dilated cardiomyopathy, congestive heart failure, aortic aneurysm, epidermolysis bullosa, bone disease, Alzheimer's disease, and defective injury repair (e.g., weak repairs, adhesions such as post-surgical adhesions, and scarring).

Matrix metalloproteinases also are involved in the biosynthesis of tumor necrosis factors (TNFs). Tumor necrosis factors are implicated in many pathological conditions. TNF-$\alpha$, for example, is a cytokine that is presently thought to be produced initially as a 28 kD cell-associated molecule. It is released as an active, 17 kD form that can mediate a large number of deleterious effects in vitro and in vivo. TNF-$\alpha$ can cause and/or contribute to the effects of inflammation (e.g., rheumatoid arthritis), autoimmune disease, graft rejection, multiple sclerosis, fibrotic diseases, cancer, infectious diseases (e.g., malaria, mycobacterial infection, meningitis, etc.), fever, psoriasis, cardiovascular diseases (e.g., post-ischemic reperfusion injury and congestive heart failure), pulmonary diseases, hemorrhage, coagulation, hyperoxic alveolar injury, radiation damage, and acute phase responses like those seen with infections and sepsis and during shock (e.g., septic shock and hemodynamic shock). Chronic release of active TNF-$\alpha$ can cause cachexia and anorexia. TNF-$\alpha$ also can be lethal.

Inhibiting TNF (and related compounds) production and action is an important clinical disease treatment. Matrix metalloproteinase inhibition is one mechanism that can be used. MMP (e.g., collagenase, stromelysin, and gelatinase) inhibitors, for example, have been reported to inhibit TNF-$\alpha$ release. See, e.g., Gearing et al. *Nature* 376, 555–557 (1994). See also, McGeehan et al. See also, *Nature* 376, 558–561 (1994). MMP inhibitors also have been reported to inhibit TNF-$\alpha$ convertase, a metalloproteinase involved in forming active TNF-$\alpha$. See, e.g., WIPO Int'l Pub. No. WO 94/24140. See also, WIPO Int'l Pub. No. WO 94/02466. See also, WIPO Int'l Pub. No. WO 97/20824.

Matrix metalloproteinases also are involved in other biochemical processes in mammals. These include control of ovulation, post-partum uterine involution, possibly implantation, cleavage of APP ($\beta$-amyloid precursor protein) to the ainyloid plaque, and inactivation of ($\alpha_1$-protease inhibitor ($\alpha_1$-PI). Inhibiting MMPs therefore may be a mechanism that may be used to control of fertility. In addition, increasing and maintaining the levels of an endogenous or administered serine protease inhibitor (e.g., $\alpha_1$-PI) supports the treatment and prevention of pathological conditions such as emphysema, pulmonary diseases, inflammatory diseases, and diseases of aging (e.g., loss of skin or organ stretch and resiliency).

Numerous metalloproteinase inhibitors are known. See, generally, Brown, P. D., "Synthetic Inhibitors of Matrix Metalloproteinases," in *Matrix Metalloproteinases*, pp. 243–61 (Edited by Parks, W. C. & Mecham, R. P., Academic Press, San Diego, Calif. 1998).

Metalloproteinase inhibitors include, for example, natural biochemicals, such as tissue inhibitor of metalloproteinase (TIMP), α2-macroglobulin, and their analogs and derivatives. These are high-molecular-weight protein molecules that form inactive complexes with metalloproteinases.

A number of smaller peptide-like compounds also have been reported to inhibit metalloproteinases. Mercaptoamide peptidyl derivatives, for example, have been reported to inhibit angiotensin coniierting enzyme (also known as ACE) in vitro and in vivo. ACE aids in the production of angiotensin II, a potent pressor substance in mammals. Inhibiting ACE leads to lowering of blood pressure.

A wide variety of thiol compounds have been reported to inhibit MMPs. See, e.g., W095/12389. See also, W096/11209. See also, U.S. Pat. No. 4,595,700. See also, U.S. Pat. No. 6.013,649.

A wide variety of hydroxamate compounds also have been reported to inhibit MMPs. Such compounds reportedly include hydroxamates having a carbon backbone. See, e.g., WIPO Int'l Pub. No. WO 95/29892. See also, WIPO Int'l Pub. No. WO 97/24117. See also, WIPO Int'l Pub. No. WO 97/49679. See also, European Patent No. EP 0 780 386. Such compounds also reportedly include hydroxamates having peptidyl backbones or peptidomimetic backbones. See, e.g., WIPO Int'l Pub. No. WO 90/05719. See also, WIPO Int'l Pub. No. WO 93/20047. See also, WIPO Int'l Pub. No. WO 95/09841. See also, WIPO Int'l Pub. No. WO 96/06074. See also, Schwartz et al., *Progr. Med. Chem.*, 29:271–334(1992). See also, Rasmussen et al., *Pharmacol. Ther.*, 75(1): 69–75 (1997). See also, Denis et al.,*Invest New Drugs*, 15(3): 175–185 (1997). Sulfamato hydroxamates have additionally been reported to inhibit MMPs. See, WIPO Int'l Pub. No. WO 00/46221. And various aromatic sulfone hydroxamates have been reported to inhibit MMPs. See, WIPO Int'l Pub. No. WO 99/25687. See also, WIPO Int'l Pub. No. WO 00/50396. See also, WIPO Int'l Pub. No. WO 00/69821.

It is often advantageous for an MMP inhibitor drug to target a certain MMP(s) over another MMP(s). For example, it is typically preferred to inhibit MMP-2, MMP-3, MMP-9, and/or MMP-13 (particularly MMP-13) when treating and/or preventing cancer, inhibiting of metastasis, and inhibiting angiogenesis. It also is typically preferred to inhibit MMP-13 when preventing and/or treating osteoarthritis. See, e.g., Mitchell et al.,*J Clin. Invest.*, 97:761–768 (1996). See also, Reboul et al., *J Clin. Invest.*, 97:2011–2019 (1996). Normally, however, it is preferred to use a drug that has little or no inhibitory effect on MMP-1 and MMP-14. This preference stems from the fact that both MMP-1 and MMP-14 are involved in several homeostatic processes, and inhibition of MMP-1 and/or MMP-14 consequently tends to interfere with such processes.

Many known MMP inhibitors exhibit the same or similar inhibitory effects against each of the MMPs. For example, batimastat (a peptidomimetic hydroxamate) has been reported to exhibit $IC_{50}$ values of from about 1 to about 20 nM against each of MMP-1, MMP-2, MMP-3, MMP-7, and MMP-9. Marimastat (another peptidomimetic hydroxamate) has been reported to be another broad-spectrum MMP inhibitor with an enzyme inhibitory spectrum similar to batimastat, except that Marimastat reportedly exhibited an $IC_{50}$ value against MMP-3 of 230 nM. See Rasmussen et al., *Pharmacol. Ther.*, 75(1): 69–75 (1997).

Meta analysis of data from Phase I/II studies using Marimastat in patients with advanced, rapidly progressive, treatment-refractory solid tumor cancers (colorectal, pancreatic, ovarian, and prostate) indicated a dose-related reduction in the rise of cancer-specific antigens used as surrogate markers for biological activity. Although Marimastat exhibited some measure of efficacy via these markers, toxic side effects reportedly were observed. The most common drug-related toxicity of Marimastat in those clinical trials was musculoskeletal pain and stiffness, often commencing in the small joints in the hands, and then spreading to the arms and shoulder. A short dosing holiday of 1–3 weeks followed by dosage reduction reportedly permits treatment to continue. See Rasmussen et al., *Pharmacol Ther.*, 75(1): 69–75 (1997). It is thought that the lack of specificity of inhibitory effect among the MMPs may be the cause of that effect.

Another enzyme implicated in pathological conditions associated with excessive degradation of connective tissue is aggrecanase, particularly aggrecanase-1 (also known as ADAMTS-4). Specifically, articular cartilage contains large amounts of the proteoglycan aggrecan. Proteoglycan aggrecan provides mechanical properties that help articular cartilage in withstanding compressive deformation during joint articulation. The loss of aggrecan fragments and their release into synovial fluid caused by proteolytic cleavages is a central pathophysiological event in osteoarthritis and rheumatoid arthritis. It has been reported that two major cleavage sites exist in the proteolytically sensitive interglobular domains at the N-terminal region of the aggrecan core protein. One of those sites has been reported to be cleaved by several matrix metalloproteases. The other site, however, has been reported to be cleaved by aggrecanase-1. Thus, inhibiting excessive aggrecanase activity provides a method for preventing or treating inflammatory conditions. See generally, Tang, B. L., "ADAMTS: A Novel Family of Extracellular Matrix Proteases," *Int'l Journal of Biochemistry & Cell Biology*, 33, pp. 33–44 (2001). Such diseases reportedly include, for example, osteoarthritis, rheumatoid arthritis, joint injury, reactive arthritis, acute pyrophosphate arthritis, and psoriatic arthritis. See, e.g., European Patent Application Publ. No. EP 1 081 137 A1.

In addition to inflammatory conditions, there also is evidence that inhibiting aggrecanase may be used for preventing or treating cancer. For example, excessive levels of aggrecanase-1 reportedly have been observed with a ghoma cell line. It also has been postulated that the enzymatic nature of aggrecanase and its similarities with the MMPs would support tumor invasion, metastasis, and angiogenesis. See Tang, *Int'l Journal of Biochemistry & Cell Biology*, 33, pp. 33–44 (2001).

Various hydroxamate compounds have been reported to inhibit aggrecanase-1. Such compounds include, for example, those described in European Patent Application Publ. No. EP 1 081 137 A1. Such compounds also include, for example, those described in WIPO PCT Int'l Publ. No. WO 00/09000. Such compounds further include, for example, those described in WIPO PCT Int'l Publ. No. WO 00/59874.

In view of the importance of hydroxamate compounds and salts thereof in the prevention or treatment of several MMP- and/or aggrecanase-related pathological conditions and the lack of enzyme specificity exhibited by at least some of the hydroxamates that have been in clinical trials, there continues to be a need for hydroxamates having greater enzyme inhibition specificity (preferably toward MMP-2, MMP-9,MMP-13, and/or aggrecanase, and particularly toward MMP-13 and/or aggrecanase), while exhibiting little or no inhibition of MMP activity essential to normal bodily function (e.g., tissue turnover and repair). The following disclosure describes hydroxamate compounds and salts thereof that tend to exhibit such desirable activities.

SUMMARY OF THE INVENTION

This invention is directed to compounds that inhibit MMP (particularly MMP-2, MMP-9, and/or MMP-13) and/or aggrecanase activity, while generally exhibiting relatively little or no inhibition against MMP activity essential to normal bodily function (particularly MMP-1 and MMP-14 activity). This invention also is directed to a method for inhibiting MMP and/or aggrecanase activity, particularly pathological activity. Such a method is particularly suitable to be used with mammals, such as humans, other primates (e.g., monkeys, chimpanzees. etc.), companion animals (e.g., dogs, cats, horses. etc.), farm animals (e.g., goats, sheep, pigs, cattle, etc.), laboratory animals (e.g., mice, rats, etc.), and wild and zoo animals (e.g., wolves, bears, deer, etc.).

Briefly, therefore, the invention is directed in part to a compound or salt thereof The compound has a structure corresponding to Formula X:

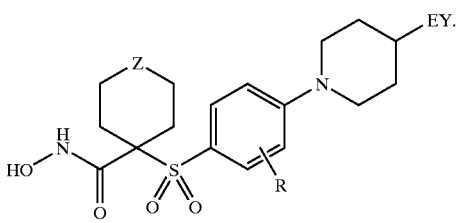

The variables Z, R, E, and Y are described in more detail below.

The present invention also is directed to treatment methods that comprise administering a compound described above (or pharmaceutically-acceptable salt thereof) in an effective amount to a host mammal having a condition associated with pathological metalloprotease and/or aggrecanase activity. A contemplated compound or salt thereof tends to exhibit, for example, inhibitory activity of one or more matrix metalloprotease (MMP) enzymes (e.g., MMP-2, MMP-9 and MMP-13), while exhibiting substantially less inhibition of MMP-1 and/or MMP-14. By "substantially less" it is meant that a contemplated compound exhibits an $IC_{50}$ value ratio against one or more of MMP-2, MMP-9, or MMP-13 as compared to its $IC_{50}$ value against MMP-1 and/or MMp-14 (e.g., $IC_{50}$ MMP-13:$IC_{50}$ MMP-1) that is less than about 1:10, preferably less than about 1:100, and most preferably less than about 1:1000 in the in vitro inhibition assay described in the Example section below.

In one embodiment, the process comprises administering an above-described compound or pharmaceutically acceptable salt thereof to the host animal in an amount effective to prevent or treat the condition. Such a condition may be, for example, tissue destruction, a fibrotic disease, pathological matrix weakening, defective injury repair, a cardiovascular disease, a pulmonary disease, a kidney disease, and a central nervous system disease. Specific examples of such conditions include osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermolysis bullosa, aortic aneurysm, weak injury repair, an adhesion, scarring, congestive heart failure, coronary thrombosis, emphysema, proteinuria, and Alzheimer's disease.

In another embodiment, the prevention or treatment method comprises administering an above-described compound or pharmaceutically acceptable salt thereof to the host animal in an amount effective to inhibit matrix metalloprotease-2, matrix metalloprotease-9, and/or matrix metalloprotease-13 activity.

In another embodiment, the prevention or treatment method comprises administering an above-described compound or pharmaceutically acceptable salt thereof to the host animal in an amount effective to prevent or treat a condition associated with TNF-α convertase activity. Examples of such a condition include inflammation, a pulmonary disease, a cardiovascular disease, an autoimmune disease, graft rejection, a fibrotic disease, cancer, an infectious disease, fever, psoriasis, hemorrhage, coagulation, radiation damage, acute-phase responses of shock and sepsis, anorexia, and cachexia.

In another embodiment, the prevention or treatment method comprises administering an above-described compound or pharmaceutically acceptable salt thereof to the host animal in an amount effective to prevent or treat a condition associated with aggrecanase activity. Such a condition may be, for example, an inflammatory disease or cancer.

This invention additionally is directed, in part, to pharmaceutical compositions comprising the above-described compounds or pharmaceutically acceptable salts thereof, and the use of those compositions in the above-described prevention or treatment processes.

This invention further is directed, in part, to the use of an above-described compound or pharmaceutically acceptable salt thereof for production of a medicament for use in the treatment of a condition related to MMP activity. As noted above, such a condition may be, for example, tissue destruction, a fibrotic disease, pathological matrix weakening, defective injury repair, a cardiovascular disease, a pulmonary disease, a kidney disease, and a central nervous system disease.

Further benefits of Applicants' invention will be apparent to one skilled in the art reading this patent.

DETAILED DESCRIPTION OF THE PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating the preferred embodiments of this invention, are intended for purposes of illustration only. This invention, therefore, is not limited to the preferred embodiments described in this patent, and may be variously modified.

A. Compounds of this Invention

In accordance with this invention, Applicants have found that certain aromatic sulfone hydroxamates tend to be effective toward inhibiting MMPs, particularly those associated with excessive (or otherwise pathological) breakdown of connective tissue. Specifically, Applicants have found that these hydroxamates tend to be effective for inhibiting MMP-2 MMP-9, and/or MMP-13, which can be particularly destructive to tissue if present or generated in abnormally excessive quantities or concentrations. Applicants also have discovered that many of these hydroxamates tend to be effective toward inhibiting pathological aggrecanase activity. Applicants have further discovered that these hydroxamates tend to be selective toward inhibiting aggrecanase and/or MMPs associated with pathological condition conditions, and tend to avoid excessive inhibition of MMPs (particularly MMP-1 and MMP-14) essential to normal bodily function (e.g., tissue turnover and repair). Applicants have found, for example, that these hydroxamates tend to be particularly active toward inhibiting MMP-2, MMP-9, MMP-13, and/or aggrecanase activity in vitro assays that are generally predictive of in vivo activity, while exhibiting minimal inhibition toward MMP-1 and/or MMP-14 in such assays. Examples of such in vitro assays are discussed in the example section below. Compounds (or salts) that are particularly useful as selective MMP inhibitors exhibit, for example, an in vitro $IC_{50}$ value against one or more of MMP-2, MMP-9, and MMP-13 that is no greater than about 0.1 times the $IC_{50}$ value against MMP-1 and/or MMP-14, more preferably no greater than about 0.01 times the $IC_{50}$ value against MMP-1 and/or MMP-14, and even more preferably 0.001 times the $IC_{50}$ value against MMP-1 and/or MMP-14.

Without being bound by theory, the advantages of the selectivity of a contemplated compound can be appreciated by considering the roles of the various MMP and aggrecanase enzymes. For example, inhibition of MMP-1 is believed to be undesirable due to the role of MMP-1 as a housekeeping enzyme (i. e., helping to maintain normal connective tissue turnover and repair). Inhibition of MMP-1 can lead to toxicities or side effects such as such as joint or connective tissue deterioration and pain. On the other hand, MMP-13 is believed to be intimately involved in the destruction of joint components in diseases such as osteoarthritis. Thus, potent and selective inhibition of MMP-13 is typically highly desirable because such inhibition can have a positive effect on disease progression in a patient (in addition to having an anti-inflammatory effect).

Another advantage of the compounds and salts of this invention is their tendency to be selective with respect to tumor necrosis factor release and/or tumor necrosis factor receptor release. This provides the physician with another factor to help select the best drug for a particular patient. Without being bound by theory, it is believed that there are multiple factors to this type of selectivity to be considered. The first is that presence of tumor necrosis factor can be desirable for the control of cancer in the organism, so long as TNF is not present in a toxic excess. Thus, uncontrolled inhibition of release of TNF can be counterproductive and actually can be considered an adverse side effect even in cancer patients. In addition, selectivity with respect to inhibition of the release of the tumor necrosis factor receptor can also be desirable. The presence of that receptor can be desirable for maintaining a controlled tumor necrosis level in the mammal by binding excess TNF.

Briefly, therefore, this invention is directed, in part, to a compound or salt thereof (particularly a pharmaceutically acceptable salt thereof). The compound has a structure corresponding to Formula X:

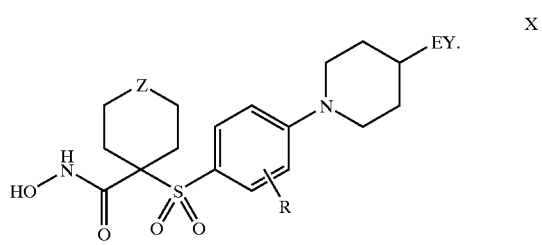

In some preferred embodiments:

Z is —C(O)—, —N($R^6$)—, —O—, —S—, —S(O)—, —S(O)$_2$—, or —N(S(O)$_2R^7$)—. In some particularly preferred embodiments, Z is —O—. In other particularly preferred embodiments, Z is —N($R^6$)—.

$R^6$ is hydrogen, formyl, sulfonic-$C_1$–$C_6$-alkyl, $C_1$–$C_6$-alkoxycarbonyl-$C_1$–$C_6$-alkyl, carboxy-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, carboxy-$C_1$–$C_6$-alkylcarbonyl, $C_1$–$C_6$-alkylcarbonyl-$C_1$–$C_6$-alkylcarbonyl, $C_1$–$C_6$-alkylcarbonyl, $C_1$–$C_6$-alkoxycarbonyl, carboxy, $C_1$–$C_6$-alkylcarbonyl, $R^8R^9$-aminocarbonyl, aryl-$C_1$–$C_6$-alkyl, arylcarbonyl, bis($C_1$–$C_6$-alkoxy-$C_1$–$C_6$-alkyl)-$C_1$–$C_6$-alkyl, $C_1$–$C_6$-alkyl, halo-$C_1$–$C_6$-alkyl, trifluoromethyl-$C_1$–$C_6$-alkyl, perfluoro-$C_1$–$C_6$-alkoxy-$C_1$–$C_6$-alkyl, $C_1$–$C_6$-alkoxy-$C_1$–$C_6$-alkyl, $C_3$–$C_6$-cycloalkyl, heteroarylcarbonyl, heterocyclylcarbonyl, aryl, heterocyclyl, heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, aminocarbonyl, $C_1$–$C_6$-alkylimino($R^{10}$)carbonyl, arylimino($R^{10}$)carbonyl, $C_5$–$C_6$-heterocyclylimino($R^{10}$)carbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkylcarbonyl, hydroxy-$C_1$–$C_6$-alkylcarbonyl, thiol-$C_1$–$C_6$-alkylcarbonyl, $C_3$–$C_6$-alkenyl, $C_3$–$C_6$-alkynyl, aryloxycarbonyl, $R^8R^9$-aminoimino($R^{10}$)methyl, $R^8R^9$-amino-$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfonyl-$C_1$–$C_6$-alkyl, $R^8R^9$-amino-$C_1$–$C_6$-alkylsulfonyl, or $R^8R^9$-amino-$C_1$–$C_6$-alkyl.

In some particularly preferred embodiments, $R^6$ is $C_1$–$C_6$-alkyl, $C_1$–$C_6$-alkoxy-$C_1$–$C_6$-alkyl, $C_3$–$C_6$-cycloalkyl, $C_3$–$C_8$-cycloalkyl-$C_1$–$C_6$-alkyl, $C_1$–$C_6$-alkylsulfonyl, $C_3$–$C_6$-alkenyl, or $C_3$–$C_6$-alkynyl.

$R^7$ is aryl-$C_1$–$C_6$-alkyl, aryl, heteroaryl, heterocyclyl, $C_1$–$C_6$-alkyl, $C_3$–$C_6$-alkynyl, $C_3$–$C_6$-alkenyl, carboxy-$C_1$–$C_6$-alkyl, or hydroxy-$C_1$–$C_6$-alkyl.

$R^8$ and $R^9$ are independently selected from the group consisting of hydrogen, hydroxy, $C_1$–$C_6$-alkyl, $C_1$–$C_6$-alkylcarbonyl, arylcarbonyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocyclyl-$C_1$–$C_6$-alkyl, $C_1$–$C_6$-alkoxy-$C_1$–$C_6$-alkyl, aryl-$C_1$–$C_6$-alkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, carboxy-$C_1$–$C_6$-alkyl, carboxyaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfoxide of any said thio substituents, a sulfone of any said thio substituents, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$- alkyl. Here, the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl. Preferably, no greater than one of $R^8$ and $R^9$ is hydroxy.

Alternatively, $R^8$ and $R^9$, together with the atom to which they are bonded, form a 5- to 8-membered heterocyclic or heteroaryl ring containing up to 2 heteroatoms independently selected from the group consisting of nitrogen, oxygen, and sulfur.

$R^{10}$ is hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocyclyl-$C_1$–$C_6$-alkyl, $C_1$–$C_6$-alkoxy-$C_1$–$C_6$-alkyl, aryl-$C_1$–$C_6$-alkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, carboxy-$C_1$–$C_6$-alkyl, carboxyaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfoxide of any said thio substituents, a sulfone of any said thio substituents, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl. Here, the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl.

E is a bond, —C(O)—, or —S—.

Y is hydrogen, alkyl, alkoxy, haloalkyl, aryl, arylalkyl, cycloalkyl, heteroaryl, hydroxy, aryloxy, arylalkoxy, heteroaryloxy, heteroarylalkyl, perfluoroalkoxy, perfluoroalkylthio, trifluoromethylalkyl, alkenyl, heterocyclyl, cycloalkyl, trifluoromethyl, alkoxycarbonyl, or aminoalkyl. Here, the aryl, heteroaryl, arylalkyl, or heterocyclyl optionally is substituted with up to 2 substituents independently selected from the group consisting of alkylcarbonyl, halo, nitro, arylalkyl, aryl, alkoxy, trifluoroalkyl, trifluoroalkoxy, and amino. The amino, in turn, optionally is substituted with up to 2 substituents independently selected from the group consisting of alkyl and arylalkyl. In some particularly preferred embodiments, Y comprises a cyclic structure, i.e., Y is optionally substituted aryl, arylalkyl, cycloalkyl, heteroaryl, aryloxy, arylalkoxy, heteroaryloxy, heteroarylalkyl, heterocyclyl, or cycloalkyl. In one such embodiment, Y is optionally substituted phenyl. In another such embodiment, Y is optionally substituted phenylmethyl. In still another such embodiment, Y is optionally substituted heteraryl. And in still yet another such embodiment, Y is optionally substituted heteroarylmethyl.

R is hydrogen, cyano, perfluoroalkyl, trifluoromethoxy, trifluoromethylthio, haloalkyl, trifluoromethylalkyl, arylalkoxycarbonyl, aryloxycarbonyl, hydroxy, halo, alkyl, alkoxy, nitro, thiol, hydroxycarbonyl, aryloxy, arylthio, arylalkyl, aryl, arylcarbonylamino, heteroaryloxy, heteroarylthio, heteroarylalkyl, cycloalkyl, heterocylyloxy, heterocylylthio, heterocylylamino, cycloalkyloxy, cycloalkylthio, heteroarylalkoxy, heteroarylalkylthio, arylalkoxy, arylalkylthio, arylalkylamino, heterocylyl, heteroaryl, arylazo, hydroxycarbonylalkoxy, alkoxycarbonylalkoxy, alkylcarbonyl, arylcarbonyl, arylalkylcarbonyl, alkylcarbonyloxy, arylalkylcarbonyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, aminocarbonyl, or aminoalkyl.

The nitrogen of an R amino may be unsubstituted. Alternatively, the amino nitrogen may be substituted with up two substituents that are independently selected from the group consisting of alkyl, aryl, heteroaryl, arylalkyl, cycloalkyl, arylalkoxycarbonyl, alkoxycarbonyl, arylcarbonyl, arylalkylcarbonyl, heteroarylcarbonyl, heteroarylalkylcarbonyl, and alkylcarbonyl. Alternatively, the amino nitrogen optionally may be substituted with two substituents such that the two substituents, together with the amino nitrogen, form a 5- to 8-member heterocyclyl or heteroaryl ring that: (i) contains from zero to two additional heteroatoms that are independently selected from the group consisting of nitrogen, oxygen, and sulfur; and (ii) optionally is substituted with up to two substituents independently selected from the group consisting of aryl, alkyl, heteroaryl, arylalkyl, heteroarylalkyl, hydroxy, alkoxy, alkylcarbonyl, cycloalkyl, heterocylylalkyl, alkoxycarbonyl, hydroxyalkyl, trifluoromethyl, benzofused heterocylylalkyl, hydroxyalkoxyalkyl, arylalkoxycarbonyl, hydroxycarbonyl, aryloxycarbonyl, benzofused heterocylylalkoxy, benzofused cycloalkylcarbonyl, heterocyclylalkylcarbonyl, and cycloalkylcarbonyl.

The nitrogen of an R aminocarbonyl is may be unsubstituted. Alternatively, the aminocarbonyl nitrogen may be the reacted amine of an amino acid. Alternatively, the aminocarbonyl nitrogen may be substituted with up to two substituents independently selected from the group consisting of alkyl, hydroxyalkyl, hydroxyheteroarylalkyl, cycloalkyl, arylalkyl, trifluoromethylalkyl, heterocylylalkyl, benzofused heterocylylalkyl, benzofused cycloalkyl, and N,N-dialkylsubstituted alkylamino-alkyl. Alternatively, the aminocarbonyl nitrogen may be substituted with two substituents such that the two substituents, together with the aminocarbonyl nitrogen, form a 5- to 8-member heterocyclyl or heteroaryl ring that optionally is substituted with up to two substituents independently selected from the group consisting of alkyl, alkoxycarbonyl, nitro, heterocyclylalkyl, hydroxy, hydroxycarbonyl, aryl, arylalkyl, heteroaralkyl, and amino. Here, the amino nitrogen, in turn, optionally is substituted with: (i) two substituents independently selected from the group consisting of alkyl, aryl, and heteroaryl; or (ii) two substituents such that the two substituents, together with the amino nitrogen, form a 5- to 8-member heterocyclyl or heteroaryl ring.

The nitrogen of an R aminoalkyl may be unsubstituted. Alternatively, the aminoalkyl nitrogen may be substituted with up to two substituents independently selected from the group consisting of alkyl, aryl, arylalkyl, cycloalkyl, arylalkoxycarbonyl, alkoxycarbonyl, and alkylcarbonyl. Alternatively, the aminoalkyl nitrogen may be substituted with two substituents such that the two substituents, together with the aminoalkyl nitrogen, form a 5- to 8-member heterocyclyl or heteroaryl ring.

In one particularly preferred embodiment, R is halogen (preferably chloro or fluoro, and even more preferably chloro). In another particularly preferred embodiment, R is hydrogen so that the compound corresponds in structure to Formula XA:

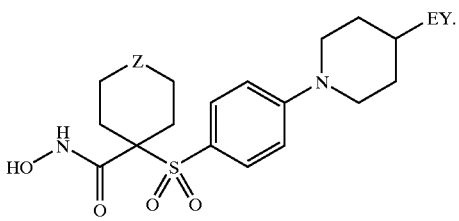

In other embodiments directed to compounds corresponding in structure to Formula X:

Z is —C(O)—, —N($R^6$)—, —O—, —S—, or —S(O)$_2$—. In one particularly preferred embodiment, Z is —N($R^6$)—. In another particularly preferred embodiment, Z is —O—.

$R^6$ is hydrogen, arylalkoxycarbonyl, alkylcarbonyl, alkyl, alkoxyalkyl, cycloalkyl, heteroarylcarbonyl, heteroaryl, cycloalkylalkyl, alkylsulfonyl, haloalkylcarbonyl, alkenyl, alkynyl, and $R^8R^9$-aminoalkylcarbonyl.

In some particularly preferred embodiments, $R^6$ is hydrogen, aryl-$C_1$–$C_6$-alkoxycarbonyl, $C_1$–$C_6$-alkoxycarbonyl, $C_1$–$C_6$-alkyl (preferably isopropyl), $C_1$–$C_6$-alkoxy-$C_1$–$C_6$-alkyl, $C_3$–$C_6$-cycloalkyl, heteroaryl, heteroarylcarbonyl, halo-$C_1$–$C_6$-alkylcarbonyl, or $R^8R^9$-amino-$C_1$–$C_6$-alkylcarbonyl.

In other particularly preferred embodiments, $R^6$ is $C_1$–$C_6$-alkyl (preferably ethyl), $C_1$–$C_6$-alkoxy-$C_1$–$C_6$-alkyl (preferably methoxyethyl), $C_3$–$C_6$-cycloalkyl (preferably cyclopropyl), $C_3$–$C_8$-cycloalkyl-$C_1$–$C_6$-alkyl (preferably cyclopropylmethyl), $C_3$–$C_6$-alkenyl (preferably $C_3$-alkenyl), $C_3$–$C_6$-alkynyl (preferably $C_3$-alkynyl), or $C_1$–$C_6$-alkylsulfonyl (preferably methylsulfonyl).

$R^8$ and $R^9$ are independently selected from the group consisting of hydrogen, alkyl, alkoxy, hydroxyalkyl, alkoxyalkyl, hydroxyalkoxyalkyl, heteroarylalkyl, cycloalkylalkyl, heterocyclylcarbonyl, haloalkyl, and aminoalkyl. Here, the aminoalkyl nitrogen optionally is substituted with up to two substituents independently selected from the group consisting of alkyl.

Alternatively, $R^8$ and $R^9$, together with the atom to which they are bonded, form a 5- to 8-membered heterocyclyl or heteroaryl containing up to 3 (in many instances, no greater than 2) heteroatoms independently selected from the group consisting of nitrogen, oxygen, and sulfur. Here, any such heterocyclyl or heteroaryl (particularly heterocyclyl) optionally is substituted with one or more substituents independently selected from the group consisting of hydroxy, keto, carboxy, alkoxyalkyl, hydroxyalkyl, hydroxyalkoxyalkyl, alkoxycarbonylalkyl, heterocyclylalkyl, alkoxycarbonyl, and aminoalkyl. The aminoalkyl nitrogen, in turn, optionally is substituted with up to two substituents independently selected from the group consisting of alkyl.

E is a bond, —C(O)—, or —S—.

Y is cycloalkyl, 2,3-dihydroindolyl, heterocyclyl, aryl, heteroaryl, arylalkyl, or heteroarylalkyl. Here, the cycloalkyl, 2,3-dihydroindolyl, heterocyclyl, aryl, heteroaryl, arylalkyl, or heteroarylalkyl optionally is substituted with one or more substituents independently selected from the group consisting of halogen, hydroxy, keto, alkyl, haloalkyl, hydroxyalkyl, alkenyl, alkoxy, alkylcarbonyl, haloalkoxy, alkylthio, alkoxyalkyl, alkoxycarbonylalkyl, cycloalkyl, cycloalkylalkyl, cycloalkyloxy, cycloalkylalkoxy, cycloalkylalkoxyalkyl, aryl, arylalkyl, arylalkoxy, heterocyclyl, heterocyclylalkyl, heteroaryl, heteroarylcarbonyl, heterocyclylcarbonylalkyl, alkylsulfonyl, amino, aminoalkyl, and aminocarbonyl.

These optional substituents, in turn, optionally are substituted with one or more substituents independently selected from the group consisting of halogen, nitro, alkyl, haloalkyl, alkoxy, haloalkoxy, and alkylcarbonyl. Additionally, the nitrogen of the amino, aminoalkyl, or aminocarbonyl optionally is substituted with up to two substituents independently selected from the group consisting of alkyl and cycloalkylalkyl.

In some preferred embodiments, E is —C(O)—, and Y is heterocyclyl, aryl (particularly phenyl), heteroaryl, or arylmethyl (particularly phenylmethyl). Here, the heterocyclyl, aryl, heteroaryl, or arylmethyl optionally is substituted with one or more substituents independently selected from the group consisting of halogen, hydroxy, $C_1$–$C_6$-alkyl, halo-$C_1$–$C_6$-alkyl, hydroxy-$C_1$–$C_6$-alkyl, $C_2$–$C_6$-alkenyl, $C_1$–$C_6$-alkoxy, $C_1$–$C_6$-alkylcarbonyl, halo-$C_1$–$C_6$-alkoxy, $C_1$–$C_6$-alkylthio, $C_1$–$C_6$-alkoxy-$C_1$–$C_6$-alkyl, $C_1$–$C_6$-alkoxycarbonyl-$C_1$–$C_6$-alkyl, $C_3$–$C_6$-cycloalkyl, aryl, aryl-$C_1$–$C_6$-alkyl, aryl-$C_1$–$C_6$-alkoxy, heterocyclyl, heterocyclyl-$C_1$–$C_6$-alkyl, heteroaryl, heteroarylcarbonyl, heterocyclylcarbonyl-$C_1$–$C_6$-alkyl, amino, and amino-$C_1$–$C_6$-alkyl. These optional substituents, in turn, are optionally substituted with one or more substituents independently selected from the group consisting of halogen, nitro, $C_1$–$C_6$-alkyl, halo-$C_1$–$C_6$-alkyl, $C_1$–$C_6$-alkoxy, and $C_1$–$C_6$-alkylcarbonyl. Additionally, the nitrogen of the amino or amino-$C_1$–$C_6$-alkyl optionally is substituted with up to two substituents independently selected from the group consisting of $C_1$–$C_6$-alkyl and $C_3$–$C_6$-cycloalkyl-$C_1$–$C_6$-alkyl.

In other preferred embodiments, E is —C(O)—, and Y is aryl (particularly phenyl), heteroaryl, arylmethyl (particularly phenylmethyl), or heteroarylmethyl. The aryl, heteroaryl, arylmethyl, or heteroarylmethyl optionally is substituted with one or more substituents independently selected from the group consisting of halogen, $C_1$–$C_6$-alkyl, hydroxy-$C_1$–$C_6$-alkyl, $C_2$–$C_6$-alkenyl, $C_1$–$C_6$-alkoxy, $C_1$–$C_6$-alkoxy-$C_1$–$C_6$-alkyl, $C_3$–$C_6$-cycloalkyl-$C_1$–$C_6$-alkyl, $C_3$–$C_6$-cycloalkyloxy, $C_3$–$C_6$-cycloalkyl-$C_1$–$C_6$-alkoxy, $C_3$–$C_6$-cycloalkyl-$C_1$–$C_6$-alkoxy-$C_1$–$C_6$-alkyl, heterocyclyl-$C_1$–$C_6$-alkyl, amino, and amino-$C_1$–$C_6$-alkyl. And the nitrogen of the amino or amino-$C_1$–$C_6$-alkyl optionally is substituted with up to two substituents independently selected from the group consisting of $C_1$–$C_6$-alkyl. In some such preferred embodiments, Y is optionally substituted phenyl. Such compounds include, for example:

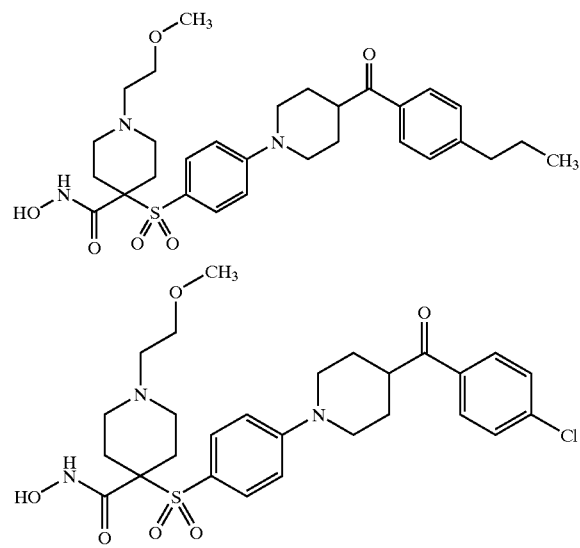

-continued

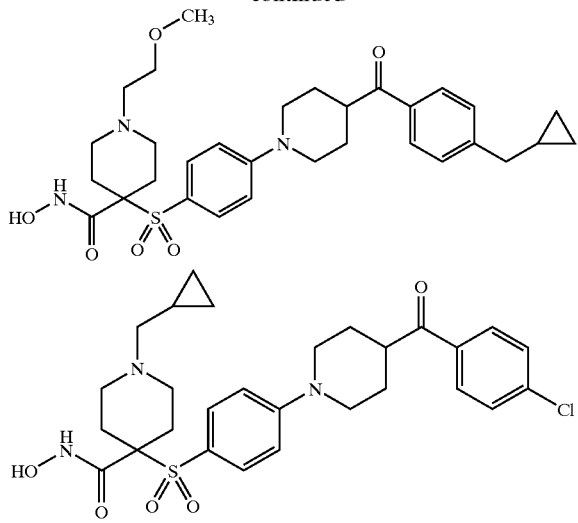

In other such preferred embodiments, Y is optionally substituted heteroaryl. Such compounds include, for example, compounds wherein Y is optionally substituted thienyl:

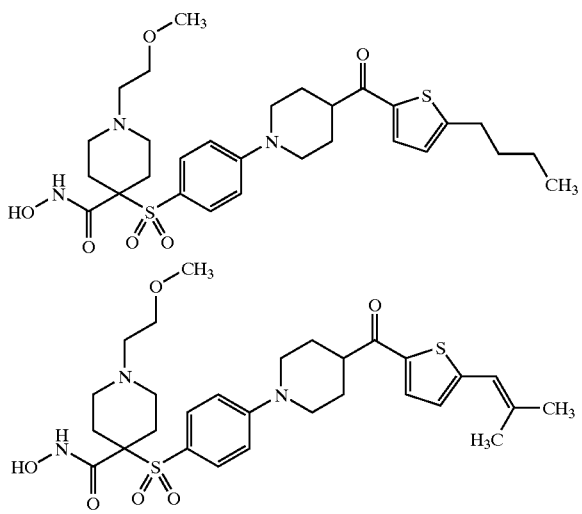

In other preferred embodiments, E is a bond, and Y is aryl (particularly phenyl), 2,3-dihydroindolyl, heterocyclyl, or heteroaryl. The aryl, 2,3-dihydroindolyl, heterocyclyl, or heteroaryl optionally is substituted with one or more substituents independently selected from the group consisting of halogen, keto, hydroxy, $C_1$–$C_6$-alkyl, $C_1$–$C_6$-alkoxy, halo-$C_1$–$C_6$-alkyl, halo-$C_1$–$C_6$-alkoxy, aryl, aminocarbonyl, and $C_1$–$C_6$-alkylsulfonyl. These optional substituents, in turn, also are optionally substituted with one or more substituents independently selected from the group consisting of halogen, halo-$C_1$–$C_6$-alkyl, and halo-$C_1$–$C_6$-alkoxy. Additionally, the nitrogen of the aminocarbonyl optionally is substituted with up to 2 substituents independently selected from the group consisting of $C_1$–$C_6$-alkyl.

In other preferred embodiments, E is a bond, and Y is heteroaryl, aryl (particularly phenyl), or heterocyclyl. The heteroaryl, aryl, or heterocyclyl optionally is substituted with one or more substituents independently selected from the group consisting of halogen, $C_1$–$C_6$-alkyl, $C_1$–$C_6$-alkoxy, and aryl. The optional aryl substituent(s), in turn, optionally is/are substituted with one or more substituents independently selected from the group consisting of halo-$C_1$–$C_6$-alkyl.

In other preferred embodiments, E is —S—, and Y is cycloalkyl, aryl, arylmethyl, or heteroaryl. The cycloalkyl, aryl (particularly phenyl), arylmethyl (particularly phenylmethyl), or heteroaryl optionally is substituted with one or more substituents independently selected from the group consisting of halogen, halo-$C_1$–$C_6$-alkyl, and halo-$C_1$–$C_6$-alkoxy.

In other preferred embodiments, E is —S—, and Y is heteroaryl.

In the above embodiments, R preferably is halogen (preferably chloro or fluoro, and even more preferably chloro). Alternatively, R preferably is hydrogen so that the compound corresponds in structure to Formula XA (shown above).

B. Preparation of useful Compounds

Exemplary chemical transformations that can be useful for preparing compounds and salts of this invention are described in detail in, for example, WIPO Int'l Publ. Nos. WO 00/69821 (published Nov. 23, 2000); WO 00/50396 (published Aug. 31, 2000); and 99/25687 (published May 27, 1999). These references are hereby incorporated by reference into this patent. The reader also is referred to the Example section below, which describes the preparation of numerous compounds and salts of this invention.

C. Salts of the Compounds of this Invention

The compounds of this invention can be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. Pharmaceutically acceptable salts include salts commonly used to form alkali metal salts and to form addition salts of free acids or free bases. In general, these salts typically may be prepared by conventional means with a compound of this invention by reacting, for example, the appropriate acid or base with the compound.

Pharmaceutically-acceptable acid addition salts of the compounds of this invention may be prepared from an inorganic or organic acid. Examples of suitable inorganic acids include hydrochloric, hydrobromic acid, hydroionic, nitric, carbonic, sulfuric, and phosphoric acid. Suitable organic acids generally include, for example, aliphatic, cycloaliphatic, aromatic, araliphatic, heterocyclyl, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically-acceptable base addition salts of the compounds of this invention include, for example, metallic salts and organic salts. Preferred metallic salts include alkali metal (group Ia) salts, alkaline earth metal (group IIa) salts, and other physiological acceptable metal salts. Such salts may be made from aluminum, calcium, lithium, magnesium, potassium, sodium, and zinc. Preferred organic salts can be made from tertiary amines and quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$–$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), aralkyl halides (e.g., benzyl and phenethyl bromides), and others.

Particularly preferred salts of the compounds of this invention include hydrochloric acid (HCl) salts and trifluoroacetate ($CF_3COOH$ or TFA) salts.

D. Preventing or Treating Conditions using the Compounds and Salts of this Invention One embodiment of this invention is directed to a process for preventing or treating a pathological condition associated with MMP activity in a mammal (e.g., a human, companion animal, farm animal, laboratory animal, zoo animal, or wild animal) having or disposed to having such a condition. Such a condition may be, for example, tissue destruction, a fibrotic disease, pathological matrix weakening, defective injury repair, a cardiovascular disease, a pulmonary disease, a kidney disease, and a central nervous system disease. Specific examples of such conditions include osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermolysis bullosa, aortic aneurysm, weak injury repair, an adhesion, scarring, congestive heart failure, coronary thrombosis, emphysema, proteinuria, and Alzheimer's disease.

The condition may alternatively (or additionally) be associated with TNF-α convertase activity. Examples of such a condition include inflammation (e.g., rheumatoid arthritis), autoimmune disease, graft rejection, multiple sclerosis, a fibrotic disease, cancer, an infectious disease (e.g., malaria, mycobacterial infection, meningitis, etc.), fever, psoriasis, a cardiovascular disease (e.g., post-ischemic reperfusion injury and congestive heart failure), a pulmonary disease, hemorrhage, coagulation, hyperoxic alveolar injury, radiation damage, acute phase responses like those seen with infections and sepsis and during shock (e.g., septic shock, hemodynamic shock, etc.), cachexia, and anorexia.

The condition may alternatively (or additionally) be associated with aggrecanase activity. Examples of such a condition include inflammation diseases (e.g., osteoarthritis, rheumatoid arthritis, joint injury, reactive arthritis, acute pyrophosphate arthritis, and psoriatic arthritis) and cancer.

In this patent, the phrase "preventing a condition" means reducing the risk of (or delaying) the onset of the condition in a mammal that does not have the condition, but is predisposed to having the condition. In contrast, the phrase "treating a condition" means ameliorating, suppressing, or eradicating an existing condition. The pathological condition may be, for example: (a) the result of pathological MMP and/or aggrecanase activity itself, (b) affected by MMP activity (e.g., diseases associated with TNF-α, and/or (c) affected by aggrecanase activity.

A wide variety of methods may be used alone or in combination to administer the hydroxamates and salt thereof described above. For example, the hydroxamates or salts thereof may be administered orally, parenterally, by inhalation spray, rectally, or topically. Oral administration can be advantageous if, for example, the patient is ambulatory, not hospitalized, and physically able and sufficiently responsible to take drug at the required intervals. This may be true even if the person is being treated with more than one drug for one or more diseases. On the other hand, IV drug administration can be advantageous in, for example, a hospital setting where the dose (and thus the blood levels) can be well controlled. A compound or salt of this invention also can be formulated for IM administration if desired. This route of administration may be desirable for administering prodrugs or regular drug delivery to patients that are either physically weak or have a poor compliance record or require constant drug blood levels.

Typically, a compound (or pharmaceutically acceptable salt thereof) described in this patent is administered in an amount effective to inhibit a target MMP(s). The target MMP is/are typically MMP-2, MMP-9, and/or MMP-13, with MMP-13 often being a particularly preferred target. The preferred total daily dose of the hydroxamate or salt thereof (administered in single or divided doses) is typically from about 0.001 to about 100 mg/kg, more preferably from about 0.001 to about 30 mg/kg, and even more preferably from about 0.01 to about 10 mg/kg (i.e., mg hydroxamate or salt thereof per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular hydroxamate or salt thereof employed; whether a drug delivery system is utilized; and whether the hydroxamate or salt thereof is administered as part of a drug combination. Thus, the dosage regimen actually employed can vary widely, and, therefore, can deviate from the preferred dosage regimen set forth above.

E. Pharmaceutical Compositions Containing the Compounds and Salts of this Invention This invention also is directed to pharmaceutical compositions comprising a hydroxamate or salt thereof described above, and to methods for making pharmaceutical compositions (or medicaments) comprising a hydroxamate or salt thereof described above.

The preferred composition depends on the method of administration, and typically comprises one or more conventional pharmaceutically acceptable carriers, adjuvants, and/or vehicles. Formulation of drugs is generally discussed in, for example, Hoover, John E., *Remington's Pharmaceutical Sciences* (Mack Publishing Co., Easton, Pa.: 1975). See also, Liberman, H. A. See also, Lachman, L., eds., *Pharmaceutical Dosage Forms* (Marcel Decker, New York, N.Y., 1980).

Solid dosage forms for oral administration include, for example, capsules, tablets, pills, powders, and granules. In such solid dosage forms, the hydroxamates or salts thereof are ordinarily combined with one or more adjuvants. If administered per os, the hydroxamates or salts thereof can be mixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in a dispersion of the hydroxamate or salt thereof in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions, solutions, suspensions, syrups, and elixirs containing inert diluents commonly used in the art (e.g., water). Such compositions also can comprise adjuvants, such as wetting, emulsifying, suspending, flavoring (e.g., sweetening), and/or perfuming agents.

"Parenteral administration" includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the carriers or diluents mentioned for use in the formulations for oral administration. The hydroxamates or salts thereof can be dissolved in water, polyethylene glycol, propylene glycol, ethanol, corn oil, cottonseed oil, peanut oil, sesame oil, benzyl alcohol, sodium chloride, and/or various buffers.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, such as cocoa butter; synthetic mono-, di-, or triglycerides; fatty acids; and/or polyethylene glycols "Topical administration" includes the use of transdermal administration, such as transdermal patches or iontophoresis devices.

Other adjuvants and modes of administration known in the pharmaceutical art may also be used.

F. Definitions

The term "alkyl" (alone or in combination with another term(s)) means a straight-or branched-chain saturated hydrocarbyl group typically containing from 1 to about 20 carbon atoms, more typically from about 1 to about 8 carbon atoms, and even more typically from about 1 to about 6 carbon atoms. Examples of such groups include methyl, ethyl, n-propyl, isopropyl, n-butyl, isobutyl, sec-butyl, tert-butyl, pentyl, iso-amyl, hexyl, octyl, and the like.

The term "alkenyl" (alone or in combination with another term(s)) means a straight- or branched-chain hydrocarbyl group containing one or more double bonds and typically from 2 to about 20 carbon atoms, more typically from about 2 to about 8 carbon atoms, and even more typically from about 2 to about 6 carbon atoms. Examples of such groups include ethenyl (vinyl); 2-propenyl; 3-propenyl; 1,4-pentadienyl; 1,4-butadienyl; 1-butenyl; 2-butenyl; 3-butenyl; decenyl; and the like.

The term "alkynyl" (alone or in combination with another term(s)) means a straight- or branched-chain hydrocarbyl group containing one or more triple bonds and typically from 2 to about 20 carbon atoms, more typically from about 2 to about 8 carbon atoms, and even more typically from about 2 to about 6 carbon atoms. Examples of such groups include ethynyl, 2-propynyl, 3-propynyl, decynyl, 1-butynyl, 2-butynyl, 3-butynyl, and the like.

The term "carbocyclyl" (alone or in combination with another term(s)) means a saturated cyclic, partially saturated cyclic, or aryl hydrocarbyl group containing from 3 to 14 carbon ring atoms ("ring atoms" are the atoms bound together to form the ring or rings of a cyclic group). A carbocyclyl may be a single ring, which typically contains from 3 to 6 ring atoms. Examples of such single-ring carbocyclyls include cyclopropanyl, cyclobutanyl, cyclopentyl, cyclopentenyl, cyclopentadienyl, cyclohexyl, cyclohexenyl, cyclohexadienyl, and phenyl. A carbocyclyl alternatively may be 2 or 3 rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluoreneyl, decalinyl, and norpinanyl.

The term "cycloalkyl" (alone or in combination with another term(s)) means a saturated cyclic hydrocarbyl group containing from 3 to 14 carbon ring atoms. A cycloalkyl may be a single carbon ring, which typically contains from 3 to 6 carbon ring atoms. Examples of single-ring cycloalkyls include cyclopropanyl, cyclobutanyl, cyclopentyl, and cyclohexyl. A cycloalkyl alternatively may be 2 or 3 carbon rings fused together, such as, decalinyl or norpinanyl.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl group (e.g., alkyl, alkenyl, alkynyl, or cycloalkyl) is indicated by the prefix "$C_x$-$C_y$-", wherein x is the minimum and y is the maximum number of carbon atoms in the group. Thus, for example, "$C_1$-$C_6$-alkyl" refers to an alkyl group containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "nitro" (alone or in combination with another term(s)) means —NO$_2$.

The term "cyano" (alone or in combination with another term(s)) means —CN, which also may be depicted as or —COOH:

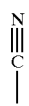

The term "keto" (alone or in combination with another term(s)) means an oxo radical, and may be depicted as =O.

The term "carboxy" (alone or in combination with another term(s)) means —C(O)—OH, which also may be depicted as:

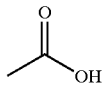

The term "amino" (alone or incombination with another term(s)) means —NH₂. The term "monosubstituted amino" (alone or in combination with another term(s)) means an amino group wherein one of the hydrogen radicals is replaced by a non-hydrogen substituent. The term "disubstituted amino" (alone or in combination with another term(s)) means an amino group wherein both of the hydrogen atoms are replaced by non-hydrogen substituents, which may be identical or different.

The term "halogen" (alone or in combination with another term(s)) means a fluorine radical (which may be depicted as —F), chlorine radical (which may be depicted as —Cl), bromine radical (which may be depicted as —Br), or iodine radical (which may be depicted as —I). Typically, a fluorine radical or chlorine radical is preferred.

If a group is described as being "substituted", at least one hydrogen on the group is replaced with a non-hydrogen substituent. Thus, for example, a substituted alkyl group is an alkyl group wherein at least one hydrogen on the alkyl group is replaced with a non-hydrogen substituent. It should be recognized that if there are more than one substitutions on a group, each non-hydrogen substituent may be identical or different.

If a group is described as being "optionally substituted", the group may be either substituted or not substituted.

The prefix "halo" indicates that the group to which the prefix is attached is substituted with one or more independently selected halogen radicals. For example, haloalkyl means an alkyl group wherein at least one hydrogen radical is replaced with a halogen radical. Examples of haloalkyls include chloromethyl, 1-bromoethyl, fluoromethyl, difluoromethyl, trifluoromethyl, 1,1,1-trifluoroethyl, and the like. Illustrating further, "haloalkoxy" means an alkoxy group wherein at least one hydrogen radical is replaced by a halogen radical. Examples of haloalkoxy groups include chlormethoxy, 1-bromoethoxy, fluoromethoxy, difluoromethoxy, trifluoromethoxy (also known as "perfluoromethyoxy"), 1,1,1,-trifluoroethoxy, and the like. It should be recognized that if a group is substituted by more than one halogen radical, those halogen radicals may be identical or different.

The prefix "perhalo" indicates that every hydrogen radical on the group to which the prefix is attached is replaced with independently selected halogen radicals, i.e., each hydrogen radical on the group is replaced with a halogen radical. If all the halogen radicals are identical, the prefix typically will identify the halogen radical. Thus, for example, the term "perfluoro" means that every hydrogen radical on the group to which the prefix is attached is substituted with a fluorine radical. To illustrate, the term "prefluoroalkyl" means an alkyl group wherein each hydrogen radical is replaced with a fluorine radical. Examples of perfluoroalkyl groups include trifluoromethyl (—CF₃), perfluorobutyl, perfluoroisopropyl, perfluorododecyl, perfluorodecyl, and the like. To illustrate further, the term "perfluoroalkoxy" means an alkoxy group wherein each hydrogen radical is replaced with a fluorine radical. Examples of perfluoroalkoxy groups include trifluoromethoxy (—O—CF₃), perfluorobutoxy, perfluoroisopropoxy, perfluorododecoxy, perfluorodecoxy, and the like.

The term "carbonyl" (alone or in combination with another term(s)) means —C(O)—, which also may be depicted as:

This term also is intended to encompass a hydrated carbonyl group, i.e., —C(OH)₂—.

The term "aminocarbonyl" (alone or incombination with another term(s)) means —C(O)—NH₂, which also may be depicted as:

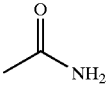

The term "oxy" (alone or incombination with another term(s)) means an ether group, and may be depicted as —O—.

The term "alkoxy" (alone or incombination with another term(s)) means an alkylether group, i.e., —O-alkyl. Examples of such a group include methoxy (—O—CH₃), ethoxy, n-propoxy, isopropoxy, n-butoxy, iso-butoxy, sec-butoxy, tert-butoxy, and the like.

The term "alkylcarbonyl" (alone or in combination with another term(s)) means —C(O)-alkyl. For example, "ethylcarbonyl" may be depicted as:

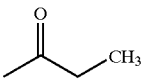

The term "aminoalkylcarbonyl" (alone or in combination with another term(s)) means —C(O)-alkyl—NH₂. For example, "aminomethylcarbonyl" may be depicted as:

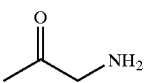

The term "alkoxycarbonyl" (alone or in combination with another term(s)) means —C(O)—O-alkyl. For example, "ethoxycarbonyl" may be depicted as:

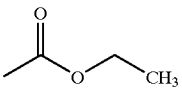

The term "carbocyclylcarbonyl" (alone or in combination with another term(s)) means —C(O)-carbocyclyl. For example, "phenylcarbonyl" may be depicted as:

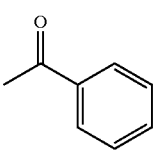

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkylcarbocyclyl. For example, "phenylethylcarbonyl" may be depicted as:

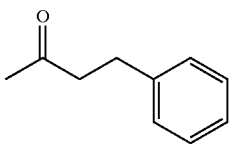

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl. For example, "phenyloxycarbonyl" may be depicted as:

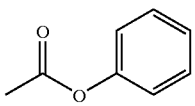

The term "carbocyclylalkoxycarbonyl" (alone or in combination with another term(s)) means —C(O)—O-alkyl-carbocyclyl. For example, "phenylethoxycarbonyl" maybe depicted as:

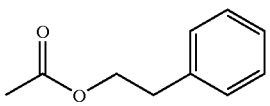

The term "thio" or "thia" (alone or in combination with another term(s)) means a thiaether group, i.e., an ether group wherein the ether oxygen atom is replaced by a sulfur atom. Such a group may be depicted as —S—. This, for example, "alkyl-thio-alkyl" means alkyl-S-alkyl.

The term "thiol" or "sulfhydryl" (alone or in combination with another term(s)) means a sulfhydryl group, and may be depicted as —SH.

The term "(thiocarbonyl)" (alone or in combination with another term(s)) means a carbonyl wherein the oxygen atom has been replaced with a sulfur. Such a group may be depicted as —C(S)—, and also may be depicted as:

The term "alkyl(thiocarbonyl)" (alone or in combination with another term(s)) means —C(S)-alkyl. For example, "ethyl(thiocarbonyl)" may be depicted as:

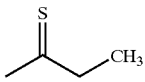

The term "alkoxy(thiocarbonyl)" (alone or in combination with another term(s)) means —C(S)—O-alkyl. For example, "ethoxy(thiocarbonyl)" may may be depicted as:

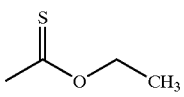

The term "carbocyclyl(thiocarbonyl)" (alone or in combination with another term(s)) means —C(S)-carbocyclyl. For example, "phenyl(thiocarbonyl)" may be depicted as:

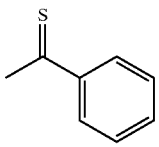

Similarly, the term "heterocyclyl(thiocarbonyl)" (alone or in combination with another term(s)) means —C(S)-heterocyclyl.

The term "carbocyclylalkyl(thiocarbonyl)" (alone or in combination with another term(s)) means —C(S)-alkyl-carbocyclyl. For example, "phenylethyl(thiocarbonyl)" may be depicted as:

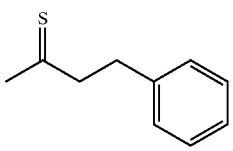

Similarly, the term "heterocyclylalkyl(thiocarbonyl)" (alone or in combination with another term(s)) means —C(S)-alkyl-heterocyclyl.

The term "carbocyclyloxy(thiocarbonyl)" (alone or in combination with another term(s)) means —C(S)—O-carbocyclyl. For example, "phenyloxy(thiocarbonyl)" may be depicted as:

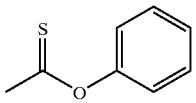

The term "carbocyclylalkoxy(thiocarbonyl)" (alone or in combination with another term(s)) means —C(S)—O-alkyl-carbocyclyl. For example, "phenylethoxy(thiocarbonyl)" maybe depicted as:

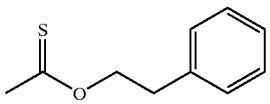

The term "sulfonyl" (alone or in combination with another term(s)) means —S(O)$_2$—, which also may be depicted as:

Thus, for example, "alkyl-sulfonyl-alkyl" means alkyl-S(O)₂-alkyl.

The term "aminosulfonyl" (alone or in combination with another term(s)) means —S(O)2—NH₂, which also may be depicted as:

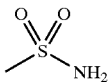

The term "sulfoxido" (alone or in combination with another term(s)) means —S(O)—, which also may be depicted as:

Thus, for example, "alkyl-sulfoxido-alkyl" means alkyl-S(O)-alkyl.

The term "heterocyclyl" (alone or in combination with another term(s)) means a saturated or partially saturated ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single ring, which typically contains from 3 to 7 ring atoms, more typically from 3 to 6 ring atoms, and even more typically 5 to 6 ring atoms. A heterocyclyl alternatively may be 2 or 3 rings fused together.

The term "heteroaryl" (alone or in combination with another term(s)) means an aromatic ring containing from 5 to 14 ring atoms. At least one of the ring atoms is a heteroatom, with the remaining ring atoms being independently selected from the group consisting of carbon, oxygen, nitrogen, and sulfur. A heteroaryl may be a single ring, which typically contains from 5 to 7 ring atoms, and more typically from 5 to 6 ring atoms. A heteroaryl alternatively may be 2 or 3 rings fused together.

Examples of single-ring heterocyclyls and heteroaryls include furanyl, dihydrofurnayl, tetradydrofurnayl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl (including 1,2-pyranyl or 1,4-pyranyl), dihydropyranyl, pyridinyl (also known as "azinyl"), piperidinyl, diazinyl (including pyridazinyl (also known as "1,2-diazinyl"), pyrimidinyl (also known as "1,3-diazinyl"), or pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), oxazinyl (including 1,2,3-oxazinyl, 1,3,2-oxazinyl, 1,3,6-oxazinyl (also known as "pentoxazolyl"), 1,2,6-oxazinyl, or 1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl or 1,3,5,2-oxadiazinyl), morpholinyl, azepinyl, oxepinyl, thiepinyl, and diazepinyl.

Examples of heterocyclyl and heteroaryl rings having 2 or 3 rings fused together include, for example, indolizinyl, pyrindinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (also known as "isobenzazolyl" or "pseudoisoindolyl"), indoleninyl (also known as "pseudoindolyl"), isoindazolyl (also known as "benzpyrazolyl"), benzazinyl (including quinolinyl (also known as "1-benzazinyl") or isoquinolinyl (also known as "2-benzazinyl")), phthalazinyl, quinoxalinyl, quinazolinyl, benzodiazinyl (including cinnolinyl (also known as "1,2-benzodiazinyl") or quinazolinyl (also known as "1,3-benzodiazinyl")), benzopyranyl (including "chromanyl" or "isochromanyl"), benzothiopyranyl (also known as "thiochromanyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", or "benzothiofuranyl"), isobenzothienyl (also known as "isobenzothiophenyl", "isothionaphthenyl", or "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, or 3,1,4-benzoxazinyl ), benzisoxazinyl (including 1,2-benzisoxazinyl or 1,4-benzisoxazinyl), tetrahydroisoquinolinyl , carbazolyl, xanthenyl, and acridinyl.

As may be seen in the preceding paragraphs, the term "heteroaryl" includes 6-membered ring substituents such as pyridyl, pyrazyl, pyrimidinyl, and pyridazinyl; 5-membered ring substituents such as 1,3,5-, 1,2,4- or 1,2,3-tiiazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as 1,2-, 1,4-, 2,3- and 2,1-benzopyronyl, quinolinyl, isoquinolinyl, cinnolinyl, quinazolinyl, and 1,4-benzoxazinyl.

A carbocyclyl, heterocyclyl, or heteroaryl optionally can be substituted with, for example, one or more substituents independently selected from the group consisting of halogen, hydroxy, carboxy, keto, alkyl, alkoxy, alkoxyalkyl, alkylcarbonyl (also known as "alkanoyl"), aryl, arylalkyl, arylalkoxy, arylalkoxyalkyl, arylalkoxycarbonyl, cycloalkyl, cycloalkylalkyl, cycloalkylalkoxy, cycloalkylalkoxyalkyl, and cycloalkylalkoxycarbonyl. More typically, a carbocyclyl or heterocyclyl may optionally be substituted with, for example, one or more substituents independently selected from the group consisting of halogen, —OH, —C(O)—OH, keto, $C_1$–$C_6$-alkyl, $C_1$–$C_6$-alkoxy, $C_1$–$C_6$-alkoxy-$C_1$–$C_6$-alkyl, $C_1$–$C_6$-alkylcarbonyl, aryl, aryl-$C_1$–$C_6$-alkyl, aryl-$C_1$–$C_6$-alkoxy, aryl-$C_1$–$C_6$-alkoxy-$C_1$–$C_6$-alkyl, aryl-$C_1$–$C_6$-alkoxycarbonyl, cycloalkyl, cycloalkyl-$C_1$–$C_6$-alkyl, cycloalkyl-$C_1$–$C_6$-alkoxy, cycloalkyl-$C_1$–$C_6$-alkoxy-$C_1$–$C_6$-alkyl, and cycloalkyl-$C_1$–$C_6$-alkoxycarbonyl. The alkyl, alkoxy, alkoxyalkyl, alkylcarbonyl, aryl, arylalkyl, arylalkoxy, arylalkoxyalkyl, or arylalkoxycarbonyl substituent(s) may further be substituted with, for example, one or more halogen. The aryls or cycloalkyls are typically single-ring groups containing from 3 to 6 ring atoms, and more typically from 5 to 6 ring atoms.

An aryl or heteroaryl optionally can be substituted with, for example, one or more substituents independently selected from the group consisting of halogen, —OH, —CN, —NO$_2$, —SH, —C(O)—OH, amino, aminocarbonyl, aminoalkyl, alkyl, alkylthio, carboxyalkylthio, alkylcarbonyl, alkylcarbonyloxy, alkoxy, alkoxyalkyl, alkoxycarbonyl, alkoxycarbonylalkoxy, alkoxyalkylthio, alkoxycarbonylalkylthio, carboxyalkoxy, alkoxycarbonylalkoxy, carbocyclyl, carbocyclylalkyl, carbocyclyloxy, carbocyclylthio, carbocyclylalkylthio, carbocyclylamino, carbocyclylalkylamino, carbocyclylcarbonylamino, carbocyclylcarbonyl, carbocyclylalkyl, carbonyl, carbocyclylcarbonyloxy, carbocyclyloxycarbonyl, carbocyclylalkoxycarbonyl, carbocyclyloxyalkoxycarbocyclyl, carbocyclylthioalkylthiocarbocyclyl, carbocyclylthioalkoxycarbocyclyl, carbocyclyloxyalkylthiocarbocyclyl, heterocyclyl, heterocyclylalkyl, heterocyclyloxy, heterocyclylthio, heterocyclylalkylthio, heterocyclylamino, heterocyclylalkylamino, heterocyclylcarbonylamino, heterocyclylcarbonyl, heterocyclylalkylcarbonyl, heterocyclyloxycarbonyl, heterocyclylcarbonyloxy, heterocyclylalkoxycarbonyl, heterocyclyloxyalkoxyheterocyclyl, heterocyclylthioalkylthioheterocyclyl, heterocyclylthioalkoxyheterocyclyl, and heterocyclyloxyalkylthioheterocyclyl. More typically, an aryl or heteroaryl may, for example, optionally be substituted with one or more substituents independently selected from the group consisting of halogen, —OH, —CN, —NO$_2$, —SH, —C(O)—OH, amino, aminocarbonyl, amino-C$_1$–C$_6$-alkyl, C$_1$–C$_6$-alkyl, C$_1$–C$_6$-alkylthio, carboxy-C$_1$–C$_6$-alkylthio, C$_1$–C$_6$-alkylcarbonyl, C$_1$–C$_6$-alkylcarbonyloxy, C$_1$–C$_6$-alkoxy, C$_1$–C$_6$-alkoxy-C$_1$–C$_6$-alkyl, C$_1$–C$_6$-alkoxycarbonyl, C$_1$–C$_6$-alkoxycarbonyl-C$_1$–C$_6$-alkoxy, C$_1$–C$_6$-alkoxy-C$_1$–C$_6$-alkylthio, C$_1$–C$_6$-alkoxycarbonyl-C$_1$–C$_6$-alkylthio, carboxy-C$_1$–C$_6$-alkoxy, C$_1$–C$_6$-alkoxycarbonyl-C$_1$–C$_6$-alkoxy, aryl, aryl-C$_1$–C$_6$-alkyl, aryloxy, arylthio, aryl-C$_1$–C$_6$-alkylthio, arylamino, aryl-C$_1$–C$_6$-alkylamino, arylcarbonylamino, arylcarbonyl, aryl-C$_1$–C$_6$-alkylcarbonyl, arylcarbonyloxy, aryloxycarbonyl, aryl-C$_1$–C$_6$-alkoxycarbonyl, aryloxy-C$_1$–C$_6$-alkoxyaryl, arylthio-C$_1$–C$_6$-alkylthioaryl, arylthio-C$_1$–C$_6$-alkoxyaryl, aryloxy-C$_1$–C$_6$-alkylthioaryl, cycloalkyl, cycloalkyl-C$_1$–C$_6$-alkyl, cycloalkyloxy, cycloalkylthio, cycloalkyl-C$_1$–C$_6$-alkylthio, cycloalkylamino, cycloalkyl-C$_1$–C$_6$-alkylamino, cycloalkylcarbonylamino, cycloalkylcarbonyl, cycloalkyl-C$_1$–C$_6$-alkylcarbonyl, cycloalkylcarbonyloxy, cycloalkyloxycarbonyl, cycloalkyl-C$_1$–C$_6$-alkoxycarbonyl, heteroaryl, heteroaryl-C$_1$–C$_6$-alkyl, heteroaryloxy, heteroarylthio, heteroaryl-C$_1$–C$_6$-alkylthio, heteroarylamino, heteroaryl-C$_1$–C$_6$-alkylamino, heteroarylcarbonylamino, heteroarylcarbonyl, heteroaryl-C$_1$–C$_6$-alkylcarbonyl, heteroaryloxycarbonyl, heteroarylcarbonyloxy, and heteroaryl-C$_1$–C$_6$-alkoxycarbonyl. Here, one or more hydrogens bound to a carbon in any such group may, for example, optionally be replaced with halogen. In addition, the cycloalkyl, aryl, and heteroaryl are typically single-ring groups containing 3 to 6 ring atoms, and more typically 5 or 6 ring atoms.

In some embodiments, an aryl or heteroaryl optionally is substituted with one or more substituents independently selected from the group consisting of cyano, perfluoroalkyl, trifluoromethoxy, trifluoromethylthio, haloalkyl, trifluoromethylalkyl, aralkoxycarbonyl, aryloxycarbonyl, hydroxy, halo, alkyl, alkoxy, nitro, thiol, hydroxycarbonyl, aryloxy, arylthio, aralkyl, aryl, arylcarbonylamino, heteroaryloxy, heteroarylthio, heteroaralkyl, cycloalkyl, heterocylyloxy, heterocylylthio, heterocylylamino, cycloalkyloxy, cycloalkylthio, heteroaralkoxy, heteroaralkylthio, aralkoxy, aralkylthio, aralkylamino, heterocylyl, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, aminocarbonyl, and aminoalkyl. Here, the amino nitrogen optionally is substituted with:

(i) up two substituents that are independently selected from the group consisting of alkyl, aryl, heteroaryl, aralkyl, cycloalkyl, aralkoxycarbonyl, alkoxycarbonyl, arylcarbonyl, aralkanoyl, heteroarylcarbonyl, heteroaralkanoyl, and alkanoyl; or (ii) two substituents such that the two substituents, together with the amino nitrogen, form a 5- to 8-member heterocyclyl or heteroaryl ring that:

(a) contains from zero to two additional heteroatoms that are independently selected from the group consisting of nitrogen, oxygen, and sulfur;

(b) optionally is substituted with up to two substituents independently selected from the group consisting of aryl, alkyl, heteroaryl, aralkyl, heteroaralkyl, hydroxy, alkoxy, alkanoyl, cycloalkyl, heterocylylalkyl, alkoxycarbonyl, hydroxyalkyl, trifluoromethyl, benzofused heterocylylalkyl, hydroxyalkoxyalkyl, aralkoxycarbonyl, hydroxycarbonyl, aryloxycarbonyl, benzofused heterocylylalkoxy, benzofused cycloalkylcarbonyl, heterocyclylalkylcarbonyl, and cycloalkylcarbonyl.

The aminocarbonyl nitrogen is:

(i) unsubstituted;

(ii) the reacted amine of an amino acid;

(iii) substituted with one or two substituents independently selected from the group consisting of alkyl, hydroxyalkyl, hydroxyheteroaralkyl, cycloalkyl, aralkyl, trifluoromethylalkyl, heterocylylalkyl, benzofused heterocylylalkyl, benzofused cycloalkyl, and N,N-dialkylsubstituted alkylaminoalkyl; or (iv) substituted with two substituents such that the two substituents, together with the aminocarbonyl nitrogen, form a 5- to 8-member heterocyclyl or heteroaryl ring that optionally is substituted with up to two substituents independently selected from the group consisting of alkyl, alkoxycarbonyl, nitro, heterocylylalkyl, hydroxy, hydroxycarbonyl, aryl, aralkyl, heteroaralkyl, and amino, wherein the amino nitrogen optionally is substituted with:

(a) two substituents independently selected from the group consisting of alkyl, aryl, and heteroaryl; or (b) two substituents such that the two substituents, together with the amino nitrogen, form a 5- to 8-member heterocyclyl or heteroaryl ring.

The aminoalkyl nitrogen optionally is substituted with:

(i) up to two substituents independently selected from the group consisting of alkyl, aryl, aralkyl, cycloalkyl, aralkoxycarbonyl, alkoxycarbonyl, and alkanoyl; or (ii) two substituents such that the two substituents, together with the aminoalkyl nitrogen, form a 5- to 8-member heterocyclyl or heteroaryl ring.

A prefix attached to a multi-component group only applies to the first component. To illustrate, the term "alkylcycloalkyl" contains two components: alkyl and cycloalkyl. Thus, the $C_1$–$C_6$-prefix on $C_1$–$C_6$-alkylcycloalkyl means that the alkyl component of the alkylcycloalkyl contains from 1 to 6 carbon atoms; the $C_1$–$C_6$-prefix does not describe the cycloalkyl component. To illustrate further, the prefix "halo" on haloalkoxyalkyl indicates that only the alkoxy component of the alkoxyalkyl group is substituted with one or more halogen radicals. If halogen substitution may alternatively or additionally occur on the alkyl component, the group would instead be described as "halogen-substituted alkoxyalkyl" rather than "haloalkoxyalkyl." And finally, if the halogen substitution may only occur on the alkyl component, the group would instead be described as "alkoxyhaloalkyl."

If substituents are described as being "independently selected" from a group, each substituent is selected independent of the other. Each substituent therefore may be identical to or different from the other substituent(s).

When words are used to describe a substituent, the rightmost-described component of the substituent is the component that is bound at the location of the replaced hydrogen. To illustrate, benzene substituted with methoxyethyl has the following structure:

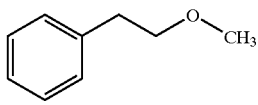

As can be seen, the ethyl is bound to the benzene, and the methoxy is the component of the substituent that is the component furthest from the benzene. As further illustration, benzene substituted with cyclohexanylthiobutoxy has the following structure:

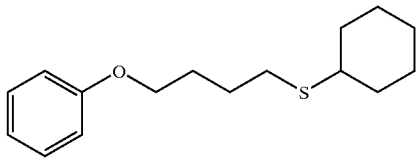

When words are used to describe a linking element between two other elements of a depicted chemical structure, the rightmost-described component of the substituent is the component that is bound to the left element in the depicted structure. To illustrate, if the chemical structure is X—L—Y and L is described as methylcyclohexanylethyl, the chemical would be X-ethyl-cyclohexanyl-methyl-Y.

When a chemical formula is used to describe a substituent, the dash on the left side of the formula indicates the portion of the substituent that is bound at the location of the replaced hydrogen. To illustrate, benzene substituted with —C(O)—OH has the following structure:

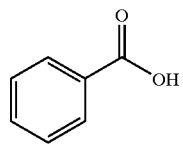

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X—L—Y and L is described as —C(O)—N(H)—, the chemical would be:

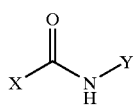

The term "pharmaceutically acceptable" is used adjectivally in this patent to mean that the modified noun is appropriate for use as a pharmaceutical product or as a part of a pharmaceutical product.

With reference to the use of the words "comprise" or "comprises" or "comprising" in this patent (including the claims), Applicants note that unless the context requires otherwise, those words are used on the basis and clear understanding that they are to be interpreted inclusively, rather than exclusively, and that Applicants intend each of those words to be so interpreted in construing this patent, including the claims below.

EXAMPLES

The following examples are merely illustrative, and not intended to be limiting to the remainder of this disclosure in any way.

Abbreviations are often used for reagents and solvents in the specific examples that follow. Those abbreviations include the following:

BOC=t-butoxycarbonyl
DEAD=diethyl azodicarboxylate
DMF=dimethylformamide
DMPU=1,3-dimethyl-3,4,5,6-tetrahydro-2(1H)-pyrimidinone
EtOAc ethyl acetate
EDC=1-ethyl-3-[3-(dimethylamino)-propyl]carbodiimide hydrochloride
$Et_2O$ =diethyl ether
HOBT 1-hydroxybenzotriazole
MeOH=methanol
$MeCl_2$=methylene chloride
MsCl=methanesulfonyl chloride
NMM=N-methyl morpholine
THF=tetrahydrofruan
TsCl=toluenesulfonyl chloride
THP-O-hydroxylamine=O-tetrahydropyran-hydroxylamine and O-tetrahydro-2H-pyran-2-yl-hydroxylamine The preparation of compounds useful in the synthesis of compounds of the invention are provided herein below in Preparative Examples I through XI.

Preparative Example I

Preparation of 1,1-dimethylethyl ester 4-[(hydroxyamino)-carbonyl]-4-[(phenoxyphenyl)-sulfonyl]-1-piperidinecarboxylic acid

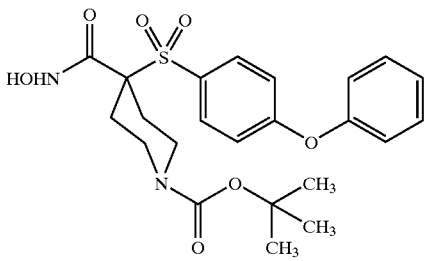

Part A: A solution of 4-(phenoxy)benzenethiol (2.03 g, 10.0 mmol) in DMSO (DMSO; 20 mL) was heated to 65° C. for 5 hr. The solution remained at ambient temperature for 18 hr. The solution was extracted with ethyl acetate and the combined organic layers were washed with $H_2O$ and saturated NaCl and dried over magnesium sulfate. Concentration in vacuo provided the disulfide as a yellow oil (2.3 g, quantitative yield).

Part B: To a solution of ethyl isonipecotate (15.7 g, 0.1 mol) in THF (100 mL) was added a solution of di-tert-butyl dicarbonate (21.8 g, 0.1 mol) in THF (5 mL) drop-wise over 20 min. The solution was stirred overnight (about 18° C.) at ambient temperature and concentrated in vacuo to yield a light oil. The oil was filtered through silica gel (7:3 ethyl acetate/hexanes) and concentrated in vacuo to give the BOC-piperidine compound (26.2 g, quantitative yield) as a clear, colorless oil.

Part C: To a solution of diisopropylamine (2.8 mL, 20 mmoL) in THF (30 mL), cooled to −78° C., was added n-butyl lithium (12.5 mL, 20 mmol) drop-wise. After 15 min, the BOC-piperidine compound of part B (2.6 g, 10 mmol) in THF (10 mL) was added drop-wise. After 1.5 hr, the solution was cooled to −60° C. and the disulfide of part A (2.0 g, 10 mmol) in THF (7 mL). The solution was stirred at ambient temperature for 2 hr. The solution was diluted with $H_2O$ and extracted with ethyl acetate. The organic layer was washed with $H_2O$ and saturated NaCl and dried over magnesium sulfate. Chromatography (on silica, ethyl acetate/hexane) provided the sulfide as an oil (1.8 g, 40%).

Part D: To a solution of the sulfide of part C (1.8 g, 3.95 mmol) in dichloromethane (75 mL) cooled to 0° C., was added m-chloroperbenzoic acid (1.7 g, 7.9 mmol). The solution was stirred for 1.5 hr followed by dilution with $H_2O$ and extraction with dichloromethane. The organic layer was washed with 10 percent $Na_2SO_4$, $H_2O$, and saturated NaCl and dried over magnesium sulfate. Chromatography (on silica, ethyl acetate/hexane) provided the sulfone as a solid (1.15 g, 59%).

Part E: To a solution of the sulfone of part D (800 mg, 1.63 mmol) in THF (9 mL) and ethanol (9 mL) was added NaOH (654 mg, 16.3 mmol) in $H_2O$ (3 mL). The solution was heated at 65° C. for 18 hr. The solution was concentrated in vacuo and the residue was dissolved in $H_2O$. Following acidification with 2N HCl to pH 4, the solution was extracted with ethyl acetate and the organic layer was washed with saturated NaCl and dried over magnesium sulfate. Concentration in vacuo provided the acid as a white foam (790 mg, quantitative yield). Analytical calculated for $C_{23}H_{27}NO_7S$: C, 59.86; H, 5.90; N, 3.04; S, 6.95. Found: C, 59.49; H, 6.37; N, 2.81; S, 6.59.

Part F: To a solution of the acid of part G (730 mg, 1.58 mmol) in DMF (9 mL) was added HOBT (256 mg, 1.90 mmol) followed by EDC (424 mg, 2.21 mmol), 4-methylmorpholine (0.521 mL, 4.7 mmol) and 50 percent aqueous hydroxylamine (1.04 mL, 15.8 mmol). The solution was stirred for 20 hr and additional N-hydroxybenzotriazole.$H_2O$ (256 mg), EDC (424 mg) and 50 percent aqueous hydroxylamine (1.04 mL) were added. After an additional 24 hr of stirring, the solution was diluted with $H_2O$ and extracted with ethyl acetate and the organic layer was washed with saturated NaCl and dried over magnesium sulfate. Reverse phase chromatography (on silica, acetonitrile/$H_2O$) provided the title compound as a white solid (460 mg, 61%). HPLC purity: >99%. Analytical calculated for $C_{23}H_{28}N_2O_7S$: C, 57.97; H, 5.92; N, 5.88; S, 6.73. Found: C, 57.95; H, 6.02; N, 5.81; S, 6.85.

Preparative Example II

Preparation of N-hydroxy-4-[[4-(phenylthio)phenyl]sulfonyl]-1-(2-propynyl)-4-piperidinecarboxamide, monohydrochloride

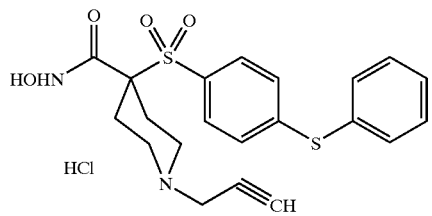

Part A: To a solution of ethyl isonipecotate (15.7 g, 0.1 mol) in THF (100 mL) was added a solution of di-tert-butyl dicarbonate (21.8 g, 0.1 mol) in THF (5 mL) drop-wise over 20 min. The solution was stirred overnight (about 18 hr) at ambient temperature and concentrated in vacuo to yield a light oil. The oil was filtered through silica gel (ethyl acetate/hexanes) and concentrated in vacuo to give the BOC-piperidine compound as a clear, colorless oil (26.2 g, quantitative yield).

Part B: A solution of 4-fluorothiophenol (50.29 g, 390 mmol) in DMSO (500 mL) was heated to 65° C. for 6 hr. The reaction was quenched into wet ice and the resulting solid was collected by vacuum filtration to provide the disulfide as a white solid (34.4 g, 68.9%).

Part C: To a solution of the BOC-piperdine compound of part A (16 g, 62 mmol) in THF (300 mL) cooled to minus 50° C. was added lithium diisopropylamide (41.33 mL, 74 mmol) and the solution was stirred for 1.5 hr at 0° C. To this solution was added the disulfide of part B (15.77 g, 62 mmol), and the resulting solution was stirred at ambient temperature for 20 hr. The reaction was quenched with the addition of $H_2O$ and the solution was concentrated in vacuo. The aqueous residue was extracted with ethyl acetate and the organic layer was washed with 0.5N KOH, $H_2O$, and saturated NaCl. Chromatography (on silica, hexane/ethyl acetate) provided the sulfide as an oil (18.0 g, 75%).

Part D: To a solution of the sulfide of part C (16.5 g, 43 mmol) in dichloromethane (500 mL) cooled to 0° C. was added 3-chloroperbenzoic acid (18.0 g, 86 mmol) and the solution was stirred for 20 hr. The solution was diluted with $H_2O$ and extracted with dichloromethane. The organic layer was washed with 10 percent $Na_2SO_3$, $H_2O$, and saturated NaCl and dried over magnesium sulfate. Chromatography (on silica, ethyl acetate/hexane) provided the sulfone as a solid (10.7 g, 60%).

Part E: Into a solution of the sulfone of part D (10 g, 24.0 mmol) in ethyl acetate (250 mL) was bubbled HCl gas for 10 min followed by stirring at ambient temperature for 4 hr. Concentration in vacuo provided the amine hydrochloride salt as a white solid (7.27 g, 86%).

Part F: To a solution of the amine hydrochloride salt of part E (5.98 g, 17.0 mmol) in DMF (120 mL) was added potassium carbonate (4.7 g, 34.0 mmol) followed by propargyl bromide (2.02 g, 17.0 mmol) and the solution was stirred for 4 hr at ambient temperature. The solution was partitioned between ethyl acetate and H$_2$O, and the organic layer was washed with H$_2$O and saturated NaCl and dried over magnesium sulfate. Chromatography (on silica, ethyl acetate/hexane) provided the propargyl amine as a yellow oil (5.2 g, 86%).

Part G: To a solution of the propargyl amine of part F in DMF (15 mL) was added thiophenol (0.80 mL, 7.78 mmol) and CsCO$_3$ (2.79 g, 8.56 mmol) and the solution was heated to 70° C. for 6 hr. The solution was partitioned between ethyl ether and H$_2$O. The organic layer was washed with H$_2$O and saturated NaCl, and dried over magnesium sulfate. Chromatography (on silica, ethyl acetate/hexane) provided the S-phenoxyphenyl compound as an oil (1.95 g, 56%).

Part H: To a solution of the S-phenoxyphenyl of part G (1.81 g, 4.06 mmol) in ethanol (21 mL) and H20 (3.5 mL) was added KOH (1.37 g, 24.5 mmol) and the solution was heated to 105° C. for 4.5 hr. The solution was acidified to a pH value of 1 with concentrated HCl solution and then concentrated to provide the acid as a yellow residue that was used without additional purification (1.82 g).

Part I: To a solution of the acid of part H (1.82 g, 4.06 mmol) in acetonitrile (20 mL) was added O-tetrahydro-2H-pyran-2-yl-hydroxylamine (723 mg, 6.17 mmol) and triethylamine (0.67 mL, 4.86 mmol). To this stirring solution was added EDC (1.18 g, 6.17 mmol) and the solution was stirred for 18 hr. The solution was partitioned between H$_2$O and ethyl acetate. The organic layer was washed with H$_2$O, saturated NaHCO$_3$ and saturated NaCl and dried over magnesium sulfate. Chromatography (on silica, ethyl acetate/hexane) provided the protected hydroxamate as a white solid (1.32 g, 63%).

Part J: To a solution of the protected hydroxamate of part I (9.65 g, 18.7 mmol) in methanol (148 mL) cooled to 0° C. was added acetyl chloride (4.0 mL, 56.2 mmol), and the solution was stirred for 45 min at ambient temperature. Concentration in vacuo followed by trituration with ethyl ether provided the title compound as a white solid (8.10 g, 94%). MS(CI) MH$^+$ calculated for C$_{21}$H$_{22}$N$_2$O$_4$S$_2$: 431, found 431.

Preparative Example III

Preparation of N-hydroxy-4-[(4-phenoxyphenyl) sulfonyl]-1-(2-propynyl)-4-piperidinecarboxamide, monohydrochloride

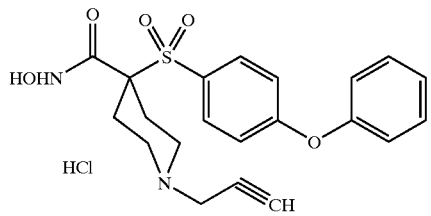

Part A: A solution of 4-(phenoxy)benzenethiol (2.03 g, 10.0 mmol) in DMSO (20 mL) was heated to 65° C. for 5 hr. The solution remained at ambient temperature for 18 hr. The solution was extracted with ethyl acetate and the combined organic layers were washed with H$_2$O and saturated NaCl, and dried over magnesium sulfate. Concentration in vacuo provided the disulfide as a yellow oil (2.3 g, quantitative yield).

Part B: To a solution of ethyl isonipecotate (15.7 g, 0.1 mol) in THF (100 mL) was added a solution of di-tert-butyl dicarbonate (21.8 g, 0.1 mol) in THF (5 mL) dropwise over 20 min. The solution was stirred overnight at ambient temperature and concentrated in vacuo to yield a light oil. The oil was filtered through silica gel (ethyl acetate/hexane) and concentrated in vacuo to give the BOC-piperidine compound as a clear, colorless oil (26.2 g, quantitative yield).

Part C: To a solution of diisopropylamine (2.8 mL, 20 mmoL) in THF (30 mL), cooled to −78° C., was added n-butyl lithium (12.5 mL, 20 mmol) dropwise. After 15 min, the BOC-piperidine compound of Part B (2.6 g, 10 mmol) in THF (10 mL) was added dropwise. After 1.5 hr, the solution was cooled to −60° C. and the disulfide of Part A (2.0 g, 10 mmol) in THF (7 mL) was added. The solution was stirred at ambient temperature for 2 hr. The solution was diluted with H$_2$O and extracted with ethyl acetate. The organic layer was washed with H$_2$O and saturated NaCl and dried over magnesium sulfate. Chromatography (on silica, ethyl acetate/hexane) provided the sulfide as an oil (1.8 g, 40%).

Part D: To a solution of the sulfide of Part C (1.8 g, 3.95 mmol) in dichloromethane (75 mL) cooled to 0° C., was added m-chloroperbenzoic acid (1.7 g, 7.9 mmol). The solution was stirred for 1.5 hr followed by dilution with H$_2$O and extraction with dichloromethane. The organic layer was washed with 10 percent Na$_2$SO$_4$, H$_2$O, and saturated NaCl and dried over magnesium sulfate. Chromatography (on silica, ethyl acetate/hexane) provided the sulfone as a solid (1.15 g, 59%).

Part E: Into a solution of the sulfone of Part D (3.56 g, 7.0 mmol) in ethyl acetate (100 mL) cooled to 0° C. was bubbled HCl gas for 5 min. Concentration in vacuo followed by trituration with ethyl ether provided the amine hydrochloride salt as a white solid (3.5 g, quantitative yield). MS(CI) MH$^+$ calculated for C$_{20}$H$_{23}$NO$_5$S: 390, found 390.

Part F: To a solution of the amine hydrochloride salt of part E (2.6 g, 6 mmol) and K$_2$CO$_3$ (1.66 g, 12 mmol) in DMF (50 mL) was added propargyl bromide (892 mg, 6 mmol) and the solution was stirred at ambient temperature for 4 hr. The solution was diluted with H$_2$O and extracted with ethyl acetate. The combined organic layers were washed with saturated NaCl and dried over magnesium sulfate. Chromatography (on silica, ethyl acetate/hexane) provided the propargyl amine as a white solid (2.15 g, 82%).

Part G: To a solution of the propargyl amine of part F (2.15 g, 5 mmol) in THF (30 mL) and ethanol (30 mL) was added NaOH (2.0 g, 50 mmol) and the solution was heated at 65° C. for 48 hr. The solution was concentrated in vacuo and the aqueous residue was acidified to a pH value of 5. Vacuum filtration of the resulting precipitate provided the acid as a white solid (2.04 g, quantitative yield).

Part H: To a solution of the acid of part G (559 mg, 1.4 mmol) in dichloromethane (5 mL) was added triethylamine (0.585 mL, 4.2 mmol) and 50 percent aqueous hydroxylamine (0.925 mL, 14.0 mmol) followed by bromotris (pyrrolidino)phosphonium hexafluourphosphate (PyBroP®; 718 mg, 1.54 mmol). The solution was stirred at ambient temperature for 4 hr. The solution was diluted with H$_2$O and extracted with dichloromethane. The organic layer was washed with saturated NaCl and dried over magnesium sulfate. Reverse phase chromatography (on silica, acetonitrile/$H_2O$) provided the hydroxamate as a white solid (140 mg, 25%). Analytical calculation for $C_{21}H_{22}N_2O_5S$: C, 60.85; H, 5.37; N, 6.76; S, 7.74. Found: C, 60.47; H, 5.35; N, 6.61; S, 7.46.

Part I: To a solution of the hydroxamate of part H (121 mg, 0.292 mmol) in methanol (2 mL) cooled to 0° C. was added acetyl chloride (0.228 mL, 0.321 mmol) in methanol (1 mL). After stirring at ambient temperature for 30 min, the solution was concentrated under a stream of $N_2$. Trituration with ethyl ether provided the title compound as a white solid (107 mg, 81%). Analytical calculation for $C_{21}H_{22}N_2O_5S \cdot HCl \cdot 0.3H_2O$: C, 55.27; H, 5.21; N, 6.14. Found: C, 54.90; H, 5.37; N, 6.07.

Preparative Example IV

Preparation of 4-[(4-fluorophenyl)sulfonyl] tetrahydro-N-[(tetrahydro-2H-pyran-2-yl)oxy]-2H-pyran-4-carboxamide

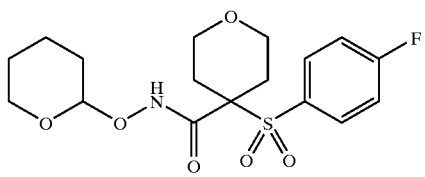

Part A: In dry equipment under nitrogen, sodium metal (8.97 g, 0.39 mol) was added to methanol (1000 mL) at 2° C. The reaction was stirred at ambient temperature for 45 min, at which time the sodium had dissolved. The solution was chilled to 5° C. and p-fluorothiophenol (41.55 mL, 0.39 mmol) was added, followed by methyl 2-chloroacetate (34.2 mL, 0.39 mol). The reaction was stirred at ambient temperature for 4 hr, filtered, and concentrated in vacuo to give the sulfide as a clear colorless oil (75.85 g, 97%).

Part B: To a solution of the sulfide from part A (75.85 g, 0.38 mol) in methanol (1000 mL) were added water (100 mL) and Oxone® (720 g, 1.17 mol) at 20° C. An exotherm to 67° C. was noted. After 2 hr, the reaction was filtered and the cake was washed well with methanol. The filtrate was concentrated in vacuo. The residue was taken up in ethyl acetate and washed with brine, dried over $MgSO_4$, filtered, and concentrated in vacuo to give the sulfone as a crystalline solid (82.74 g, 94%).

Part C: To a solution of the sulfone from part B (28.5 g, 0.123 mol) in N,N-dimethylacetamide (200 mL) were added potassium carbonate (37.3 g, 0.27 mol), bis-(2-bromoethyl) ether (19.3 mL, 0.147 mol), 4-dimethylaminopyridine (0.75 g, 6 mmol), and tetrabutylammonium bromide (1.98 g, 6 mmol). The reaction was stirred overnight (about 18 hr) at ambient temperature. The reaction was slowly poured into 1N HCl (300 mL), the resultant solid filtered and the cake washed well with hexanes. The solid was recrystallized from ethyl acetate/hexanes to give the pyran compound as a beige solid (28.74 g, 77%). MS (ES+) MH+ calculated for $C_{13}H_{15}O_5S_1F_1$: 303, found 303.

Part D: In dry equipment under nitrogen, the pyran compound from part C (8.0 g, 26.5 mmol) was dissolved in dry tetrahydrofuran (250 mL) and a solution of potassium trimethylsilonate (10.2 g, 79.5 mmol) in dry tetrahydrofuran (15 mL) was added at ambient temperature. After 90 min, water (100 mL) was added and the solution concentrated in vacuo. The residue was taken up in water and extracted with ethyl acetate to remove unreacted starting material. The aqueous solution was treated with 6N HCl until pH=1. The slurry was extracted with ethyl acetate and the combined extracts washed with water, dried over $Na_2SO_4$, filtered, and concentrated in vacuo. The residue was heated in diethyl ether, the solid filtered and dried to give the carboxylic acid as a crystalline solid (5.78 g, 76%). HRMS (ES−) M−H calculated for $C_{12}H_{13}O_5 S_1F_1$: 287.04, found 287.04.

Part E: In dry equipment under nitrogen, the carboxylic acid from part D (9.1 g, 31.6 mmol) was dissolved in dry N,N-dimethylformamide (70 mL) and the remaining reagents were added to the solution in the following order: N-hydroxybenzotriazole hydrate (5.1 g, 37.9 mmol), N-methylmorpholine (10.4 mL, 94.8 mmol), O-tetrahydro-2H-pyran-2-yl-hydroxylamine (11.5 g, 98 mmol), and 1-(3-dimethylaminopropyl)-3-ethylcarbodiimide hydrochloride (8.48 g, 44.2 mmol). After 3 hr at ambient temperature, the reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo. Chromatography (on silica, ethyl acetate/hexanes) provided the title compound as a crystalline solid (9.7 g, 80%). HRMS (ES+) MH+ calculated for $C_{17}H_{22}NO_6 S_1F_1$: 388.12, found 388.12.

Preparative Example V

Preparation of tetrahydro-N-hydroxy-4-[[4-[4-trifluoromethoxy)-phenoxy)phenyl]sulfonyl]-2H-pyran-4-carboxamide

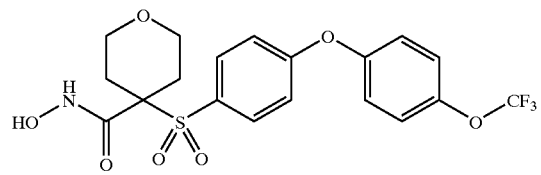

Part A: To a solution of the title compound of Preparative Example IV (3.1 g, 8 mmol) in N,N-dimethylacetamide (20 mL) were added cesium carbonate (8.8 g, 27 mmol) and p-(trifluoromethoxy)phenol (2.1 mL, 16 mmol). The slurry was stirred at 95° C. for 19 hr. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP-protected hydroxamate as a white foam (4.2 g, 96%). HRMS (ES+) MH+ calculated for $C_{24}H_{26}N_1O_8S_1F_3$: 546.14, found 546.14.

Part B: To a slurry of the THP-protected hydroxamate from part A (4.0 g, 7.3 mmol) in dioxane (20 mL) were added a 4N HCl dioxane solution (20 mL) and methanol (20 mL). After 15 min, at ambient temperature, the reaction was diluted with ethyl acetate and washed with water, dried over $Na_2SO_4$, filtered, and concentrated in vacuo. The product was recrystallized (acetone/hexanes) to give the title compound as a white solid (2.2 g, 65%). HRMS (ES+) $M+NH_4^+$ calculated for $C_{19}H_{18}N_1O_7S_1F_3$: 479.11, found 479.11.

Preparative Example VI

Preparation of 1-cyclopropyl-N-hydroxy-4-[4-(2-phenoxy-ethoxy)phenyl]sulfonyl]-4-piperidine carboxamide, monohydrochloride

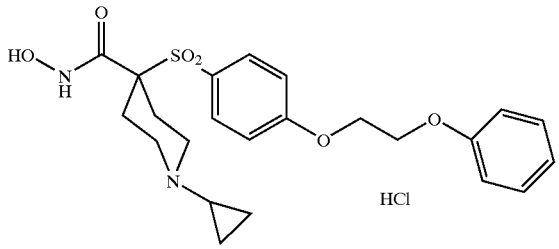

Part A: To a solution of the product of Preparative Example II, part E, (14.36 g, 40 mmol) in methanol (50 mL) was added acetic acid (24.5 g, 400 mmol), a portion (about 2 g) of 4-Ångstrom molecular sieves, (1-ethoxycyclopropyl)-oxytrimethyl silane (25.8 mL, 148 mmol) and sodium cyanoborohydride (7.05 g, 112 mmol). The solution was heated at reflux for 8 hr. The precipitated solids were removed by filtration and the filtrate was concentrated in vacuo. The residue was diluted with $H_2O$ (400 mL) and extracted with ethyl acetate. The organic layer was washed with saturated NaCl and dried over $MgSO_4$, filtered and concentrated in vacuo. The solid was filtered, washed with $H_2O$/diethyl ether to give the desired cyclopropyl amine {ethyl 4-[(4-fluorophenyl-sulfonyl)]-1-cyclopropyl-4-piperidinecarboxylate} as a white solid (11.83 g, 81.5%). MS $MH^+$ calculated for $C_{17}H_{22}NO_4SF$: 356, found: 356.

Part B: A solution of the cyclopropyl amine of Part A (2.0 g, 5.6 mmol), ethylene glycol phenyl ether (2.8 mL, 23 mmol), and cesium carbonate (7.3 g, 23 mmol) in DMAC (10 mL) was heat at 125–135° C. for 18 hr under an atmosphere of nitrogen. The mixture was concentrated in vacuo, diluted with water, and extracted with ethyl acetate. The combined ethyl acetate layers were washed with water and brine, dried over magnesium sulfate, concentrated in vacuo, dissolved in diethyl ether, precipitated as the hydrochloride salt, and dried at 40° C. in a vacuum oven. The solid was dissolved into a mixture of water, acetonitrile, and ethanol and then the pH was adjusted to 12 with 1N NaOH solution. The mixture was concentrated in vacuo to remove ethanol and acetonitrile. The solid was isolated by filtration, washed with water, and dried at 50° C. in a vacuum oven to afford the ether as a white solid (1.8 g, 68%): MS+ calcd. for $C_{25}H31NO_6S$ 474, found 474. Anal. calcd. for $C_{25}H_{31}NO_6S$: C, 63.40; H, 6.60; N, 2.96; S, 6.77. Found: C, 63.35; H, 6.59; N, 2.99; S, 6.61.

Part C: A mixture of the ether of part B (1.8 g, 3.7 mmol) and a 50% NaOH aqueous solution (3.0 g, 37 mmol) in THF (32 mL), EtOH (32 mL), and $H_2O$ (16 mL) was heated at 60° C. under a $N_2$ atmosphere for 24 hr. The material was concentrated in vacuo and triturated with diethyl ether to give a solid. The tan solid was dissolved into a mixture of water, ethanol, and THF, precipitated by adjusting the pH to 3 with concentrated hydrochloric acid, concentrated in vacuo, triturated with water, and dried at 50° C. in a vacuum oven to give a crude white solid acid (2.3 g).

A mixture of the crude white solid acid (2.3 g), N-hydroxybenzotriazole (1.9 g, 14 mmol), 4-methylmorpholine (1.6 mL, 14 mmol), O-tetrahydro-2H-pyran-2-yl-hydroxylamine (1.1 g, 9.4 mmol), and 1-(3-dimethylaminopropyl)-3-ethylcarbodiimide hydrochloride (2.7 g, 14 mmol) in DMF (90 mL) was stirred at ambient temperature under a nitrogen atmosphere for 2 days. The mixture was concentrated in vacuo, diluted with water, and extracted with ethyl acetate. The organic layer was washed with 1N NaOH solution, water, and brine, dried over magnesium sulfate, concentrated in vacuo, and purification by flash chromatography (20:80 to 40:60 ethyl acetate/toluene) to afford the protected hydroxamate as a white solid: (0.43 g, 21%): MS MH+ calcd. for $C_{28}H_{36}N_2O_7S$ 545, found 545. Anal. calcd. for $C_{28}H_{36}N_2O_7S$: C, 61.74; H, 6.66; N, 5.14; S, 5.89. Found: C, 61.72; H, 6.75; N, 5.06; S, 5.91.

Additional compound was isolated by acidifying the aqueous layer to pH of 3, collecting the solid by filtration, and drying to give a white solid (0.80 g).

Part D: To an ambient temperature solution of acetyl chloride (0.31 mL, 4.4 mmol) in methanol (11 mL) under a nitrogen atmosphere was added the protected hydroxamate of part C (0.80 g, 1.5 mmol). After stirring for 2.5 hr, the precipitate was collected by filtration, washed with diethyl ether, and dried at 45° C. in a vacuum oven to afford the title compound as a white solid (0.58 g, 79%): MS MH+ calcd. for $C_{23}H_{28}N_2O_6S$ 461, found 461. Anal. calcd. for $C_{23}H_{28}N_2O_6S$ 1.5HCl: C, 53.62; H, 5.77; N, 5.44; S, 6.22. Found: C, 53.47; H, 5.79; N, 5.41; S, 6.16.

Preparative Example VII

Preparation of N-hydroxy-1-(2-methoxyethyl)-4-[[4-[4-(trifluoro-methoxy)phenoxy]phenyl]sulfonyl}-4-piperidinecarboxamide, monohydrochloride

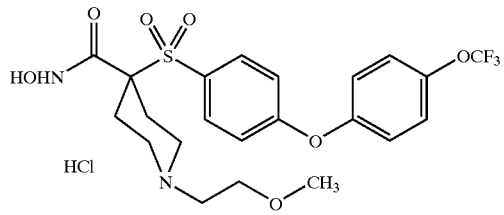

Part A: To a solution of the product of Preparative Example II, Part D (30 g, 161 mmol) in dichloromethane (50 mL) cooled to 0° C. was added trifluroacetic acid (25 mL) and the solution was stirred at ambient temperature for 1 hr. Concentration in vacuo provided the amine trifluoroacetate salt as a light yellow gel. To the solution of the trifluoroacetate salt and $K_2CO_3$ (3.6 g, 26 mmol) in N,N-dimethylformamide (50 mL) cooled to 0° C. was added 2-bromoethyl methyl ether (19 mL, 201 mmol), and solution was stirred at ambient temperature for 36 hr. Then, N,N-dimethylformamide was evaporated under high vacuum and the residue was diluted with ethyl acetate. The organic layer was washed with water and dried over $MgSO_4$. Concentration in vacuo provided the methoxyethyl amine as a light yellow gel (26.03 g, 86.8%).

Part B: To a solution of methoxyethyl amine (6.0 g, 16.0 mmol) of Part A and powdered $K_2CO_3$ (4.44 g, 32 mmol) in N,N-dimethylformamide (30 mL) was added 4-(trifluoromethoxy)phenol (5.72 g, 32 mmol) at ambient temperature and the solution was heated to 90° C. for 25 hr. The solution was concentrated under high vacuum and the residue was dissolved in ethyl acetate. The organic layer was washed with 1N NaOH, $H_2O$ and dried over $MgSO_4$. Chromatography on silica eluting with ethyl acetate/hexane provided trifluoromethoxy phenoxyphenyl sulfone as a light yellow gel (7.81 g, 91.5%).

Part C: To a solution of trifluoromethoxy phenoxyphenyl sulfone of Part B (7.81 g, 14.7 mmol) in ethanol (14 mL) and tetrahydrofuran (14 mL) was added NaOH (5.88 g, 147 mmol) in $H_2O$ (28 mL) from an addition funnel at ambient temperature. The solution was then heated to 60° C. for 18 hr. The solution was concentrated in vacuo and diluted with water. The aqueous layer was extracted with ether and acidified to pH=2. Vacuum filtration of white precipitation provided the acid as a white solid (5.64 g, 73.3%).

Part D: To a solution of the acid of Part C (5.64 g, 10.8 mmol), N-methyl morpholine (4.8 mL, 43.1 mmol), 1-hydroxybenzotriazole (4.38 g, 32.4 mmol) and O-tetrahydropyranyl hydroxyl amine (2.5 g, 21.6 mmol) in N,N-dimethylformamide (50 mL) was added 1-[3-(dimethylamino)propyl]-3-ethylcarbodiimide hydrochloride (6.2 g, 32.4 mmol), and the solution was stirred at ambient temperature for 24 hr. The solution was concentrated under high vacuum and the residue was dissolved in ethyl acetate. The organic layer was washed with saturated aqueous $NaHCO_3$, $H_2O$ and dried over $MgSO_4$. Concentration in vacuo and chromatography on silica eluting with ethyl acetate/hexane provided the tetrahydropyranyl-protected hydroxamate as a white foam (6.65 g, quantitative yield).

Part E: To a solution of 4N HCl in dioxane (28 mL, 110 mmol) was added a solution of the tetrahydropyranyl-protected hydroxamate of Part D (6.65 g, 11.03 mmol) in methanol (3 mL) and dioxane (9 mL) and was stirred at ambient temperature for 3 hr. Concentration in vacuo and trituration with diethyl ether provided the title compound as a white solid (4.79 g, 78.2%). Analytical calculation for $C_{22}H_{25}N_2O_7SF_3 \cdot HCl \cdot 0.5H_2O$: C, 46.85; H, 4.83; N, 4.97; S, 5.69. Found: C, 46.73; H, 4.57; N, 4.82; S, 5.77.

Preparative Example VIII

Preparation of N-hydroxy-1-[2-(4-morpholinyl)-ethyl]-4-[[4-[4-(trifluoromethyl)phenoxy]-phenyl]sulfonyl]-4-piperidinecarboxamide, dihydrochloride

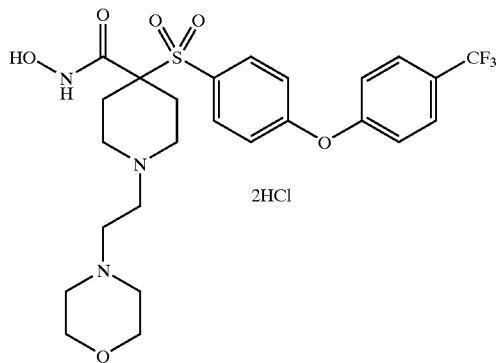

Part A: To a suspension of 4-bromopiperidine hydrobromide (107.0 g, 0.436 mol) in tetrahydrofuran (1 L) was slowly added triethylamine (122 mL, 0.872 mol) followed by di-tert-butyl dicarbonate (100 g, 0.45 8 mol), which was added in several portions. The resulting mixture was stirred at ambient temperature for 22 hr then filtered and concentrated in vacuo. The solids were washed with hexanes and then collected by filtration to give the Boc-piperidine compound as an amber oil (124 g, >100%).

Part B: To a solution of 4-fluorophenol (50.0 g, 0.390 mol) in acetone (400 mL), degassed with $N_2$, was added $Cs_2CO_3$ (159 g, 0.488 mol). After degassing the resulting mixture with $N_2$ for 5 min, the Boc-piperidine compound of Part A (85.9 g, 0.325 mol) was added. The resulting mixture was stirred at ambient temperature for 18 hr and then filtered through a pad of Celite®, washing with acetone. The filtrate was concentrated in vacuo to provide the sulfide as a tan residue (98.5 g, 97%).

Part C: To a solution of the sulfide of Part B (8.00 g, 25.7 mmol) in dichloromethane (90 mL) and methanol (15 mL) was added monoperoxyphthalic acid magnesium salt hexahydrate (19.1 g, 38.6 mmol) in two portions. The resulting mixture was stirred at ambient temperature for 1.5 hr and then filtered. The filtrate was washed with saturated $NaHCO_3$ and then with saturated NaCl. The combined aqueous layers were extracted with dichloromethane (100 mL). The combined organic layers were dried over $Na_2SO_4$ and then concentrated in vacuo. The resulting solids were washed with hexanes then dissolved in dichloromethane and filtered through a pad of Celite®, washing with dichloromethane. The filtrate was concentrated in vacuo and recrystallization from ethyl acetate provided the sulfone as a white crystalline solid (4.45 g, 50%).

Part D: To a solution of sulfone of Part C (7.00 g, 20.4 mmol) in N,N-dimethylformamide (40 mL) was added $Cs_2CO_3$ (19.9 g, 61.2 mmol) and α,α,α-trifluoro-p-cresol (3.97 g, 24.5 mmol). The resulting mixture was heated at 80° C. for 16 hr. After cooling to ambient temperature, the reaction mixture was concentrated in vacuo. The resulting residue was treated with $H_2O$ and the solids were collected by filtration. The solids were then washed with hexanes then methanol to provide the biaryl ether as a tan solid (8.60 g, 87%).

Part E: To a solution of the biaryl ether of Part D (8.59 g, 17.7 mmol) in tetrahydrofuran (100 mL), cooled to 0° C., was slowly added lithium bis(trimethylsilyl)amide (22.0 mL, 1.0 OM in tetrahydrofuran, 22.0 mmol), at such a rate that the temperature of the reaction never exceeded 1° C. The resulting mixture was stirred at 0° C. for 1 hr then a solution of methyl chloroformate (2.05 mL, 26.6 mmol) in tetrahydrofuran (5.0 mL) was slowly added, at such a rate that the temperature of the reaction mixture never exceeded 4° C. After the addition was complete, the mixture was slowly permitted to warm to ambient temperature. Saturated $NH_4Cl$ (50 mL) was added and the tetrahydrofuran was removed in vacuo. Water (50 mL) was added to the residue which was then extracted with ethyl acetate. The combined organic layers were washed with saturated NaCl and dried over $Na_2SO_4$. Recrystallization from methanol provided the methyl ester as a pale yellow crystalline solid (7.66 g, 80%).

Part F: To a solution of the methyl ester of Part E (7.66 g, 14.1 mmol) in dioxane (30 mL) and methanol (10 mL) was added a solution of 4N HCl in dioxane (10 mL, 40 mmol). After stirring at ambient temperature for 2 hr, additional 4N HCl in dioxane (10 mL, 40 mmol) was added. After stirring at ambient temperature for 2.5 hr, the reaction mixture was concentrated in vacuo to provide the amine as an off-white solid (6.80 g, >100%).

Part G: To a suspension of the amine of Part F (3.00 g, 6.25 mmol) in acetonitrile (20 mL) was added $K_2CO_3$ (3.46 g, 25.0 mmol), 4-(2-chloroethyl)morpholine hydrochloride (1.22 g, 6.56 mmol) and a catalytic amount of NaI. The resulting mixture was heated at reflux for 22 hr. After cooling to ambient temperature, the reaction mixture was filtered through a pad of Celite®, washing with ethyl acetate. The filtrate was concentrated in vacuo to provide the morpholinyl ethyl amine as a tan solid (3.45 g, >100%).

Part H: To a solution of the morpholinyl ethyl amine of Part G (3.45 g, 6.25 mmol) in tetrahydrofuran (60 mL) was added potassium trimethylsilanolate (1.60 g, 12.50 mmol). After stirring at ambient temperature for 25 hr, H₂O was added. The reaction mixture was then neutralized (pH 7) with 1N HCl. The tetrahydrofuran was removed in vacuo and the resulting precipitate was collected by filtration and washed with diethyl ether to provide the amino acid as an off-white solid (2.87 g, 85%).

Part I: To a suspension of the amino acid of Part H (2.87 g, 5.29 mmol) in dichloromethane (25 mL) was added N-methylmorpholine (1.74 mL, 15.9 mmol), O-(tetrahydropuranyl) hydroxylamine (0.682 g, 5.82 mmol) and PyBroP® (2.96 g, 6.35 mmol). After stirring at ambient temperature for 19 hr, additional N-methylmorpholine (0.872 mL, 7.94 mmol), O-(tetrahydropuranyl) hydroxylamine (0.310 g, 2.65 mmol) and PyBroP® (1.48 g, 3.17 mmol) were added. The resulting mixture was stirred at ambient temperature for 3 hr and then concentrated in vacuo. The residue was partitioned between ethyl acetate and H₂O. The organic layers were washed with saturated NaCl and dried over Na₂SO₄. Chromatography (on silica, methanol/chloroform) provided the protected hydroxamate as an off-white solid (2.62 g, 77%).

Part J: To a solution of the protected hydroxamate of Part I (2.62 g, 4.08 mmol) in dioxane (9 mL) and methanol (3 mL) was added a solution of 4N HCl in dioxane (10 mL, 40.0 mmol). The resulting mixture was stirred at ambient temperature for 2 hr and then diethyl ether (20 mL) was added. The resulting solids were collected by filtration to give the title compound as an off-white solid (2.31 g, 90%). MS MH⁺ calculated for $C_{25}H_{31}O_6N_3SF_3$: 558, found 558.

Preparative Example IX

Preparation of 1-cyclopropyl-N-hydroxy-4-[[4-[4-(trifluoromethoxy)phenoxy]-phenyl]sulfonyl]-4-piperidine-carboxamide, monohydrochloride

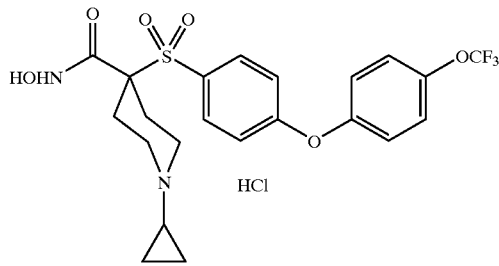

Part A: To a solution of the product of Preparative Example VI, Part A, (6.97 g, 19.6 mmol) in DMF (500 mL) was added K₂CO₃ (3.42 g, 18.0 mmol) and 4-(triflouromethoxy)phenol (3.7 g, 24.8 mmol). The solution was stirred at 90° C. for 40 hr. The solution was diluted with H₂O (600 mL) and extracted with ethyl acetate. The organic layer was washed with water, saturated NaCl and dried over MgSO₄, filtered and concentrated in vacuo to afford the desired diaryl ether as an oil (8.5 g, quantitative). HRMS MH⁺ calculated for $C_{24}H_{26}NSO_6F_3$: 514.1511. Found 514.1524.

Part B: To a solution of diaryl ether from Part A (8.4 g, 16.4 mmol) in ethanol (50 mL) and tetrahydrofuran (50 mL) was added a solution of NaOH (6.54 g, 164 mmol) in water (20 mL) and the solution was heated at 60° C. for 18 hr. The solution was concentrated in vacuo to remove most of organic solvents and the aqueous residue was acidified to pH=4.0. The resulting precipitate was filtered to give the desired filtered to give the hydrochloride salt as a white solid (5.01 g, 63%). HRMS MH⁺ calculated for $C_{22}H_{22}NSO_6F_3$: 486.1198, found 486.1200.

Part C: To a solution of the hydrochloride salt of Part B (5.0 g, 10.3 mmol) in DMF (80 mL) were added 1-hydroxybenzotriazole (1.65 g, 12.3 mmol), N-methyl morpholine (3.4 mL, 30.9 mmol) and O-tetrahydropyranyl hydroxylamine hydrochloride (1.8 g, 15.4 mmol) followed by 1-3-(dimethylamino)propyl]-3-ethylcarbodiimide hydrochloride (1.60 g, 12.3 mmol). The solution was stirred at ambient temperature for 42 hr. The solution was diluted with H₂O (400 mL) and extracted with ethyl acetate. The organic layer was washed with saturated NaCl and dried over MgSO₄, filtered and concentrated in vacuo. Chromatography on silica gel, eluting with 30% ethyl acetate/hexane provided the desired tetrahydropyranyl-protected hydroxamate as a white solid (5.41 g, 89%).

Part D: To a solution of tetrahydropyranyl-protected hydroxamate of Part C (5.4 g, 9.2 mmol) in dioxane (80 mL) and methanol (20 mL) was added 4 N HCl/dioxane (50 mL). The reaction was stirred at ambient temperature for 2.5 hr, the solution was concentrated in vacuo. Trituration with diethyl ether afforded the title compound as a white solid (4.02 g, 81%). HRMS MH⁺ calculated for $C_{22}H_{23}N_2SO_6F_3$: 501.1307, found 501.1324.

Preparative Example X

Preparation of 1-cyclopropyl-N-hydroxy-4-[[4-[4-(trifluoromethyl)phenoxy]phenyl]sulfonyl]-4-piperidinecarboxamide, monohydrochloride

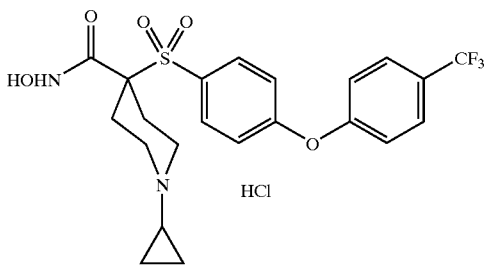

Part A: To a solution of the product of Preparative Example VI, Part A, (5.96 g, 15.0 mmol) in DMF (100 mL) was added K₂CO₃ (12.34 g, 38.0 mmol) and □□□-trifluoromethyl phenol (3.65 g, 22.5 mmol). The solution was stirred 90° C. for 28 hr. The solution was diluted with H₂O (400 mL) and extracted with ethyl acetate. The organic layer was washed with water, saturated NaCl and dried over MgSO₄, filtered and concentrated in vacuo to afford desired aryl ether as an oil (7.54 g, quantitative)

Part B: To a solution of aryl ether from Part A (7.54 g, 15.0 mmol) in ethanol (4 0 mL) and tetrahydrofuran (40 mL) was added a solution of NaOH (6.06 g, 151.0 mmol) i n water (20 mL) and the solution was heated at 60° C. for 18 hr. The solution was concentrated in vacuo and the aqueous residue was acidified to pH=2.0. The resulting precipitate was filtered to give the desired hydrochloride salt as a white solid (7.98 g, quantitative). MS MH⁺ calculated for $C_{22}H_{22}NSO_5F_3$: 470, found 470.

Part C: To a solution of the hydrochloride salt of Part B (7.60 g, 15.0 mmol) in DMF (100 mL) were added 1-hydroxybenzotriazole (2.44 g, 18.0 mmol), N-methyl morpholine (3.4 mL, 30.9 mmol ) and O-tetrahydropyranyl hydroxyl amine hydrochloride (2.63 g, 22.5 mmol) followed by 1-3-(dimethylamino)propyl]-3-ethylcarbodiimide hydrochloride (4.02 g, 21.0 mmol). The solution was stirred at ambient temperature for 96 hr. The solution was diluted with H$_2$O (400 mL) and extracted with ethyl acetate. The organic layer was washed with saturated NaCl and dried over MgSO$_4$, filtered and concentrated in vacuo. Chromatography on silica eluting with 30% ethyl acetate/hexane provided the desired tetrahydropyranyl-protected hydroxamate as a white solid (5.93g, 69%).

Part D: To a solution of tetrahydropyranyl-protected hydroxamate of Part C (3.8 g, 6.7 mmol) in dioxane (100 mL) was added 4N HCl/dioxane (30 mL). The reaction was stirred at ambient temperature for 2 hr, then the solution was concentrated in vacuo. Trituration with diethyl ether afforded the title compound as a white solid (3.33 g, 96%). MS MH$^+$ calculated for $C_{22}H_{23}N_2SO_5F_3$: 485, found 485.

Preparative Example XI

Preparation of Resin II

Step 1: Attachment of Compound of Preparative Example IV to Resin I

A 500 mL round-bottomed flask was charged with of resin I [Floyd et al., *Tetrahedron Lett.* 1996, 37, 8045–8048] (8.08 g, 9.7 mmol) and 1-methyl-2-pyrrolidinone (50 mL). A magnetic stirring bar was added, and the resin slurry slowly stirred. A separate solution of the compound of Part D, Preparative Example IV (5.58 g, 19.4 mmol) in 1-methyl-2-pyrrolidinone (35 mL) was added to the slurry followed by addition of benzotriazole-1-yl-oxy-tris-pyrrolidino-phosphonium hexafluorophosphate (10.1 g, 19.4 mmol) in one portion. Once the hexafluorophosphate salt had dissolved, 4-methylmorpholine (4.26 mL, 39 mmol) was added dropwise. The reaction slurry was stirred at room temperature for 24 hr, then the resin was collected in a sintered-disc funnel and washed with N,N-dimethylformamide, methanol, methylene chloride and diethyl ether (3×30 mL each solvent). The resin was dried in vacuo to yield 10.99 g polymer-bound hydroxymate as a tan polymeric solid. Theoretical loading on polymer was 0.91 mmol/g. FTIR microscopy showed bands at 1693 and 3326 cm$^{-1}$ indicative of the hydroxamate carbonyl and nitrogen-hydrogen stretches, respectively.

Step 2: Preparation of Resin III

Reaction of Resin II With Nucleophiles

Resin II (50 mg, 0.046 mmol) was weighed into an 8 mL glass vial, and a 0.5 M solution of a nucleophile in 1-methyl-2-pyrrolidinone (1 mL) was added to the vessel. In the case of phenol and thiophenol nucleophiles, cesium carbonate (148 mg, 0.46 mmol) was added, and in the case of substituted piperazine nucleophiles, potassium carbonate (64 mg, 0.46 mmol) was added. The vial was capped and heated to 70 to 155° C. for 24–48 hr, then cooled to room temperature. The resin was drained and washed with 1-methyl-2-pyrrolidinone, 1-methyl-2-pyrrolidinone/water (1:1), water, 10% acetic acid/water, methanol, and methylene chloride (3×3 mL each solvent).

Large Scale Preparation of Resin IIIa

Resin II (5 g, 0.91 mmol) was weighed into an oven-dried three-necked round bottom flask fitted with a temperature probe, an overhead stirring paddle, and a nitrogen inlet. Anhydrous 1-methyl-2-pyrrolidinone (35 mL) was added to the flask followed by ethyl isonipecotate (7.0 mL, 45.5 mmol). The resin slurry was stirred slowly with the overhead stirrer, and the mixture was heated to 80° C. with a heating mantle for 65 hr. The flask was thereafter cooled to room temperature.

The resin was collected in a sintered-disk glass funnel and washed with N,N-dimethylformamide, methanol and methylene chloride (3×30 mL each solvent). The resin was dried in vacuo to provide 5.86 g of resin IIIa as off-white resin beads. The theoretical loading of the polymer was 0.81 mmol/g. TFA cleavage performed on 50 mg of resin IIIa as described in step 3 yielded 10.4 mg of off-white solid spectroscopically indistinguishable from a known sample.

Step 3: Cleavage of Hydroxamic Acids from the Polymer-Support

Resin III was treated with a trifluoroacetic acid/water mixture (19:1, 1 mL) for 1 hr at room temperature. During that time, the resin became a deep red color. The resin was then drained and washed with trifluoroacetic acid/water (19:1) and methylene chloride (2×1 mL each solvent), collecting the combined filtrates in a tared vial. The volatiles were removed in vacuo, then a toluene/methylene chloride mixture (2 mL each) was added to the residue. The mixture was again concentrated in vacuo. The product was characterized by electrospray mass spectroscopy.

Step 4: Hydrolysis of Polymer-Bound Ester: Preparation of Resin IVa

Resin IIIa (5.8 g, 4.5 mmol) was weighed into a three-necked round bottomed flask fitted with an overhead stirring paddle. 1,4-Dioxane was added to the flask, and the resin slurry was stirred for 15 min. Then, a 4 M solution of KOH (5 mL, 20 mmol) was added, and the mixture was stirred for 44 hr. The resin was thereafter collected in a sintered-disk glass funnel and washed with dioxane/water (9:1), water, 10% acetic acid/water, methanol and methylene chloride (3×30 mL each solvent). The resin was dried in vacuo to yield 5.64 g of resin IVa as off-white polymer beads. FTIR microscopy showed bands at 1732 and 1704 cm$^{-1}$ and a broad band from 2500–3500 cm$^{-1}$. The theoretical loading of the polymer-bound acid was 0.84 mmol/g.

Examples 1–45

The following compounds were prepared by parallel synthesis (resin based synthesis, automated synthesis) using parallel synthesis from Resin IVa as described previously in Preparative Example XI the following compounds were prepared:

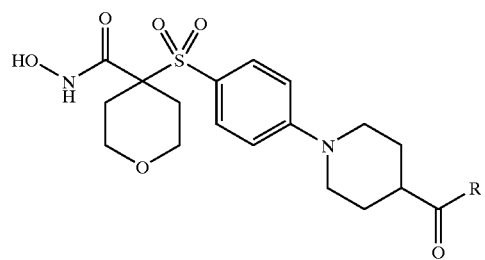

| Example | Amine | R | MS (M + H) |
|---|---|---|---|
| 1 | 3,5-Dimethylpiperidine | 3,5-dimethylpiperidin-1-yl | 508 |
| 2 | 1-(1-phenylethyl)-piperazine | 4-(2-phenylethyl)piperazin-1-yl, TFA | 585 |
| 3 | 1(2-phenylethyl)-piperazine | 4-(1-phenylethyl)piperazin-1-yl, TFA | 585 |
| 4 | 1-(2-chlorophenyl)-piperazine | 4-(2-chlorophenyl)piperazin-1-yl | 591 |
| 5 | 1-(4-methoxyphenyl)-2-methylpiperazine | 4-(4-methoxyphenyl)-3-methylpiperazin-1-yl | 585 |
| 6 | 1-(5-Chloro-2-methylphenyl)piperazine | 4-(5-chloro-2-methylphenyl)piperazin-1-yl | 605 |
| 7 | 1-(2-methoxyphenyl)-piperazine | 4-(2-methoxyphenyl)piperazin-1-yl | 587 |
| 8 | 1-Acetylpiperazine | 4-acetylpiperazin-1-yl | 523 |

-continued

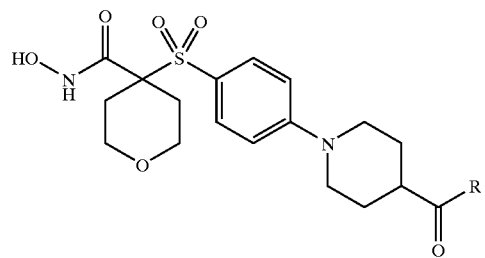

| Example | Amine | R | MS (M + H) |
|---|---|---|---|
| 9 | 1-(2,4-Dimethylphenyl)-piperazine | piperazine-2,4-dimethylphenyl | 585 |
| 10 | N-(2-hydroxyethyl)-piperazine | piperazine-CH2CH2OH, TFA | 525 |
| 11 | 1-(Ethoxy-carbonylmethyl)-piperazine | piperazine-CH2C(O)OEt, TFA | 567 |
| 12 | 1-(2-Fluorophenyl)-piperazine | piperazine-2-fluorophenyl | 575 |
| 13 | 1-(2-Furoyl)-piperazine | piperazine-C(O)-2-furyl | 575 |
| 14 | 1-(Cyclopentyl)-piperazine | piperazine-cyclopentyl, TFA | 549 |
| 15 | 1-(2-Propyl)-piperazine | piperazine-isopropyl, TFA | 523 |
| 16 | N-(2-(1-Piperazino)-acetyl)pyrrolidine | piperazine-CH2C(O)-pyrrolidine, TFA | 592 |
| 17 | 1-(3-Dimethyl-aminopropyl)-piperazine | piperazine-(CH2)3NMe2, TFA | 566 |

-continued

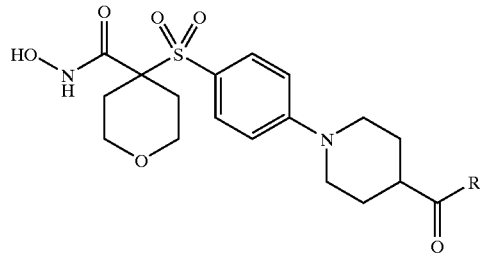

| Example | Amine | R | MS (M + H) |
|---|---|---|---|
| 18 | 1-(2-Methoxyethyl)-piperazine | piperazine-CH2CH2-O-CH3, TFA | 539 |
| 19 | 1-(2-Dimethyl-aminoethyl)-piperazine | piperazine-CH2CH2-N(CH3)2, TFA, TFA | 552 |
| 20 | 1-(2-Ethoxyphenyl)-piperazine | piperazine-(2-ethoxyphenyl) | 601 |
| 21 | 1-(4-Fluorphenyl)-piperazine | piperazine-(4-fluorophenyl) | 575 |
| 22 | 1-(2-Pyridyl)-piperazine | piperazine-(2-pyridyl) | 558 |
| 23 | 2-(1-piperazinyl)-pyrimidine | piperazine-(2-pyrimidyl) | 559 |
| 24 | 4-Piperazino-acetophenone | piperazine-(4-acetylphenyl) | 599 |
| 25 | 1-(4-Nitrophenyl)-piperazine | piperazine-(4-nitrophenyl) | 602 |
| 26 | 1-(3,5-Dichloropyrid-4-yl)piperazine | piperazine-(3,5-dichloropyrid-4-yl) | 626 |

-continued
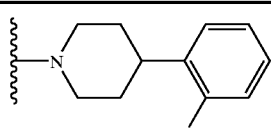
| Example | Amine | R | MS (M + H) |
|---|---|---|---|
| 27 | 4-(2-Methoxyphenyl)-piperidine | 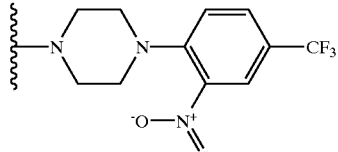 | 586 |
| 28 | N-[2-Nitro-4-(trifluoromethyl)-phenyl]piperazine | 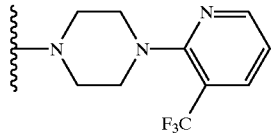 | 670 |
| 29 | 1-[3-(Trifluormethyl)-pyrid-2-yl]-piperazine | 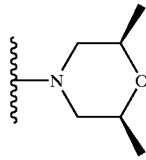 | 626 |
| 30 | cis-3,5-Dimethyl-morpholine | 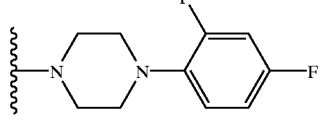 | 510 |
| 31 | 1-(2,4-Difluorphenyl)-piperazine | 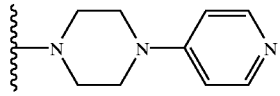 | 593 |
| 32 | 1-(4-Pyridyl)-piperazine | 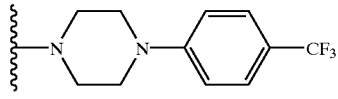 | 558 |
| 33 | 1-(4-Trifluoromethyl-phenyl)-piperazine | 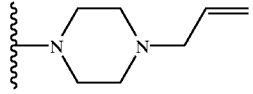 | 625 |
| 34 | 1-Allylpiperazine | TFA 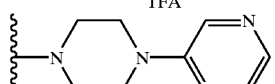 | 521 |
| 35 | 1-(2-Pyrazinyl)-piperazine | TFA | 559 |

-continued

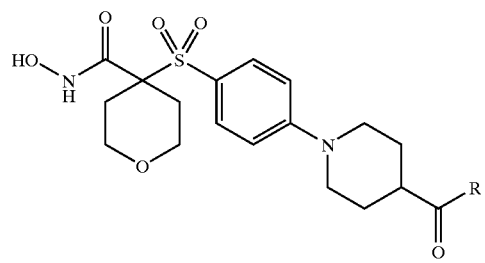

| Example | Amine | R | MS (M + H) |
|---|---|---|---|
| 36 | 1-[3-Chloro-5-(trifluoromethyl)pyrid-2-yl)]piperazine | piperazine linked to 3-chloro-5-(trifluoromethyl)pyrid-2-yl | 660 |
| 37 | 1-(2-(4-Morpholino)-ethyl)piperazine | piperazine-CH₂CH₂-morpholine, TFA | 594 |
| 38 | 3-Chlorophenyl-piperazine | piperazine linked to 3-chlorophenyl | 591 |
| 39 | 4-(Hydroxymethyl)-piperidine | piperidine-CH₂OH | 510 |
| 40 | cis-2,6-Dimethyl-piperazine | cis-2,6-dimethylpiperazine, TFA | 509 |
| 41 | 3-Methylpiperidine | 3-methylpiperidine | 494 |
| 42 | 1-[4-(Trifluormethyl)-2-pyrimidyl]-piperazine | piperazine linked to 4-(trifluoromethyl)-2-pyrimidyl | 627 |
| 43 | 1-[4-(Trifluormethyl)-2-pyridyl]-piperazine | piperazine linked to 4-(trifluoromethyl)-2-pyridyl | 626 |

-continued

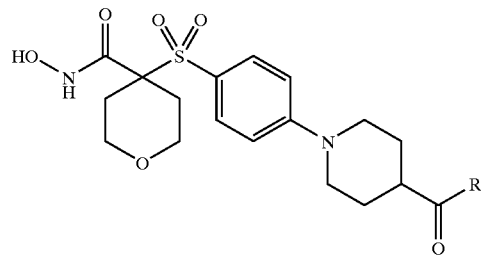

| Example | Amine | R | MS (M + H) |
|---|---|---|---|
| 44 | 3,5-Dimethyl-piperidine | (3,5-dimethylpiperidinyl, cis) | 508 |
| 45 | 3,5-Dimethyl-piperidine | (3,5-dimethylpiperidinyl, trans) | 508 |

Examples 46–47

Step 12: Further Synthesis of Resin III

Into a 8 mL glass vial was placed resin II (200 mg, 0.18 mmol) and cesium carbonate (0.98 g mg, 3 mmol) (no cesium carbonate used with piperidine and pyrrolidine nucleophiles). One mL of a 1.8 M solution of the amine nucleophile to be reacted in 1-methyl-2-pyrrolidinone (1.8 mmol) was added and the vial was capped and heated to 100° C. for 30 hr. Then the vessel was cooled to room temperature, and the resin was drained and washed with 1-methyl-2-pyrrolidinone, 1:1 1-methyl-2-pyrrolidinone/water, water, 1:9 acetic acid/water, methanol and methylene chloride (3×3 mL each solvent).

The following hydroxamic acids were synthesized from Resin III with the indicated amines, followed by release from the polymer using the reaction conditions in Step 3.

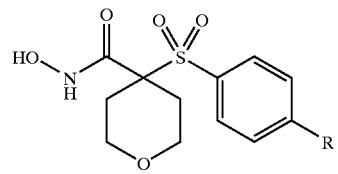

| Example | Amine | R | MS (M + H) |
|---|---|---|---|
| 46 | 1-(2-Methoxyphenyl)-piperidine | (4-(2-methoxyphenyl)piperidinyl) | 475 |

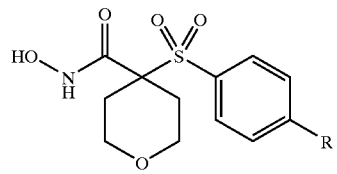

| Example | Amine | R | MS (M + H) |
|---|---|---|---|
| 47 | 4-(4-Methoxybenzoyl)-piperidine | (4-methoxybenzoyl-piperidinyl group) | 503 |

Example 48

Preparation of N-hydroxy-4-[[4-(4-methoxyphenoxy)phenyl]sulfonyl]-4-thianecarboxamide

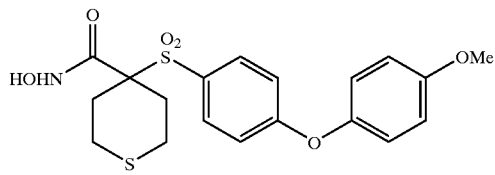

Step 1: Hydrolysis of methyl 4-[[4-(4-methoxyphenoxy)phenyl]sulfonyl]-4-thianecarboxylate. To a solution of methyl 4-[[4-(4-methoxyphenoxy)-phenyl]sulfonyl]-4-thianecarboxylate (10.0 g, 31 mmol) dissolved in tetrahydrofuran (150 mL) was added potassium trimethylsilanolate (12.1 g) and stirred 2 hr. Water was added to the reaction mixture and extracted with ethyl acetate (2×100 mL). The pH value of the aqueous layer was adjusted to 2 with 2M hydrochloric acid and extracted with ethyl acetate (2×100 mL). The latter organics were washed with brine, dried over magnesium sulfate, filtered and the solvent evaporated to afford a pale yellow solid (8.20 g).

Step 2: Loading on resin. The compound obtained in step 1 (4.0 g, 13.1 mmol) was dissolved in 1-methyl-2-pyrrolidinone (15 mL) and added to a suspension of resin I (6.0 g, 6.6 mmol; Preparative Example XI) in 1-methyl-2-pyrrolidinone (40 mL). To this solution were added pyBOP (6.85 g) and N-methylmorpholine (2.9 mL), and the mixture was stirred with overhead stirring 16 hr. The resin was filtered and washed with dimethylformamide (3×50 mL), methanol (3×50 mL), dichloromethane (3×50 mL) and ether (3×50 mL). The resin was dried in vacuo to provide resin MT-III (6.79 g).

Step 3: Aryl fluoride displacement of resin MT-III. A suspension of resin MT-III (200 mg, 0.17 mmol), 1-methyl-2-pyrrolidinone (2 mL), cesium carbonate (560 mg) and 4-methoxyphenyl (306 mg) were stirred at 105° C. for 16 hr. The reaction mixture was cooled and the resin filtered. The resin was washed with dimethylformamide (3×5 mL), methanol (3×5 mL), 10% aqueous acetic acid (3×5 mL), methanol (3×5 mL) and dichloromethane (3×5 mL). To the resin was added 95% aqueous trifluoroacetic acid and the reaction mixture was agitated for 1 hr. The resin was drained and washed with dichloromethane (2×1 mL). The solvent was evaporated. The residue was purified by RPHPLC to provide N-hydroxy-4-[[4-(4-methoxy-phenoxy)phenyl]sulfonyl]-4-thianecarboxamide (17.9 mg) as a pale yellow oil.

Examples 49–50

The following hydroxamic acids were prepared by the method of Example 48 using the appropriate amine.

| Example | R | Amine | MS (ES) m/z |
|---|---|---|---|
| 49 | 4-(4-fluoro-benzoyl)piperidyl | 4-(4-fluorobenzoyl)-piperidine | 504 (M + H)+ |
| 50 | 4-(2-methoxy-phenyl)piperidyl | 4-(2-methoxyphenyl)-piperidine | 491 (M + H)+ |

Example 51

Preparation of N-hydroxy-4-[[4-(4-methoxyphenoxy)phenyl]sulfonyl]-4-thianecarboxamide-1,1-dioxide

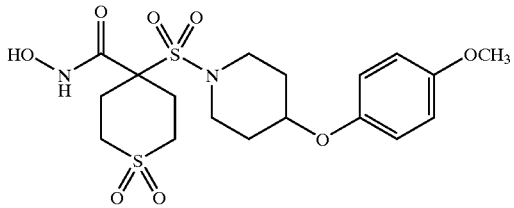

Step 1: Oxidation of Resin MT-III. A suspension of resin MT-III (2.0 g, 1.72 mmol), m-chloroperbenzoic acid (4.37 g) and dichloromethane (25 mL) was stirred at room temperature for 20 hr. The resin was filtered and washed with dichloromethane (3×25 mL), dimethylformamide (3×25 mL), methanol (3×25 mL), 1M aqueous sodium bicarbonate (2×25 mL), methanol (3×25 mL), dichloromethane (3×25 mL) and ether (3×25 mL). The resin was dried in vacuo to afford resin MT-IV (2.16 g).

Step 2: Aryl fluoride displacement of resin MT-IV. N-hydroxy-4-[[4-(4-methoxyphenoxy)-phenyl]sulfonyl]-4-thianecarboxamide 1,1-dioxide was prepared by the method of Example 48 using resin MT-IV in the place of resin MT-III. ES (MS) m/z 473 (M+NH$_4$)$^+$.

Example 52

The following hydroxamic acid was prepared by the method of Example 51 using 4-(4-fluoro-benzoyl)-piperidine as the amine. MS (ES) m/z 539 (M+H)$^+$.

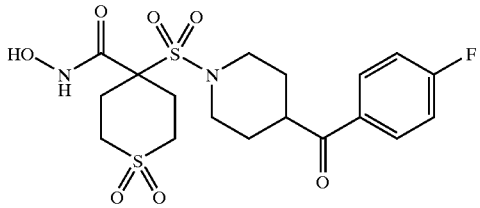

Example 53

Preparation of N-hydroxy-4-[[4-[4-[(3,5-dimethylpiperidyl)carbonyl]-piperidyl]phenyl]sulfonyl]-4-thianecarboxamide

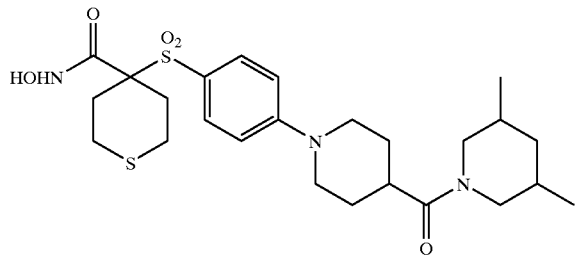

Step 1: Aryl fluoride displacement of Resin MT-III. To a suspension of resin MT-III (4.06 g, 3.4 mmol) in 1-methyl-2-pyrrolidinone (40 mL) was added ethyl isonipecotate (5.25 mL), and the mixture was heated to 100° C. for 16 hr. The cooled reaction mixture was filtered and the resin was washed with methanol (3×25 mL), dichloromethane (×10 mL) and ether (3×25 mL). The resin was dried in vacuo to afford resin MT-V (4.21 g).

Step 2: Hydrolysis of resin MT-V. To a suspension of resin MT-V (4.13 g) in tetrahydrofuran (20 mL) was added 4M aqueous potassium hydroxide (10 mL) and stirred at room temperature for 5 days. The resin was filtered and washed with methanol (3×25 mL), dichloromethane (3×25 mL) and ether (3×25 mL). The resin was dried in vacuo to afford resin MT-VI.

Step 3: Conversion to amide. To a suspension of resin MT-VI (268 mg) in 1-methyl-2-pyrrolidinone (2 mL) were added 3,5-dimethyl-piperidine (299 μL), pyBOP (587 mg) and diisopropylethyl amine (393 μL), and mixture was stirred 40 hr. The resin was filtered and washed with dimethylformamide (3×2 mL), methanol (3×2 mL), 10% aqueous acetic acid (3×2 mL), methanol (3×2 mL), dichloromethane (3×2 mL) and glacial acetic acid (1×2 mL). The resin was treated with 95% aqueous trifluoroacetic acid (2 mL) and agitated 1 hr. The resin was washed with dichloromethane (2 mL) and methanol (2 mL). The filtrate was evaporated. The residue was purified by RPHPLC to afford N-hydroxy-4-[[4-[4-[(3,5-dimethylpiperidyl)carbonyl]piperidyl]phenyl]sulfonyl]-4-thianecarboxamide (7.5 mg) MS (ES) m/z 524 (M+H)$^+$.

Example 54

Preparation of 1,1-dimethylethyl-3,6-dihydro-4-[2-(trifluoromethyl)phenyl]-1(2H)-pyridinecarboxylate

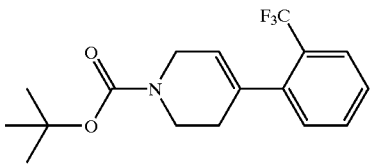

Part A: An oven-dried 1.0 liter flask fitted with a thermometer and nitrogen inlet was charged with 55 mL of a 2 M solution of lithium diisopropoylamide in tetrahydrofuran and 50 mL of tetrahydrofuran. The flask was immersed in a dry ice/acetone bath. When the temperature of the solution was less than −70° C., a solution of N-t-butoxycarbonylpiperidinone (20.0 g, 0.1 mole) in 100 mL tetrahydrofuran was added dropwise, maintaining the temperature less than −65° C. After complete addition, the flask was stirred with cooling for 20 min. Then a solution of N-trifluoromethanesulfonimide (38.2 g, 0.107 mole) was added dropwise maintaining the temperature less than −65° C. After complete addition, the dry ice/acetone bath was swapped with an ice/water bath. The reaction was stirred overnight (about 18 hr), slowly warming to room temperature. After 16 hr, the solvent was removed in vacuo, and the residue was purified by column chromatography on neutral alumina, yielding 26.53 g of product as a yellow oil. Electrospray mass spectroscopy showed m/z 332 (M+H).

Part B: A three-necked 15 mL round-bottom flask was charged with the product from Part A (6 g, 18.1 mmol), o-trifluorobenzeneboronic acid (4.94 g, 26 mmol), lithium chloride (2.34 g, 55 mmol), 2 M sodium carbonate (26 mL, 52 mmol) and ethylene glycol dimethyl ether (60 mL). Nitrogen was bubbled through the solution for 10 min, then palladium tetrakistriphenylphosphine (1.06 g, 0.92 mmol)

was added. The mixture was heated to reflux for 1.5 hr, then cooled to room temperature. The solvent was removed in vacuo, then the residue was partitioned between 100 mL of methylene chloride and 100 mL of 2 M sodium carbonate with 3 mL concentrated ammonium hydroxide. The aqueous layer was extracted with an additional 100 mL methylene chloride, then the combined organic layers were dried over magnesium sulfate and concentrated to give 8.42 g of crude product as a dark brown oil. Purification via flash column chromatography (10% ethyl acetate3/hexanes) yielded 2.76 g of pure product as a yellow oil. Electrospray mass spectroscopy showed m/z 328 (M+H).

Example 55

Preparation of 1,2,3,6-tetrahydro-4-[2-(trifluoromethyl)phenyl]pyridine

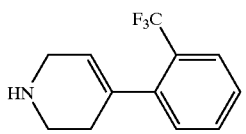

The title compound of Example 54 (300 mg, 0.92 mmol) was dissolved in methylene chloride (5 mL) in a 15 mL round-bottom flask, and 5 mL of trifluoroacetic acid was added dropwise. After 15 min, the solvent was removed in vacuo, and the residue partitioned between 20 mL of ethyl acetate and 20 mL of 2 M sodium carbonate. The organic layer was washed with additional 2 M sodium carbonate, dried over magnesium carbonate and concentrated in vacuo to yield 195 mg of pure product as a colorless oil. Electrospray mass spectroscopy showed m/z 228 (M+H).

Example 56

Preparation of 4-[2-(trifluoromethyl)phenyl]piperidine

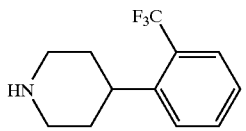

Part A: A solution of the title compound of Example 54 (2.3 g, 7 mmol) in 20 mL ethanol was added to a hydrogenation flask containing 1 g of 4% palladium on carbon (0.38 mmol). The mixture was placed under 100 PSI hydrogen and heated to 50° C. for 5 hr. Then the mixture was cooled to room temperature and filtered through Celite. The filtrate was concentrated in vacuo to give 2.27 g of pure product as a colorless oil. Electrospray mass spectroscopy showed m/z 330 (M+H).

Part B: The product from Part A above (2.24 g, 6.8 mmol) was dissolved in 100 mL methylene chloride, and 100 mL of trifluoroacetic acid was added dropwise. After 15 min, the solvent was removed in vacuo, and the residue partitioned between 100 mL of ethyl acetate and 100 mL of 2 M sodium carbonate. The organic layer was washed with additional 2 M sodium carbonate, dried over magnesium carbonate and concentrated in vacuo to yield 1.12 g of pure product as a colorless oil. Electrospray mass spectroscopy showed m/z 230 (M+H).

Example 57

General Description for Preparation of Hydroxamic Acids via Aryl Fluoride Displacement with Amines Part A: A 2 dram vial was charged with aryl fluoro compound of Preparative Example IV (170 mg, 0.44 mmol), 1 ml of 2-methylpyrrolidinone, cesium carbonate (360 mg, 1.1 mmol) and 0.66 mmol of an amine. A small magnetic stirring bar was added, then the vial was capped and placed in a Pierce Reacti-therm™ at 115° C. The reaction progress was followed by analytical HPLC. When the reaction was greater than 90% complete, the vial was cooled to room temperature. The reaction mixture was diluted with 5 mL of water, then 1.2 mL of 5% hydrogen chloride/water was added dropwise. Then, the entire mixture was poured onto a column of Celite. The column was washed exhaustively with ethyl acetate (30–40 mL) and the filtrate was collected and concentrated to give the crude products.

Part B: The product from above was dissolved in 2 mL 1,4-dioxane and 2 mL of methanol in a 4 dram vial with a small magnetic stirring bar. A solution of 4 N hydrogen chloride in 1,4-dioxane was carefully added to the reaction, and the mixture was stirred for 2 hr. Then the solvent was removed in vacuo and the residue purified by preparative reversed-phase HPLC.

Examples 58–60

The following hydroxamic acids were prepared using the method described above in Example 57 with the indicated amine as the starting material.

| Example | amine | R | | m/z from electrospray mass spectroscopy |
|---|---|---|---|---|
| 58 | Product of Example 56 | | F₃C-phenyl-piperidinyl | 513.3 (M + H) |
| 59 | Product of Example 55 | | F₃C-phenyl-tetrahydropyridinyl | 511.2 (M + H) |
| 60 | 4-(2-keto-benzimidazolinyl)-piperidine | | 2-keto-benzimidazolinyl-piperidinyl | 501 (M + H) |

Examples 61–69

Using the procedures outlined in Examples 54, 55, and 57 and other methods outlined above, the following analogs are made from the indicated boronic acid:

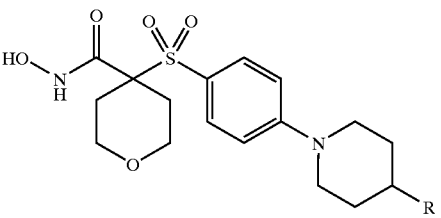

| Example | Boronic acid | R |
|---|---|---|
| 61 | 2-(trifluoromethoxy)phenyl B(OH)₂ | 2-(trifluoromethoxy)phenyl |
| 62 | 2-ethoxyphenyl B(OH)₂ | 2-ethoxyphenyl |
| 63 | 2-fluorophenyl B(OH)₂ | 2-fluorophenyl |
| 64 | 2,4-difluorophenyl B(OH)₂ | 2,4-difluorophenyl |
| 65 | 2-chlorophenyl B(OH)₂ | 2-chlorophenyl |
| 66 | 2,4-dichlorophenyl B(OH)₂ | 2,4-dichlorophenyl |
| 67 | 2,4-dimethoxyphenyl B(OH)₂ | 2,4-dimethoxyphenyl |
| 68 | 2-(trifluoromethoxy)-4-(trifluoromethoxy)phenyl B(OH)₂ | 2-(trifluoromethoxy)-4-(trifluoromethoxy)phenyl |
| 69 | 2,4-bis(trifluoromethyl)phenyl B(OH)₂ | 2,4-bis(trifluoromethyl)phenyl |

Example 70

Preparation of 4-[[4-[4-[(3,5-dimethyl-1-piperidinyl)carbonyl]-1-piperidinyl]-phenyl]sulfonyl]-N-hydroxy-1-(2-methoxyethyl)-4-piperidinecarboxamide, monohydrochloride

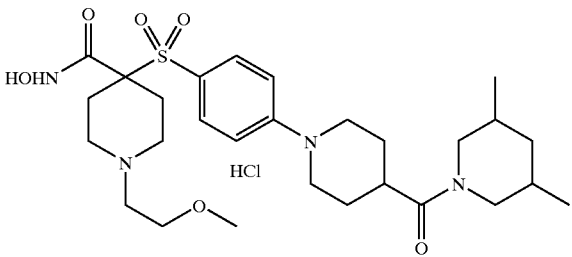

Part A: To a solution of isonipecotic acid (5.8 g, 44.9 mmol) in water (200 mL) was added sodium carbonate (4.62 g, 44.9 mmol) followed by the drop-wise addition of di-tert-butyl-dicarbonate (10.1 g, 46.3 mmol) in dioxane (40 mL). After 4 hr, the solvent was concentrated in vacuo and the solution was extracted with ethyl ether. The aqueous layer was acidified with 3N hydrochloric acid to pH=2. The solution was extracted with ethyl ether and the organic layer was washed with saturated aqueous sodium chloride and dried over magnesium sulfate. Concentration in vacuo provided N-Boc-isonipecotic acid as a white solid (9.34 g, 90%).

Part B: To a solution of the N-Boc-isonipecotic acid of part A (1.0 g, 4.37 mmol) in dichloromethane (10 mL) was added 1-[3-(dimethylamino)propyl]-3-ethylcarbodiimide hydrochloride (853 mg, 4.45 mmol), 1-hydroxybenzotriazole hydrate (620 mg, 4.59 mmol) 3,5- dimethylpiperdine (0.67 mL, 5.03 mmol) and diisopropylethylamine (1.67 mL, 9.61 mmol) and was stirred for 21 hr. The solution was concentrated in vacuo. The residue was diluted with ethyl acetate and washed with 1M hydrochloric acid, saturated sodium bicarbonate and saturated aqueous sodium chloride and dried over sodium sulfate. Concentration in vacuo provided the amide as a clear colorless oil (1.21 g, 89%).

Part C: To a solution of the amide of part B (1.20 g, 3.84 mmol) in dichloromethane (5 mL) was added trifluoroacetic acid (5 mL) and the solution was stirred for 1 hr. Concentration in vacuo provided an oil which was added directly to a solution of the compound of Preparative Example VII, Part A (956 mg, 2.56 mmol) in dimethylacetamide (10 mL). Cesium carbonate (2.92 g, 8.96 mmol) was added and the solution was heated to 100° C. for 18 hr. The solution was partitioned between ethyl acetate and water and the organic layer was washed with water and saturated sodium chloride and dried over sodium sulfate. Concentration in vacuo provided the phenylamine as an oil (1.53 g, 68%). MS(CI) MH+ calculated for $C_{30}H_{47}N_3O_6S$: 578, found 578.

Part D: To a solution of the phenylamine of part C (1.5 g, 2.6 mmol) in ethanol (9 mL) and tetrahydrofuran (9 mL) was added sodium hydroxide (1.02 g, 26 mmol) in water (5 mL) and the solution was heated to 60° C. for 20 hr. The solution was concentrated and the residue was diluted with water and acidified to pH=3 with 3N hydrochloric acid. Vacuum filtration provided the acid as a beige solid (500 mg, 33%). MS(CI) MH+ calculated for $C_{28}H_{43}N_3O_6S$: 550, found 550.

Part E: To a solution of the acid of part D (492 mg, 0.84 mmol) in N,N-dimethylformamide (10 mL) was added 1-hydroxybenzotriazole hydrate (136 mg, 1.01 mmol), 4-methylmorpholine (0.46 mL, 4.20 mmol), and O-tetrahydropyranyl hydroxylamine (147 mg, 1.26 mmol). After 1 hr, 1-[3-(dimethylamino)propyl]-3-ethylcarbodiimide hydrochloride (225 mg, 1.18 mmol) was added and the solution was stirred for 72 hr at ambient temperature. The solution was partitioned between ethyl acetate and water. The organic layer was washed with water and saturated sodium chloride and dried over sodium sulfate. Concentration in vacuo provided the protected hydroxamate as an oil (524 mg, 96%). MS(CI) MH+ calculated for $C_{33}H_{51}N_4O_7S$: 649, found 649.

Part F: To a solution of the protected hydroxamate of part E (514 mg, 0.79 mmol) in 1,4-dioxane (10 mL) was added 4M hydrochloric acid in dioxane (10 mL) and the solution was stirred for 1.5 hr. The solution was concentrated in vacuo and trituration (ethyl ether) provided the title compound as a white solid (360 mg, 76%). MS(CI) MH+ calculated for $C_{28}H_{44}N_4O_6S$: 565, found 565. HRMS calculated for $C_{28}H_{44}N_4O_6S$: 565.3060, found 565.3070. Analytical calculation for $C_{28}H_{44}N_4O_6S$ 2HCl:2H$_2$O: C, 49.92; H, 7.48; N, 8.32; S, 4.76; Cl, 10.52. Found: C, 49.41; H, 7.55; N, 7.85; S, 4.53; Cl, 10.78.

Example 71

Preparation of 4-[[4-[4-[(3,5-dimethyl-1-piperidinyl) carbonyl]-1-piperidinyl]-phenyl]sulfonyl]-N-hydroxy-1-(2-methoxyethyl)-4-piperidinecarboxamide

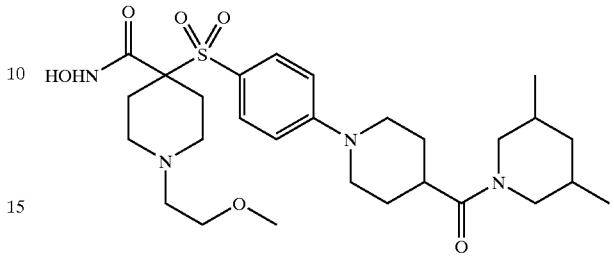

A solution of the hydroxamate of Example 70, part F (50 mg, 0.08 mmol) in water (2 mL) was neutralized with saturated sodium bicarbonate. The aqueous solution was extracted with ethyl acetate. Concentration in vacuo provided the hydroxamate free base as an orange solid (35 mg, 75%).

Example 72

Preparation of rel-4-[[4-[4-[[(3R,5R)-3,5-dimethyl-1-piperidinyl]carbonyl]-1-piperidinyl]phenyl] sulfonyl]-N-hydroxy-4-piperidinecarboxamide, monohydrochloride

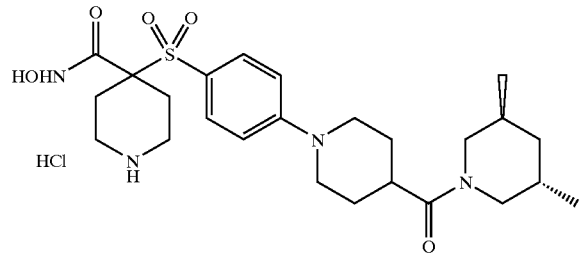

Part A: To a solution of the N-Boc-isonipecotic acid of Example 70, Part A (1.0 g, 4.37 mmol) in dichloromethane (10 mL) was added 1-[3-(dimethylamino)propyl]-3-ethylcarbodiimide hydrochloride (853 mg, 4.45 mmol), 1-hydroxybenzotriazole hydrate (620 mg, 4.59 mmol) 3,5-dimethylpiperdine (0.67 mL, 5.03 mmol) and diisopropylethylamine (1.67 mL, 9.61 mmol) and was stirred for 21 hr. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a clear colorless oil (1.4 g, quantitative yield).

Part B: To a solution of the amide of part A (1.4 g, 4.49 mmol) in dioxane (10 mL) was added 4M hydrochloric acid in dioxane (10 mL) and the solution was stirred for 1 hr. Concentration in vacuo provided a solid that was added directly to a solution of the compound of Preparative Example II, Part D, (1.24 mg, 2.99 mmol) in dimethylacetamide (10 mL). Cesium carbonate (3.42 g, 10.5 mmol) was added and the solution was heated to 100° C. for 20 hr. The solution was partitioned between ethyl acetate and water and the organic layer was washed with water and saturated sodium chloride and dried over sodium sulfate. Concentration in vacuo provided the phenylamine as a yellow solid (1.90 g, quantitative yield). MS(CI) MH+ calculated for $C_{32}H_{49}N_3O_7S$: 620, found 620.

Part C: To a solution of the phenylamine of part B (1.9 g, 3.0 mmol) in ethanol (10 mL) and tetrahydrofuran (10 mL) was added sodium hydroxide (1.2 g, 30 mmol) in water (5 mL) and the solution was heated to 60° C. for 20 hr. The solution was concentrated and the residue was diluted with water and acidified to pH=1 with 3N hydrochloric acid. The solution was extracted with ethyl acetate and washed with 1M hydrochloric acid and saturated sodium chloride and dried over magnesium sulfate. Concentration in vacuo provided the acid as a yellow oil (1.9 g, quantitative yield). MS(CI) MH+ calculated for $C_{30}H45N_3O_7S$: 592, found 592.

Part D: To a solution of the acid of part C (1.87 g, 3.00 mmol) in N,N-dimethylformamide (10 mL) was added 1-hydroxybenzotriazole hydrate (486 mg, 3.6 mmol), 4-methylmorpholine (1.65 mL, 15 mmol), and O-tetrahydropyranyl hydroxylamine (526 mg, 4.5 mmol). After 1 hr, 1-[3-(dimethylamino)propyl]-3-ethylcarbodiimide hydrochloride (805 mg, 4.2 mmol) was added and the solution was stirred for 18 hr at ambient temperature. The solution was partitioned between ethyl acetate and water. The organic layer was washed with water and saturated sodium chloride and dried over sodium sulfate. Chromatography (on silica, ethyl acetate/hexane) provided the protected hydroxamate as an oil (1.63 g, 79%).

Part E: To a solution of the protected hydroxamate of part D (1.61 g, 2.33 mmol) in dioxane (10 mL) was added 4M hydrochloric acid in dioxane (10 mL) and the solution was stirred for 45 min. The solution was concentrated in vacuo and trituration (ethyl ether) a white solid. Reverse phase chromatography (on silica, acetonitrile/water(hydrochloric acid)) produced fractions A, B, C and D. Concentration in vacuo of fraction A provided the title compound as a white solid (59 mg). MS(CI) MH+ calculated for $C_{25}H_{38}N_4O_5S$: 507, found 507.

Example 73

Preparation of rel-1,1-dimethylethyl 4-[[4-[4-[[(3R,5R)-3,5-dimethyl-1-piperidinyl]carbonyl]-1-piperidinyl]-phenyl]sulfonyl]-4-[(hydroxyamino)-carbonyl]-1-piperidinecarboxylate

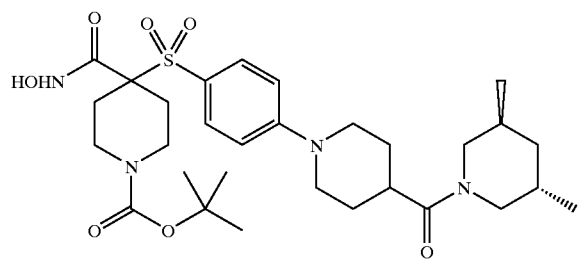

From the reverse phase chromatography of Example 72, Part E, fraction C was concentrated in vacuo to provide the title compound as a white solid (49 mg). MS(CI) MH+ calculated for $C_{30}H_{46}N_4O_7S$: 607, found 607.

Example 74

Preparation of rel-4-[[4-[4-[[(3R,5S)-3,5-dimethyl-1-piperidinyl]carbonyl]-1-piperidinyl]phenyl]sulfonyl]-N-hydroxy-4-piperidinecarboxamide, monohydrochloride

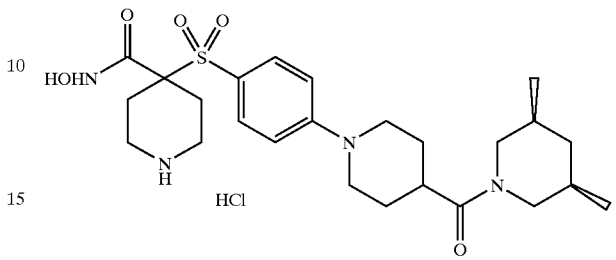

From the reverse phase chromatography of Example 72, Part E, fraction B was concentrated in vacuo to provide the title compound as a white solid (198 mg). MS(CI) MH+ calculated for $C_{25}H_{38}N_4O_5S$: 507, found 507.

Example 75

Preparation of rel-1,1-dimethylethyl 4-[[4-[4-[[(3R,5S)-3,5-dimethyl-1-piperidinyl]carbonyl]-1-piperidinyl]-phenyl]sulfonyl]-4-[(hydroxyamino)-carbonyl]-1-piperidinecarboxylate

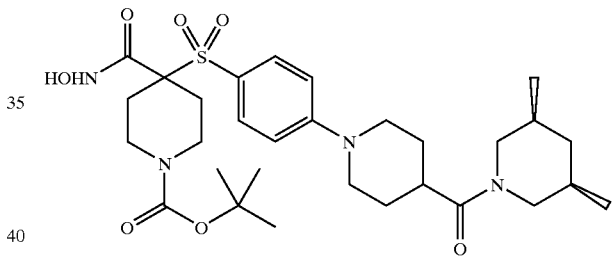

From the reverse phase chromatography of Example 72, Part E, fraction D was concentrated in vacuo to provide the title compound as a white solid (242 mg). MS(CI) MH+ calculated for $C_{30}H_{46}N_4O_7S$: 607, found 607.

Example 76

Preparation of 4-[[4-[4-[(2,3-dihydro-1H-indol-1-yl)carbonyl]-1-piperidinyl]-phenyl]sulfonyl]-N-hydroxy-1-(2-methoxyethyl)-4-piperidinecarboxamide, monohydrate

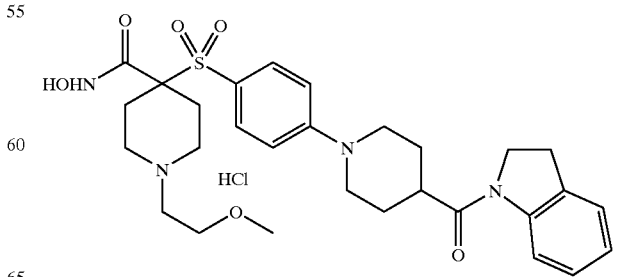

Part A: To a solution of the N-Boc-isonipecotic acid of Preparative Example I, Part B (750 mg, 3.27 mmol) in dichloromethane (3 mL) was added 2-chloro-4,6-dimethoxy-1,3,5-triazine (564 mg, 3.21 mmol). The solution was cooled to 0° C. and 4-methylmorpholine (0.35 mL, 3.21 mmol) was added. After 2 hr, indoline (0.36 mL, 3.21 mmol) was added and the solution was stirred for 22 hr at ambient temperature. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a pink solid (940 mg, 89%).

Part B: To a solution of the amide of part A (935 g, 2.83 mmol) in 1,4-dioxane (10 mL) was added 4M hydrochloric acid in dioxane (10 mL) and the solution was stirred for 1 hr. Concentration in vacuo provided an oil which was added directly to a solution of the compound of Preparative Example VII, Part A, (705 mg, 1.89 mmol) in dimethylacetamide (10 mL). Cesium carbonate (2.15 g, 6.61 mmol) was added and the solution was heated to 110° C. for 18 hr. The solution was partitioned between ethyl acetate and water and the organic layer was washed with water and saturated sodium chloride and dried over sodium sulfate. Concentration in vacuo provided the phenylamine as an orange oil (893 mg, 81%). MS(CI) MH+ calculated for $C_{31}H_{41}N_3O_6S$: 584, found 584.

Part C: To a solution of the phenylamine of part B (885 g, 1.52 mmol) in ethanol (10 mL) and tetrahydrofuran (10 mL) was added sodium hydroxide (607 mg, 15.2 mmol) in water (5 mL) and the solution was heated to 60° C. for 20 hr. The solution was concentrated and the residue was diluted with water and acidified to pH=1 with 3N hydrochloric acid producing a solid. Vacuum filtration provided the acid as a beige solid (475 g, 53%). MS(CI) MH+ calculated for $C_{29}H_{37}N_3O_6S$: 556, found 556.

Part D: To a solution of the acid of part C (465 g, 0.79 mmol) in N,N-dimethylformamide (10 mL) was added 1-hydroxybenzotriazole hydrate (128 mg, 0.95 mmol), 4-methylmorpholine (0.43 mL, 3.95 mmol), and O-tetrahydropyranyl hydroxylamine (139 mg, 1.18 mmol). After 1 hr, 1-[3-(dimethylamino)propyl]-3-ethylcarbodiimide hydrochloride (212 mg, 1.10 mmol) was added and the solution was stirred for 18 hr at ambient temperature. The solution was partitioned between ethyl acetate and water. The organic layer was washed with water and saturated sodium chloride and dried over sodium sulfate. Chromatography (on silica, ethyl acetate/methanol) provided the protected hydroxamate as a yellow oil (305 mg, 60%). MS(CI) MH+ calculated for $C_{34}H_{46}N_4O_7S$: 655, found 655.

Part E: To a solution of the protected hydroxamate of part D (300 mg, 0.46 mmol) in dioxane (5 mL) was added 4M hydrochloric acid in dioxane (5 mL) and the solution was stirred for 2 hr. The resulting solid was collected by vacuum filtration. Washing with ethyl ether provided the title compound as a white solid (260 mg, 94%). MS(CI) MH+ calculated for $C_{29}H_{34}N_4O_6S$: 571, found 571.

The following compounds were prepared by parallel synthesis (resin based synthesis, automated synthesis) procedures utilizing reactions such as acylation and nucleophilic displacement:

Example 77:

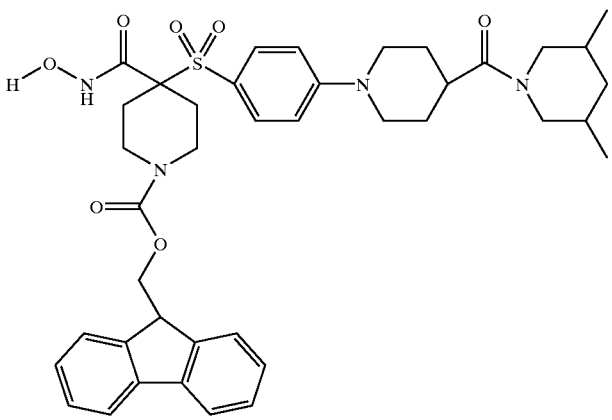

Example 78:

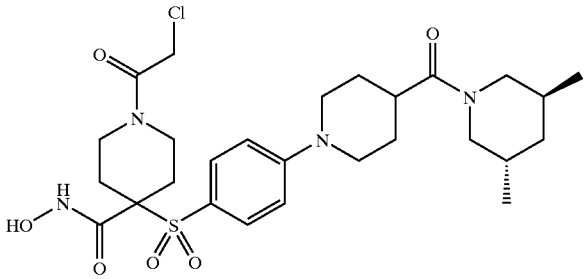

-continued

Example 79:

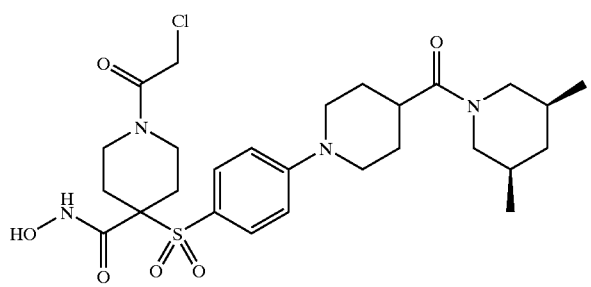

Examples: 80–118

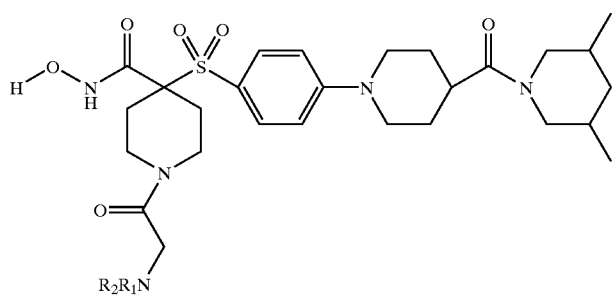

| Example | R₁R₂NH | Amine | MS (ES) m/z |
|---|---|---|---|
| 80 | Ethyl amine structure | Ethyl amine | 592 (M + H) |
| 81 | 3-pyridyl-CH₂NH₂ | 3-(Aminomethyl) pyridine | 655 (M + H) |
| 82 | Imidazole | Imidazole | 615 (M + H) |
| 83 | H₂N–propyl–OH | 3-Amino-1-propanol | 622 (M + H) |
| 84 | Histamine structure | Histamine | 658 (M + H) |
| 85 | 2-thienyl-CH₂NH₂ | 2-Thiophene methyl amine | 660 (M + H) |
| 86 | Morpholine | Morpholine | 634 (M + H) |
| 87 | 2-pyridyl-CH₂NH₂ | 2-(Aminomethyl) pyridine | 655 (M + H) |
| 88 | 4-pyridyl-CH₂NH₂ | 4-(Aminomethyl) pyridine | 655 (M + H) |
| 89 | H₂N–CH₂CH₂–OH | Ethanolamine | 608 (M + H) |

-continued

| | | | |
|---|---|---|---|
| 90 | CH3-NH-CH2-CH2-N(CH3)2 | N,N,N-Trimethyl ethylenediamine | 649 (M + H) |
| 91 | HN-piperazine-N-CH3 | 1-Methylpiperazine | 647 (M + H) |
| 92 | H2N-CH2-CH2-N(CH3)2 | N,N-Dimethyl ethylenediamine | 635 (M + H) |
| 93 | HN-piperazine-NH | Piperazine | 633 (M + H) |
| 94 | HN-thiomorpholine-S | Thiomorpholine | 650 (M + H) |
| 95 | CH3CH2CH2-NH-CH2-cyclopropyl | N-Propylcyclopropne methylamine | 660 (M + H) |
| 96 | H2N-CH2-cyclopropyl | (Aminomethyl) cyclopropane | 618 (M + H) |
| 97 | CH3-NH-CH3 | Dimethylamine | 592 (M + H) |
| 98 | CH3CH2-NH-CH2CH3 | Diethylamine | 620 (M + H) |
| 99 | piperidine-NH | Piperidine | 632 (M + H) |
| 100 | (R)-pyrrolidine-CH2OH | (R)-(−)-2-Pyrrolidine methanol | 648 (M + H) |
| 101 | pyrrolidine-NH | Pyrrolidine | 618 (M + H) |
| 102 | HN-piperazine-N-CH2CH2-O-CH2CH2-OH | 1-(2-(2-Hydroxyethoxy) ethyl)piperazine | 721 (M + H) |
| 103 | HN-piperidine-C(O)NH2 | Isonipecotamide | 675 (M + H) |

-continued

| | | | |
|---|---|---|---|
| 104 | 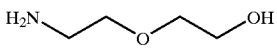 | 2-(2-Aminoethoxy) ethanol | 652 (M + H) |
| 105 | 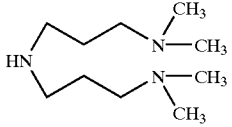 | 3,3'-Iminobis(N,N-dimethylpropylamine) | 734 (M + H) |
| 106 | 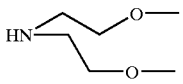 | Bis(2-Methoxy ethyl) amine | 680 (M + H) |
| 107 | 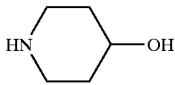 | 4-Hydroxy piperidine | 648 (M + H) |
| 108 | 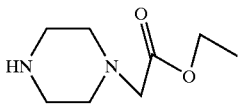 | N-(Carboethoxy methylpiperazine | 719 (M + H) |
| 109 | 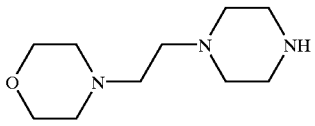 | 1-(2-Morpholinoethyl) piperazine | 746 (M + H) |
| 110 | 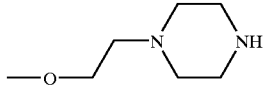 | 1-(2-Methoxyethyl) piperazine | 691 (M + H) |
| 111 | 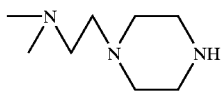 | 1-(2-Dimethylaminoethyl) piperazine | 704 (M + H) |
| 112 | 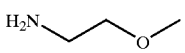 | 2-Methoxyethylamine | 622 (M + H) |
| 113 | 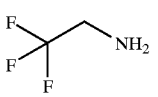 | 2,2,2-Trifluoroethyl amine | 646 (M + H) |
| 114 |  | 1,2,4-Triazole | 616 (M + H) |
| 115 | 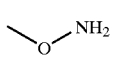 | Methoxyamine | 594 (M + H) |
| 116 | 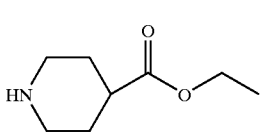 | Ethyl isonipecotate | 704 (M + H) |
| 117 | 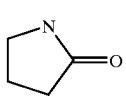 | 2-Pyrrolidinone | 632 (M + H) |
| 118 | 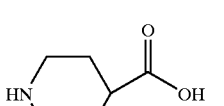 | Isonipecotic acid | 676 (M + H) |

Example 119

Preparation of

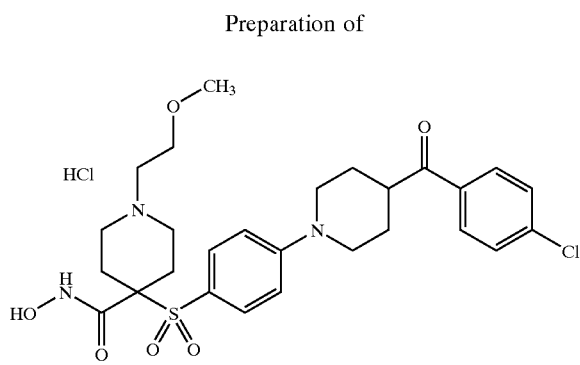

Part A. Preparation of aryl fluoride. To a solution of ethyl 4-[(4-fluorophenyl)sulfonyl]-1-(2-methoxyethyl)-4-piperidinecarboxylate (57 mmol) in dioxane (90 mL) and water (45mL) was added LiOH (4.8 g, 3.5 eq). The mixture was stirred at 60° C. overnight, cooled to room temperature, and concentrated in vacuo. The aqueous layer was treated with concentrated HCl until the pH was approximately 4. The solid was collected and dried. Next, the solid (47.8 mmol) in DMF (100 mL) was added NMM (26.2 mL, 239 mmol) and (benzotriazol-1-yl)-N,N,N',N'-bis(tetramethylene)uronium tetrafluoroborate (32.3 g, 62.1 mmol). The mixture was stirred at room temperature for 15 min, and O-(tetrahydro-2H-pyran-2-yl)hydroxylamine (6.71 g, 57.32 mmol) was then added. After 48 hr at room temperature, the mixture was quenched with sat. $NH_4^+Cl^-$, and then extracted with $CH_2Cl_2$ three times. The combined organic layer was dried and concentrated in vacuo. The residue was purified over $SiO_2$ using hexane/$CH_2Cl_2$ and then $CH_2Cl_2$/MeOH to give 20 g of protected hydroxyamide as an orange oil.

Part B. Aryl fluoride displacement. A solution of the aryl fluoride from Part A (0.45 mmol), $Cs_2CO_3$ (1.35 mmol, 3 eq), and 4-(4-chlorobenzoyle)piperidine (Maybridge Chemical Co., England, 0.67 mmol, 1.5 eq) in DMSO (1 mL) was heated to 110° C. for 18–48 hr. The mixture was then cooled, dissolved in saturated aq. $NH_4^+Cl^-$ (5 mL), and extracted with dichloromethane (3×3 mL). The combined organic layer was blown down. The crude product was purified by RPHPLC (eluting with 10% to 90% acetonitrile/water), and the pure fractions were combined and concentrated.

Part C. Conversion of the THP hydroxamic acid of Part B to the hydroxamic acid. The residue from Part B was dissolved in 2 mL of 4M HCl and 1 mL of MeOH, stirred at room temperature for 1 h, and then blown down. THEO M+H=564.1935; Observed: HI RES M+H=564.1949;.

Example 120

Preparation of

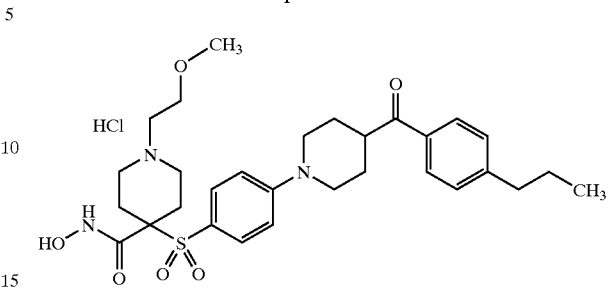

Part A. Preparation of 4-(4-n-propylbenzoyl)piperidine. To a solution of magnesium (147 mmol, 5 eq) in 40 mL of THF at 0° C. was added 1-bromo-4-(n-propyl)benzene (88.24 mmol, 3 eq). The solution was allowed to warm to room temperature over approximately 3 hr. The weinreb amide (29.4 mmol, 1 eq) having the following structure:

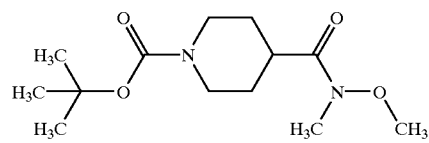

was added, and then the mixture was stirred at room temperature for 18 hr. The mixture was quenched with saturated $NH_4^+Cl^-$, and then extracted with $CH_2Cl_2$ three times. The combined organic layer was washed with saturated $NH_4^+Cl^-$, dried over $MgSO_4$, and concentrated in vacuo. The residue was purified over 70 g of $SiO_2$, eluting with ethylacetate:hexanes (1:10) to ethylacetate:hexanes (1:3). The piperidine was dissolved in 20 mL of $CH_2Cl_2$ and 20 mL of trifluoroacetate. The resulting mixture was stirred at room temperature for 1 hr, and then concentrated in vacuo. The residue was treated with 5% NaOH until a solid precipitated out. The solid was collected and then dissolved in dichloromethane, dried, and concentrated in vacuo. The residue was recrystallized in MeOH/Ether to give 5.07 g of 4-(4-n-propylbenzoyl)piperidine.

Part B. Aryl fluoride displacement. A solution of the aryl fluoride (0.45 mmol., as prepared in Part A of the preceding example), $Cs_2CO_3$ (1.35 mmol, 3 eq), and the 4-(4-n-propylbenzoyl)piperidine prepared in Part A above (0.65 mmol, 1.5 eq) in DMSO (1 mL) was heated to 110° C. for 18–48 hr. The mixture was cooled, dissolved in saturated aqueous $NH_4^+Cl^-$ (5 mL), and extracted with dichloromethane (3×3 mL). The combined organic layer was blown down. The crude product was purified by RPHPLC (eluting with 10% to 90% acetonitrile/water), and the pure fractions were combined and concentrated.

Part C. Conversion of the THP hydroxamic acid of Part B to the hydroxamic acid. The residue from Part C was dissolved in 2 mL of 4M HCl and 1 mL of MeOH, stirred at room temperature for 1 h, and then blown down. Theo: M+H=572.2794; Observed: Hi Res M+H=572.2755;

Example 121

Preparation of

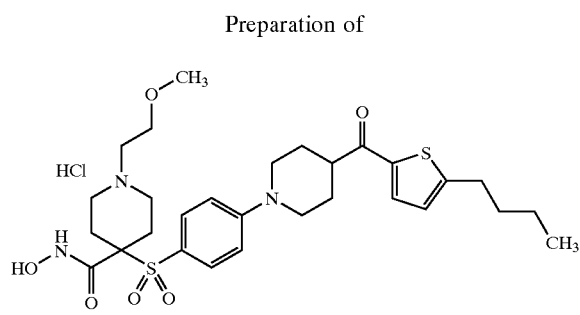

Part A:

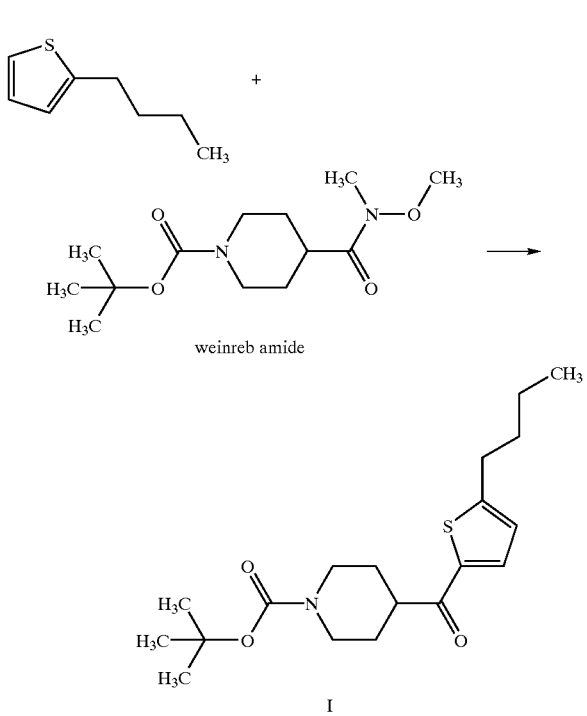

To a solution of n-butylthiophene (Lancaster, 5.0 g, MW 140.26, 1.1 eq) in tetrahydrofuran (80 ml) at 0° C. was dripped in 1.6 M n-butyllithium in hexanes (Aldrich, 24 ml, 1.2 eq). The mixture stirred at 0° C. for 0.5 hr under $N_2$. The reaction vessel was then cooled to −78° C., and a solution of the weinreb amide (shown in the reaction above) in tetrahydrofuran (30 ml) was slowly added. The dry ice bath was removed, and the reaction was allowed to warm to room temperature. After 3 hr, the conversion was complete. The reaction was quenched with water (50 ml), and the organic layer was removed in vacuo. More water (100 ml) was added, and the mixture was extracted with diethylether (3×100 ml). The organic layers were washed with water (2×) and brine (1×), dried over $Na_2SO_4$, and concentrated to afford a brown oil that was chromatographed (ethylacetate:hexanes, 1:9) to afford 7.5 g of a pale yellow solid (67% crude yield). $^1$H NMR showed the desired compound.

Part B

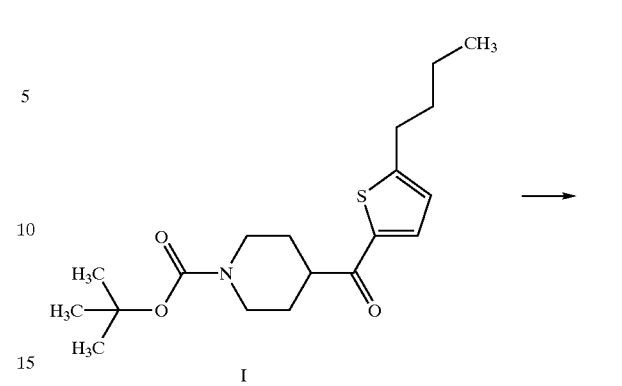

To a solution of Compound I (7.4 g, MW 351.50, 1.0 eq) in acetonitrile (10 ml) was added 4 N HCl in dioxane (Pierce, 40 ml). After 1 hr, the solvent was evaporated, and the residue was slurried in diethylether to afford a white solid that was collected and dried for 5.8 g (97% yield). $^1$H NMR showed the desired Compound II.

Part C

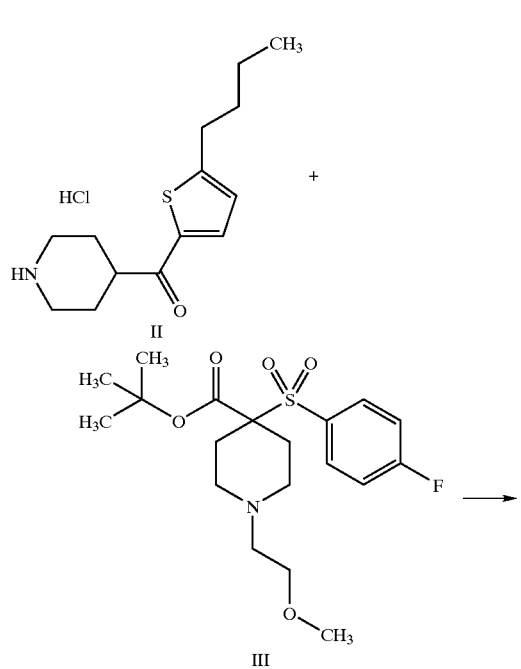

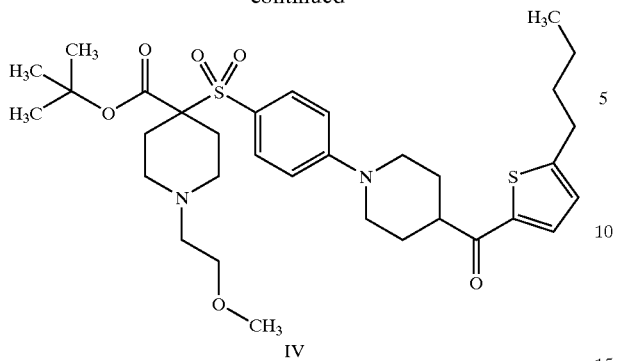

IV

To a solution of Compound II (2.1 g, MW 287.85, 1.5 eq) in dimethylsulfoxide (Aldrich, 15 ml) was added CsCO$_3$ (Aldrich, 6.4 g, MW 325.8, 4.0 eq). After stirring for 5 min, Compound III (2.0 g, MW 401.49, 1.0 eq) was added, and the mixture was stirred at 90° C. for 24 hr. The mixture was then diluted with water (15 ml), and extracted with ethylacetate (3×100 ml). The organic layer was washed with water (1×), washed with brine (2×), dried over Na$_2$SO$_4$, and concentrated to a crude brown solid which was recrystallized from hot methanol for 1.83 g of an orange crystalline solid (59% yield). $^1$H NMR showed the desired Compound IV.

Part D

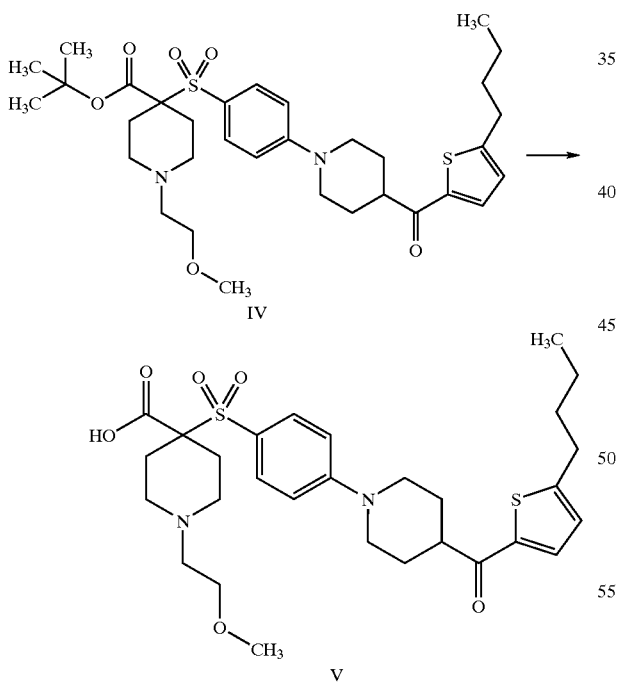

IV

V

To a solution of Compound IV (1.8 g, MW 632.88, 1.0 eq) in methylene chloride (5 ml) was added trifluoroacetic acid (10 ml). The mixture was stirred for 4 hr at room temperature. The mixture was then concentrated to ⅓ volume, and diethylether was added to afford a solid, which was collected and dried for 1.4 g tan solid (88% yield). $^1$H NMR and LCMS showed the desired Compound V.

Part E

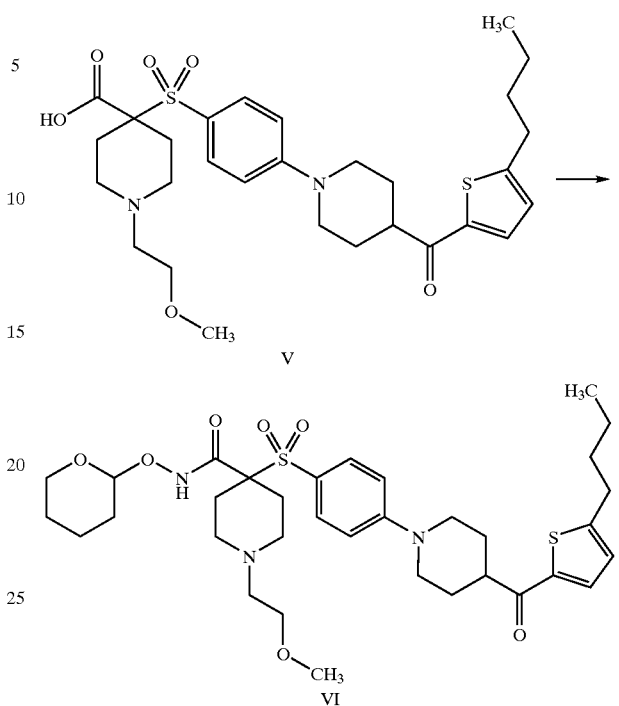

V

VI

To a solution of Compound V (1.3 g, 2.2 mmol) in N,N-dimethylformamide (8 ml) was added triethylamine (Aldrich, 1.2 ml, 8.8 mmol), followed by N-hydroxybenzotriazole hydrate (Aldrich, 0.6 g, 4.4 mmol), O-tetrahydro-2H-pyran-2-yl)hydroxylamine (0.4 g, 3.3 mmol), and, lastly, 1-(3-dimethylaminopropyl)-3-ethylcarbodiimide hydrochloride (Sigma, 0.9 g, 4.8 mmol). The mixture was stirred for 2 days at room temperature. The mixture was diluted with water (10 ml), and extracted with ethylacetate (3×75 ml). The organic layers were combined, and washed with a saturated sodium bicarbonate solution 1×150 ml) and brine 1×150 ml). The organic layer was then dried over Na$_2$SO$_4$, and concentrated to afford an orange foam that was recrystallized from methanol to afford a pale yellow solid (1.2 g, 80% yield). $^1$H NMR and LCMS showed the desired Compound VI.

Part F

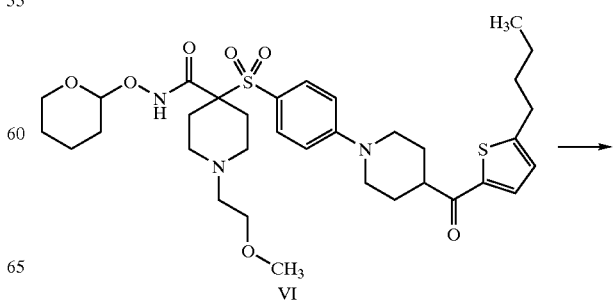

VI

-continued

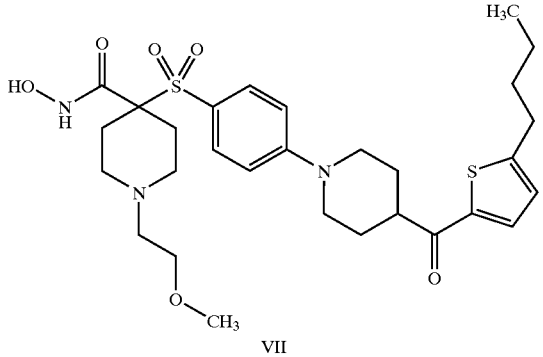

VII

The Compound VI (1.2 g, 1.8 mmol) was treated with methanol (0.5 ml) and 4 N HCl in dioxane (5 ml) for 1 hr. The solvents were concentrated to ⅓ the volume via an $N_2$ stream. Diethylether was then added to the residue to afford a solid that was collected and dried to a white solid (1.0 g, 91% yield). $^1$H NMR showed the desired Compound VII. HRMS confirmed this finding (theo M=H 592.2515, observed: 592.2498).

Example 122

Preparation of

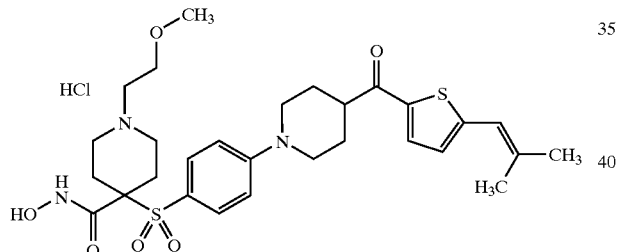

Part A

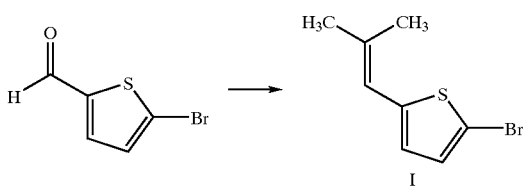

To an ice-cold suspension of isopropylphosphonium iodide (Aldrich, 40.7, MW 432.29, 3.0 eq) at 0° C. in tetrahydrofuran (240 ml) was slowly added n-butyllithium (Aldrich, 1.6 M, 58.9 ml, 3.0 eq). After 1 hr, a solution of 5-bromo-2-thiophene carboxaldehyde (Aldrich, 6.0 g, MW 191.05, 1.0 eq) in tetrahydrofuran (60 ml) was added in one shot. The ice bath was removed, and the mixture warmed to ambient temperature and stirred 2.5 hours. The reaction was quenched with water (110 ml) followed by 1 N HCl (110 ml). An emulsion developed that was filtered through a coarse frit funnel. The filtrate was separated and the organic was washed with brine (200 ml), dried over $Na_2SO_4$, and concentrated to afford a black oil. Purification on silica gel (ethyl acetate/hexanes) gave 3.4 g of a yellow oil (50% yield). $^1$H NMR showed desired Compound I.

Part B

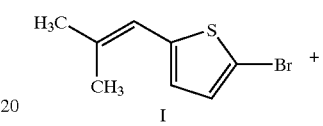

I

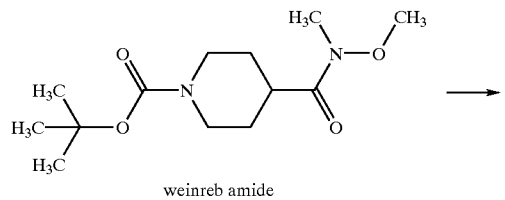

weinreb amide

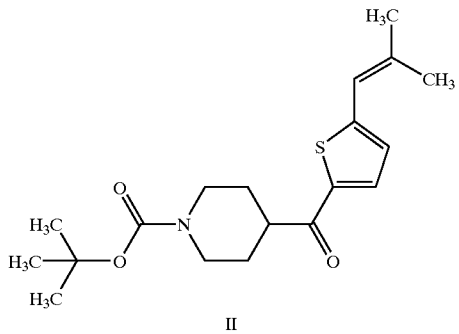

II

To a solution of Compound I (2.89 g, MW 217.13, 1.5 eq) in tetrahydrofuran (25 ml) at −40° C. was dripped 2.0M isopropylmagnesium chloride in tetrahydrofuran (Aldrich, 6.9 ml, 1.55 eq). The mixture was stirred at −40° C. for 1.5 hr under $N_2$. A solution of the weinreb amide (shown in the above reaction) in tetrahydrofuran (30 ml) was quickly added. The dry ice bath was removed, and the mixture was allowed to warn to room temperature and stirred overnight. The reaction was quenched with 1 N HCl (25 ml), followed by water (25 ml). The organic layer was removed in vacuo. The aqueous residue was extracted with diethylether (3×100 ml). The organic layers were washed with water (2×) and brine (1×), dried over $Na_2SO_4$, and concentrated to afford a brown oil that was slurried with hexanes. A solid formed, which was subsequently filtered to afford 1.9 g of gray solid (61% crude yield). $^1$H NMR showed the desired Compound II.

Part C

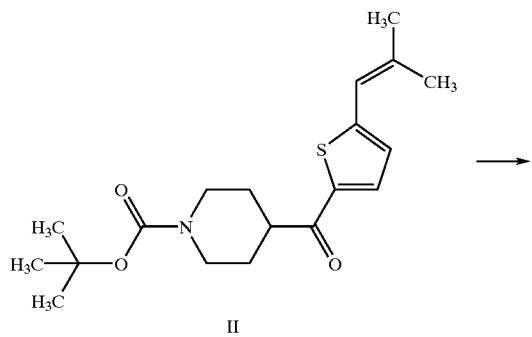

To Compound II (1.9 g, MW 349.49, 1.0 eq) was added 4 N HCl in dioxane (Pierce, 10 ml). After 1 hr, the solvent was evaporated, and the residue was slurried in diethylether to afford a gray solid that was collected and dried for 1.4 g (93% yield). ¹H NMR showed the desired Compound III.

Part D

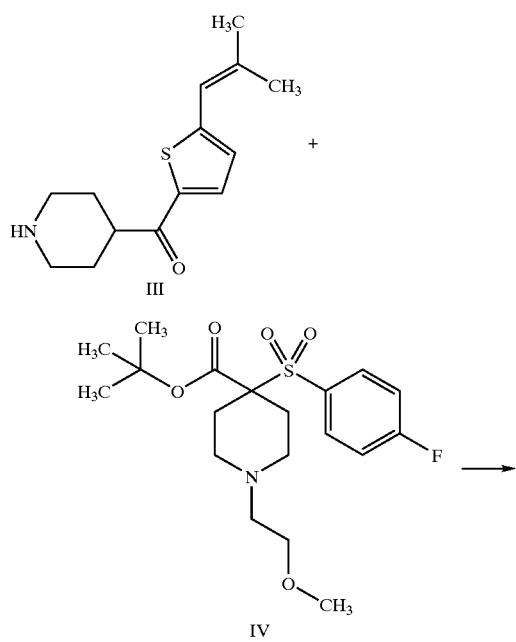

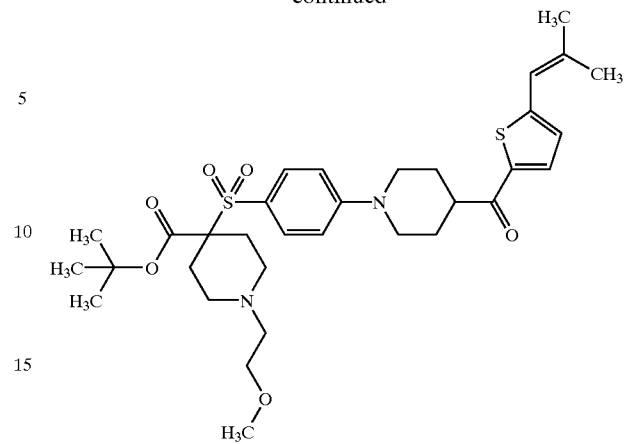

To a solution of Compound III (1.4 g, MW 285.83, 1.5 eq) in dimethylsulfoxide (Aldrich, 10 ml) was added CsCO₃ (Aldrich, 4.0 g, MW 325.8, 4.0 eq). After 5 min, Compound IV (1.3 g, MW 401.49, 1.0 eq) was added, and the reaction was stirred at 100° C. for 24 hr. The mixture was then diluted with water (15 ml), and extracted with ethylacetate (3×100 ml). The organic layers were washed with water (1×) and brine (2×), dried over Na₂SO₄, and concentrated for a crude yellow solid, which was recrystallized from hot methanol for 0.98 g of a yellow crystalline solid (50% yield). LCMS (M+H) showed the desired Compound V.

Part E

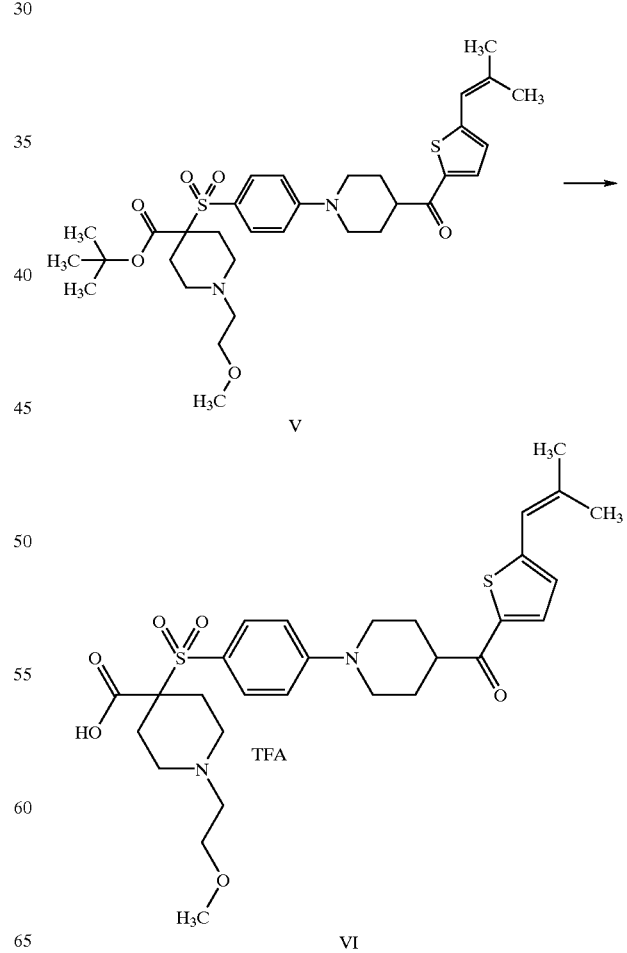

To a solution of Compound V (0.98 g, MW 630.86, 1.0 eq) in methylene chloride (4 ml) was added trifluoroacetic acid (4 ml, TFA). The mixture was stirred for 4 hr at room temperature. The mixture was then concentrated to ⅓ volume, and diethylether was added to afford a solid, which was collected and dried for 1.0 g tan solid (93% yield). ¹H NMR and LCMS showed the desired Compound VI.

Part F

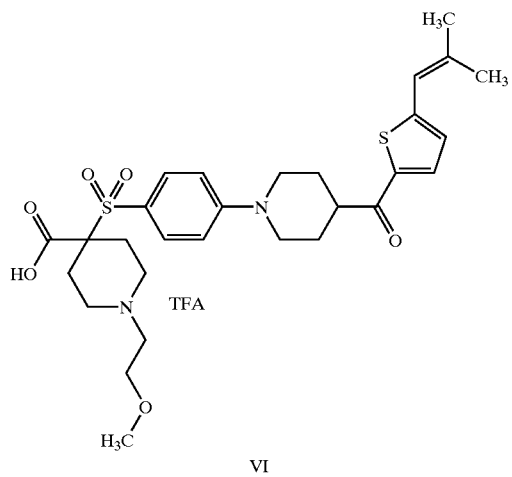

VI

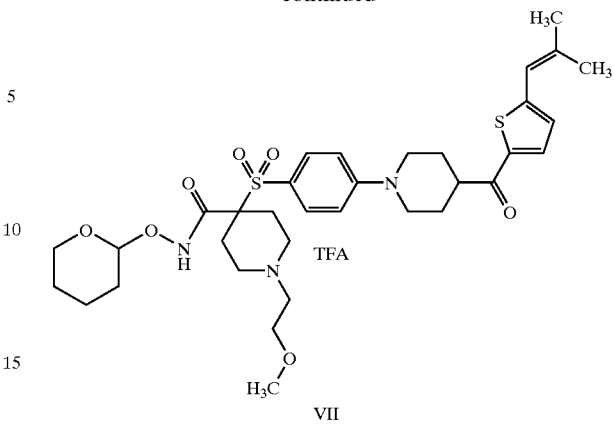

VII

To a solution of Compound VI (1.0 g, MW 688.77, 1.0 eq) in N,N-dimethylformamide (5 ml) was added triethylamine (Aldrich, 0.8 ml, MW 101.19, 4.0 eq) followed by N-hydroxybenzotriazole hydrate (Aldrich, 0.38 g, MW 135.13, 2.0 eq), )-(tetrahydro-2H-pyran-2-yl), hydroxylamine (0.25 g, MW 117.16, 1.5 eq), and, lastly, 1-(3-dimethylaminopropyl)-3-ethylcarbodiimide hydrochloride (Sigma, 0.59 g, MW 191.76, 2.2 eq). The mixture stirred at ambient temperature for 18 hr.

To work up the reaction was diluted with water (10 ml) and extracted with ethylacetate (3×75 ml). The organics were combined and washed with a saturated sodium bicarbonate solution (1×150 ml), and brine (1×150 ml). The organic was then dried over Na₂SO₄, and concentrated to afford a 0.9 g of a brown oil (96% yield). ¹H NMR and LCMS showed the desired Compound VII.

Part G

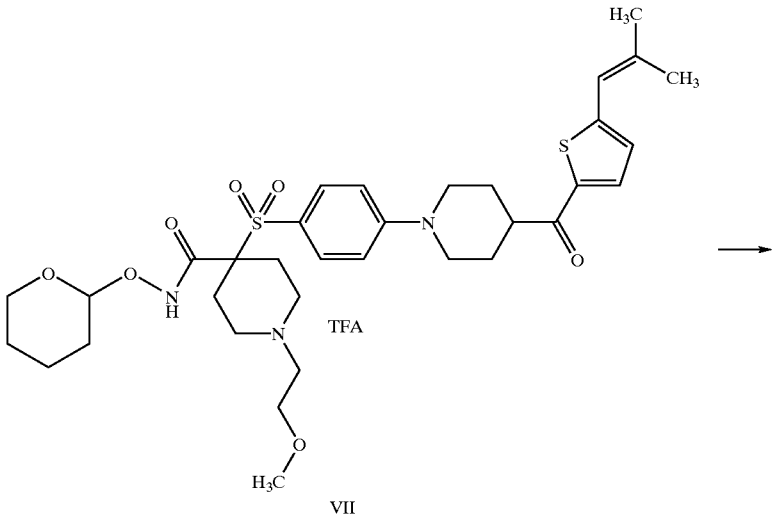

VII

-continued

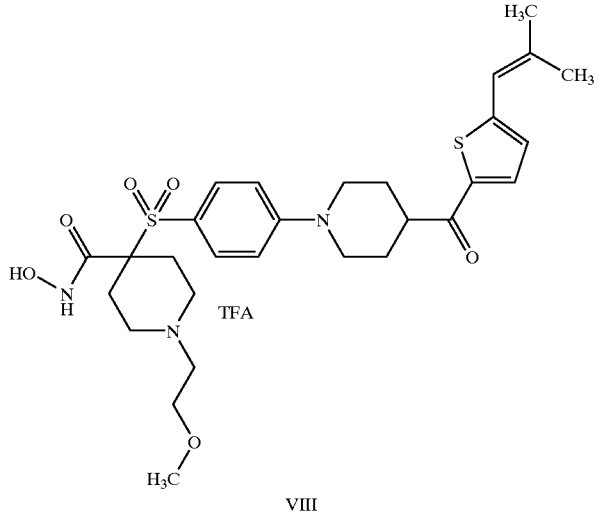

VIII

The Compound VII (0.9 g, MW 673.88, 1.0 eq) was treated with methanol (0.5 ml) and 4 N HCl in dioxane (5 ml) for 1 hr). The solvents were concentrated to ⅓ the volume via an $N_2$ stream. Diethylether was then added to the residue to afford a solid that was collected and dried for a brown solid (0.32 g, 40% yield). $^1$H NMR showed the desired Compound VIII. HRMS confirmed this observation (theo. M+H 590.2359, observed M+H 590.2364).

Example 123

Preparation of

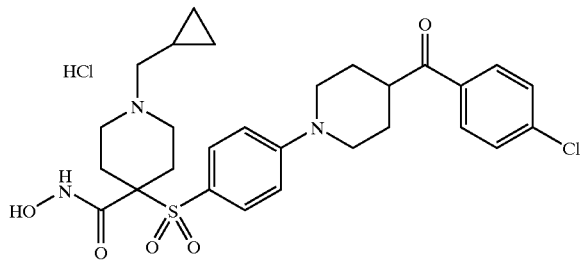

Part A. Preparation of aryl fluoride ester

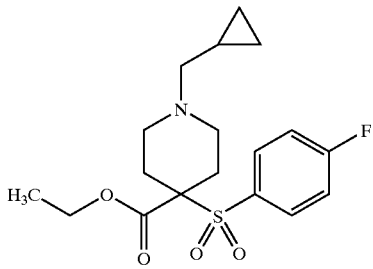

To a solution of molecular slieves (7.5 g), ethyl 5-[(4-fluorophenyl(sulfonyl]-4-piperidinecarboxylate, monohydrate (15g, 42.6 mmol) in methanol (75 mL), and acetic acid (9 mL) was added sodium cyano borohydride (7.23g, 115 mmol). The mixture was stirred at room temperature for 48 hr. The mixture was then quenched with sat. $NH_4^+Cl^-$, and extracted with $CH_2Cl_2$ three times. The combined organic layer was dried and concentrated in vacuo. The residue was then recrystallized using ethanol and ether to give 12.1 g (32.7 mmol) of the aryl fluoride ester.

Part B. Aryl fluoride displacement. A solution of the aryl fluoride from Part A (0.45 mmol), $Cs_2CO_3$ (1.35 mmol, 3 eq), and 4-(4-chlorobenzoyle)piperidine (Maybridge, England, 0.67 mmol, 1.5 eq) in DMSO (1 mL) was heated to 110° C. for 18–48 h. The mixture was cooled, dissolved in saturated aqueous $NH_4^+Cl^-$ (5 mL), and extracted with dichloromethane (3×3 mL). The combined organic layer was blown down, and the crude product was purified by crystallization using ethanol and ether.

Part C. Converting the ethyl ester to the hydroxamic acid. A solution of ethyl ester (5 g) in ethanol (8 mL), tetrahydrofuran (4 mL), and 50% aqueous NaOH (2 mL) was heated to 50° C. for approximately 2 hr (additional ethanol and THF can be added if the solid was not completely soluble after 1 hr at 50° C.). The residue was neutralized to a pH of 5–6 with aqueous HCl. The aqueous layer was concentrated in vacuo, and the resulting solid was washed with acetonitrile and water, and dried under high vacuum. A solution of the acid, NMM (3 eq), EDC (1.4 eq), and HOBT (1.5 eq) in DMF (5 mL) was heated at 40° C. for 2 hr. The amine was added, and then stirred at room temperature for 18–48 hr. The reaction mixture was quenched with saturated aqueous $NH_4^+Cl^-$, and extracted with dichloromethane. The combined organic layer was concentrated. The THP amide was purified over $SiO_2$ using $CH_2Cl_2$/methanol/triethylamine (the THP amide may alternatively be purified by reverse-phase chromatography). The resulting solid was then dissolved in 10 mL of 4M HCl and 10 mL of methanol, and stirred at room temperature until completion (30 min to 120 min). The mixture was then blown down, and the resulting solid was re-dissolved in methanol and poured into isopropyl alcohol. The solid was collected and dried. THEO M+H=560.1986; observed HI RES M+H=560.1999.

Example 124

Preparation of

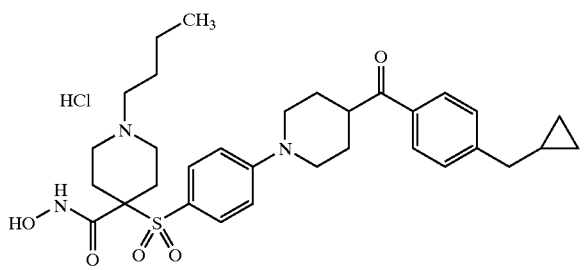

Part A. Preparation of 4-(4-metholcyclopropylbenzoyl) piperidine. To a solution of 4-bromophenylcyclopropyl ketone (Acros, 20 g, 89 mmol) in THF (75 mL) was added sodium borohydride (2.25 g, 60 mmol) and aluminum trichloride (3.95 g, 30 mmol) in small portions at −5° C. The mixture was allowed to warm to room temperature for 18 hr, and then stirred an additional 3 hr at 40° C. The mixture was then cooled, quenched with saturated $NH_4^+Cl^-$, and extracted with $CH_2Cl_2$ three times. The combined organic layer was dried and concentrated in vacuo. The mixture was chromatographed over 70 g of $SiO_2$ eluting with EtOAc:Hexane (0:100 to 10:90) to give 14.55 g (69 mmol) of 4-methyl cyclopropyl aryl bromide. To a cooled to 0° C. solution of the 4-methyl cyclopropyl aryl bromide (7.75 g, 36.7 mmol) in 20 mL of THF was added magnesium (55 mmol, 3 eq), followed by dibromoethane (10 uL) in small portions, keeping the mixture cold. The solution was stirred for 3 hr. The weinreb amide described in Example 120 (5 g, 18.4 mmol) was added at 0° C., and the mixture was stirred at room temperature for 48 hr. The mixture was then quenched with saturated $NH_4^+Cl^-$, and extracted with $CH_2Cl_2$ three times. The combined organic layer was dried and concentrated in vacuo. The mixture was chromatographed over 70 g of $SiO_2$ eluting with EtOAc/Hexane (0:100 to 30:70) to give 5.54 g (16 mmol) of the desired BOC-protected piperidine. The BOC-protected piperidine was then dissolved in 20 mL of $CH_2Cl_2$ and 20 mL of TFA, and stirred at room temperature for 1 hr. The mixture was concentrated in vacuo, and the residue was treated with 5% NaOH and water, and then extracted with $CH_2Cl_2$ three times. The combined organic layer was dried and concentrated in vacuo to give 3.47 g (14.3 mmol) of the 4-(4-metholcyclopropylbenzoyl)piperidine.

Part B. Aryl fluoride displacement. A solution of ethyl 4-[(4-fluorophenyl)sulfonyl]-1-(2-methoxyethyl)-4-piperidinecarboxylate (0.45 mmol), $Cs_2CO_3$ (1.35 mmol, 3 eq), and 4-(4-metholcyclopropylbenzoyl)piperidine from Part A in DMSO (1 mL) was heated to 110° C. for 18–48 h. The mixture was cooled, dissolved in saturated aqueous $NH_4^+Cl^-$ (5 mL), and extracted with dichloromethane (3×3 mL). The combined organic layer was blown down, and the crude product was purified by crystallization using ethanol and ether.

Part C. Converting the ethyl ester to the hydroxamic acid. A solution of ethyl ester (5 g) in ethanol (8 mL), tetrahydrofuran (4 mL), and 50% aqueous NaOH (2 mL) was heated to 50° C. for approximately 2 hr (additional ethanol and THF can be added if the solid is not completely soluble after 1 hr at 50° C.). The residue was neutralized to a pH of 5–6 with aqueous HCl. The aqueous layer was concentrated in vacuo, and the resulting solid was washed with acetonitrile and water, and dried under high vacuum. A solution of the acid, NMM (3 eq), EDC (1.4 eq), and HOBT (1.5 eq) in DMF (5 mL) was heated at 40° C. for 2 hr. The amine was added, and then stirred at room temperature for 18–48 hr. The reaction mixture was quenched with saturated aqueous $NH_4^+Cl^-$, and extracted with dichloromethane. The combined organic layer was concentrated. The THP amide was purified over $SiO_2$ using $CH_2Cl_2$/methanol/triethylamine (the THP amide may alternatively be purified by reverse-phase chromatography). The resulting solid was then dissolved in 10 mL of 4M HCl and 10 mL of methanol, and stirred at room temperature until completion (30 min to 120 min). The mixture was then blown down, and the resulting solid was re-dissolved in methanol and poured into isopropyl alcohol. The solid was collected and dried. THEO M+H=584.2794; observed HI RES M+H=584.2795.

Examples 125–387

The following compounds were prepared in a manner similar to that used in the preceding examples. In the tables that follow, a generic structure is shown above the table with substituent groups being illustrated in the table along with available mass spectral data.

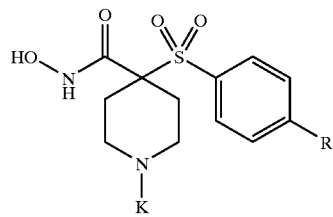

| Example | R | K | MS (ES) m/z |
|---|---|---|---|
| 125 | (4-piperidinyl-C(O)-phenyl-ethyl, HCl) | (cyclopropylmethyl) | |

-continued
| | | | |
|---|---|---|---|
| 126 | 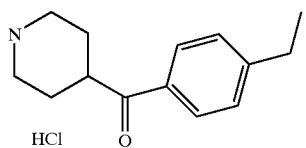 |  | |
| 127 | 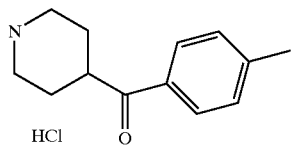 |  | |
| 128 | 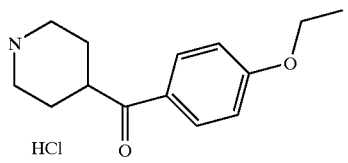 |  | |
| 129 | 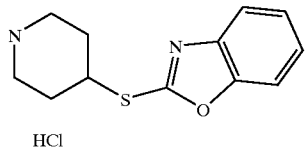 |  | |
| 130 | 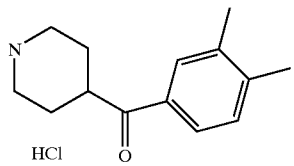 |  | |
| 131 | 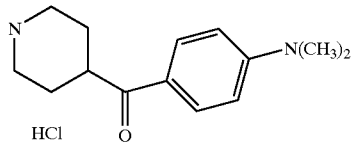 |  | |
| 132 | 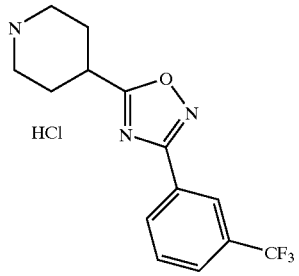 |  | |
| 133 | 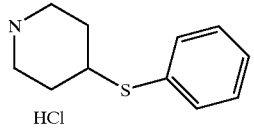 |  | 516 |

-continued
| | | | |
|---|---|---|---|
| 134 | 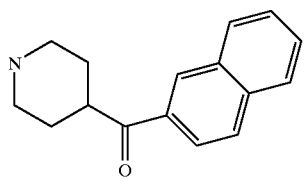 |  | |
| 135 | 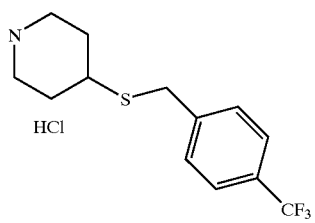 |  | |
| 136 | 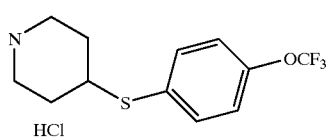 |  | 600 |
| 137 | 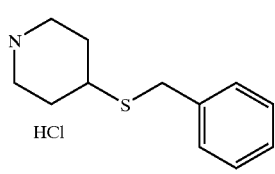 |  | 530 |
| 138 | 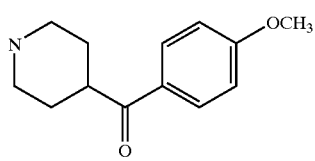 | 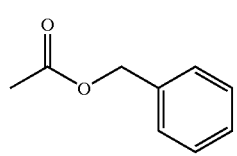 | 636 |
| 139 | 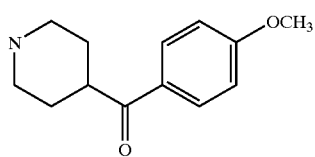 | 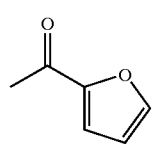 | 596 |
| 140 | 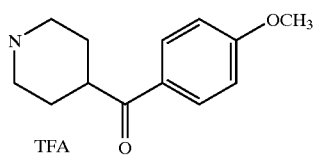 | —H | 502 |
| 141 | 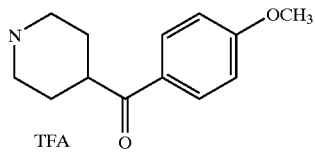 | 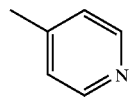 | 579 |
| 142 | 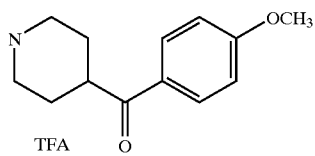 |  | 542 |

-continued
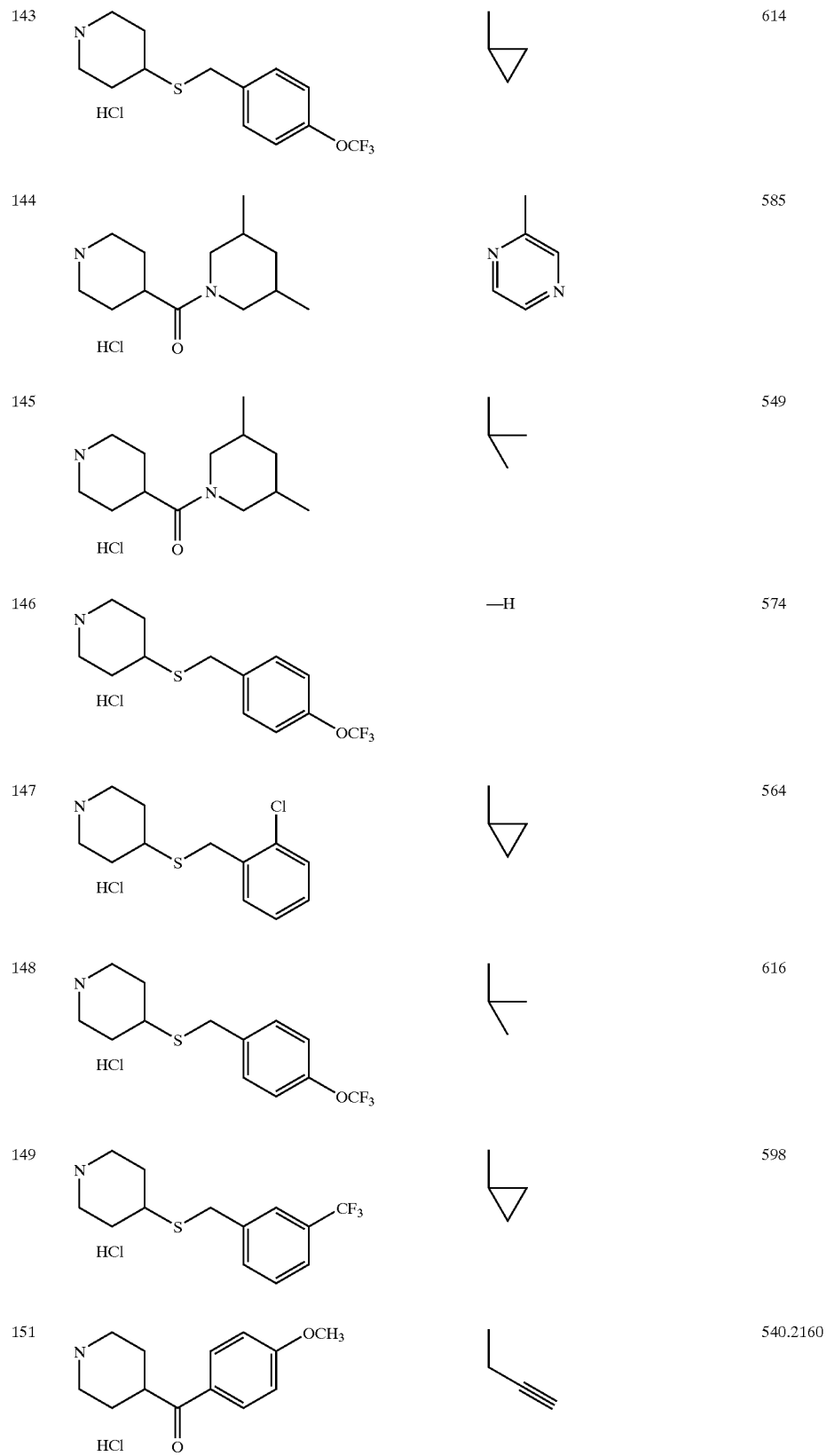

-continued
| | | | |
|---|---|---|---|
| 152 | 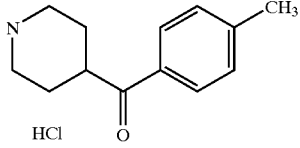 HCl |  | 524.225 |
| 153 | 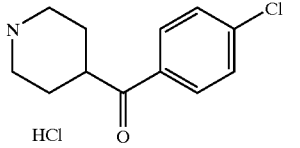 HCl |  | 544.1673 |
| 154 | 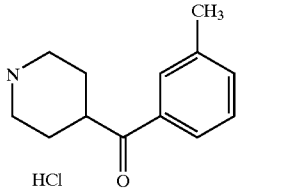 HCl |  | 524.2218 |
| 155 | 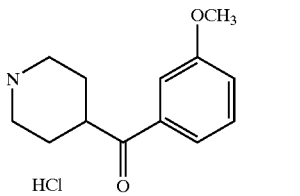 HCl | 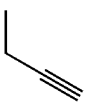 | 540.2155 |
| 156 | 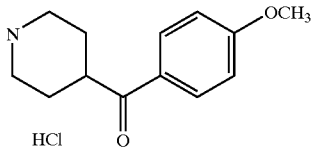 HCl | 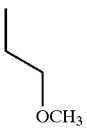 | 560.2387 |
| 157 | 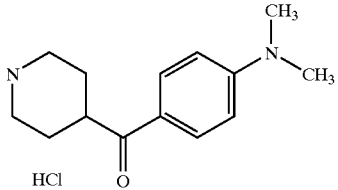 HCl |  | 555.2666 |
| 158 | 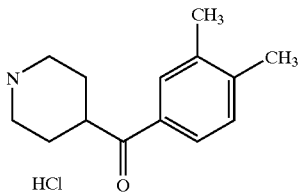 HCl |  | 540.2548 |
| 159 | 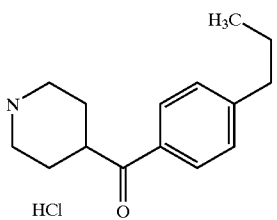 HCl | 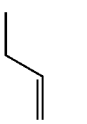 | 554.2698 |

-continued
| | | | |
|---|---|---|---|
| 160 | 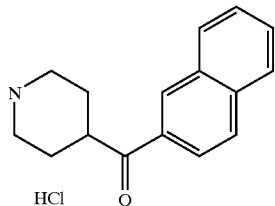 HCl | 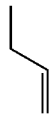 | 562.2378 |
| 161 | 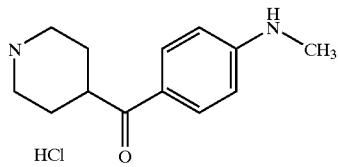 HCl | 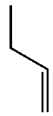 | 541.2488 |
| 162 | 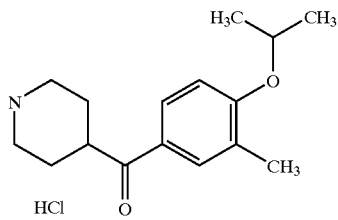 HCl | 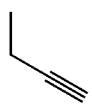 | |
| 163 | 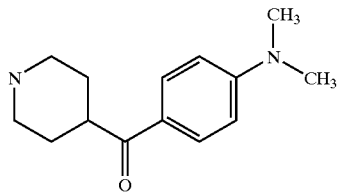 | 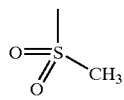 | 593.2131 |
| 164 | 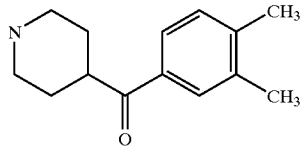 | 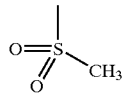 | 578.1976 |
| 165 | 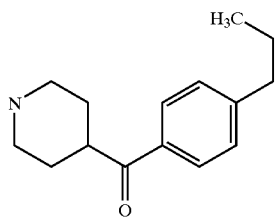 | 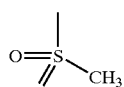 | 592.2151 |
| 166 | 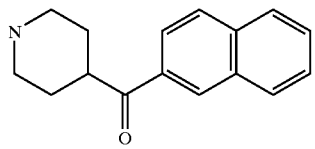 | 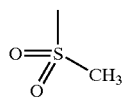 | 600.1865 |
| 167 | 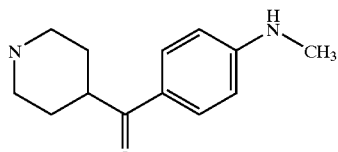 | 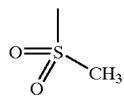 | 579.1984 |

-continued
| | | | |
|---|---|---|---|
| 168 | 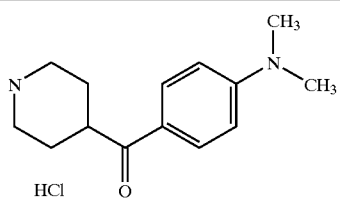 |  | 543.2647 |
| 169 | 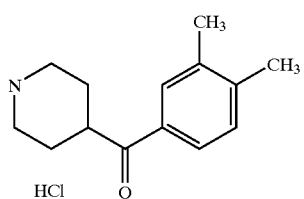 |  | 528.2550 |
| 170 | 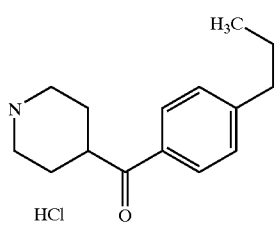 |  | 542.2700 |
| 171 | 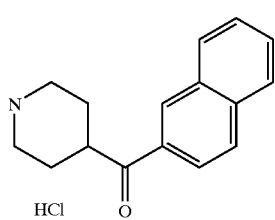 |  | 550.2390 |
| 172 | 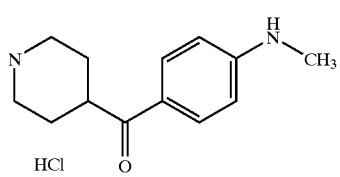 |  | 529.2505 |
| 173 | 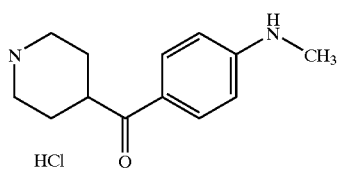 |  | 539.2338 |
| 174 | 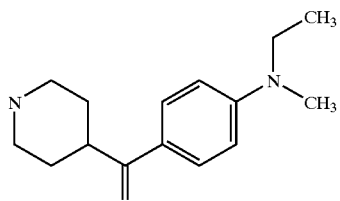 |  | 567.2653 |
| 175 | 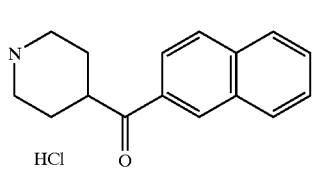 |  | 560.2249 |

-continued
| | | | |
|---|---|---|---|
| 176 |  | | 544.2489 |
| 177 | 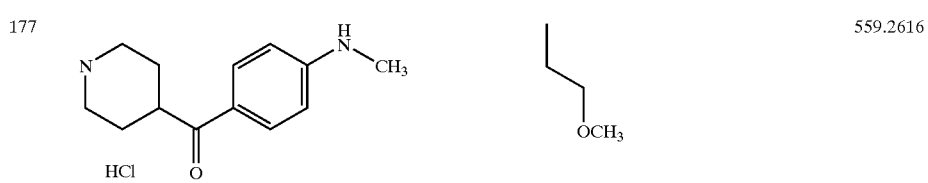 | | 559.2616 |
| 178 | 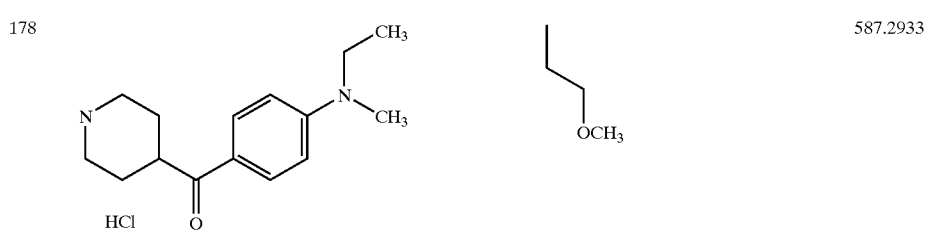 | | 587.2933 |
| 179 |  | | 580.2504 |
| 180 |  | | 546.1840 |
| 181 | 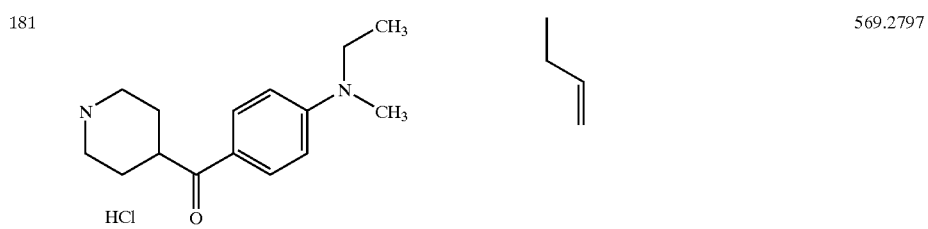 | | 569.2797 |
| 182 | 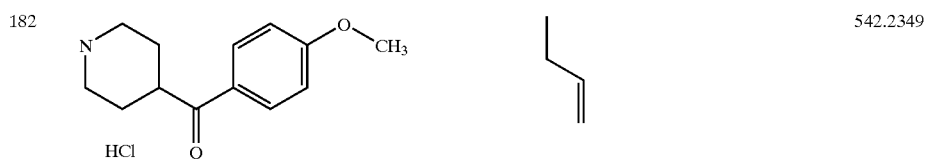 | | 542.2349 |
| 183 | 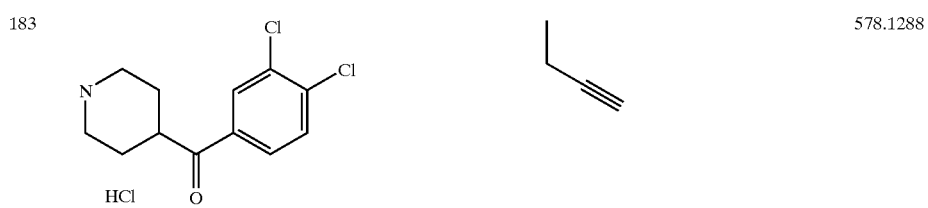 | | 578.1288 |

-continued
| | | | |
|---|---|---|---|
| 184 | 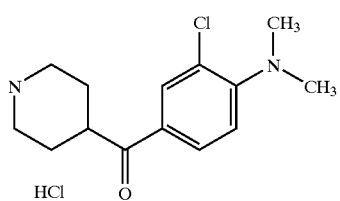 HCl | 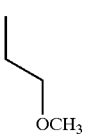 | 607.2381 |
| 185 | 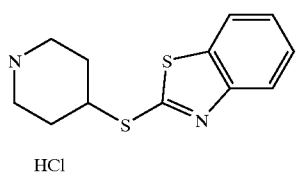 HCl |  | 573.1654 |
| 186 | 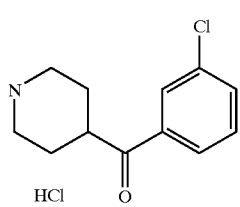 HCl |  | 564.1965 |
| 187 | 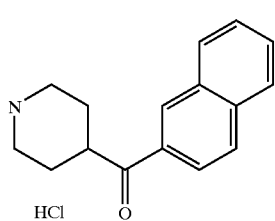 HCl | 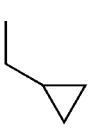 | 576.2552 |
| 188 | 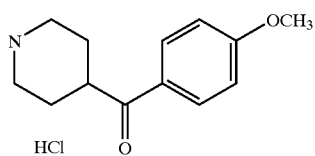 HCl |  | 556.2506 |
| 189 | 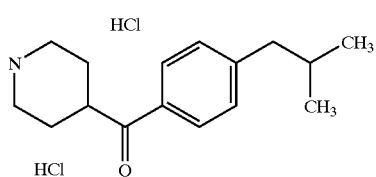 HCl |  | 568.2862 |
| 190 | 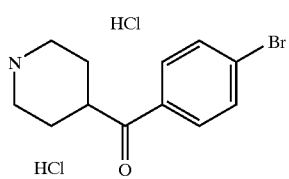 HCl |  | 590 |
| 191 | 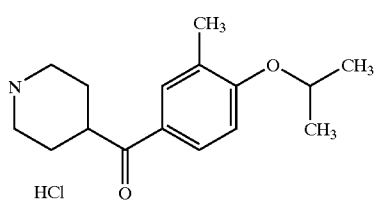 HCl |  | 602.2935 |

-continued

| | | | |
|---|---|---|---|
| 192 | [4-chlorophenyl piperidin-4-yl methanone] | [methylsulfonyl] | 584.1298 |
| 193 | [4-chlorophenyl piperidin-4-yl methanone · HCl] | [propyl, CH₃] | 534.1860 |
| 194 | [4-methoxyphenyl piperidin-4-yl methanone · HCl] | [propyl, CH₃] | 530.2332 |
| 195 | [4-(cyclobutylmethyl)phenyl piperidin-4-yl methanone · HCl] | [propyl, CH₃] | |
| 196 | [4-(cyclobutylmethyl)phenyl piperidin-4-yl methanone · HCl] | [cyclopropyl] | 580.2848 |
| 197 | [4-(cyclopentylmethyl)phenyl piperidin-4-yl methanone · HCl] | [cyclopropyl] | 594.3011 |
| 198 | [4-(cyclohexylmethyl)phenyl piperidin-4-yl methanone · HCl] | [cyclopropyl] | 608.3148 |
| 199 | [4-(2-cyclopentylethyl)phenyl piperidin-4-yl methanone · HCl] | [cyclopropyl] | 608.3152 |
| 200 | [4-(2-methylbutyl)phenyl piperidin-4-yl methanone · HCl] | [cyclopropyl] | 582.2997 |

-continued

| | | | |
|---|---|---|---|
| 201 | piperidine-C(O)-C6H4-CH2-cyclobutyl · HCl · HCl | CH2CH2OCH3 | 598.296 |
| 202 | piperidine-C(O)-C6H4-CH2-cyclopentyl · HCl · HCl | CH2CH2OCH3 | 612.3124 |
| 203 | piperidine-C(O)-C6H4-CH2-cyclohexyl · HCl · HCl | CH2CH2OCH3 | 626.3276 |
| 204 | piperidine-C(O)-C6H4-CH2CH2-cyclopentyl · HCl · HCl | CH2CH2OCH3 | 626.3268 |
| 205 | piperidine-C(O)-C6H4-CH2CH(CH3)CH2CH3 · HCl · HCl | CH2CH2OCH3 | 600.3107 |
| 206 | piperidine-C(O)-C6H4-OCH3 | S(O)2CH3 | 580.1822 |
| 207 | piperidine-C(O)-C6H4-CH3 | S(O)2CH3 | 546.1850 |
| 208 | piperidine-C(O)-C6H4-CH3 · HCl | CH2CH2CH3 | 514.2382 |
| 210 | piperidine-C(O)-C6H4-CH3 · HCl | CH2-cyclopropyl | 540.2539 |

-continued
| | | | |
|---|---|---|---|
| 211 | 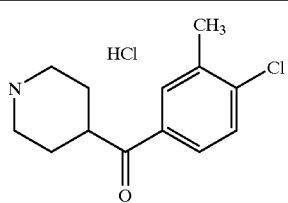 | 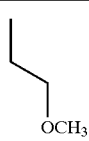 | 578.2106 |
| 212 | 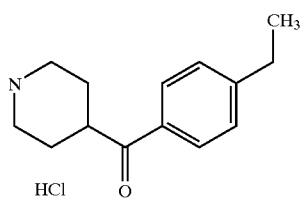 |  | 558.2667 |
| 213 | 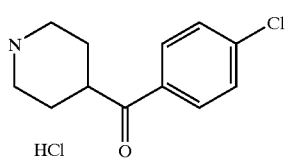 |  | 546.1847 |
| 214 | 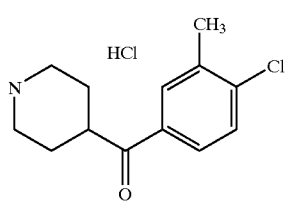 |  | 560.2012 |
| 215 | 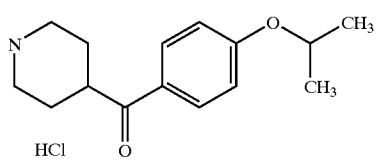 |  | 570.2608 |
| 216 | 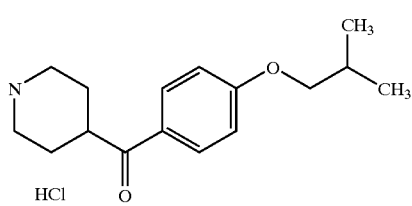 |  | 584.2755 |
| 217 | 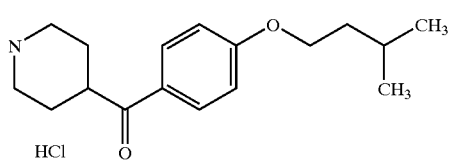 |  | 598.2953 |
| 218 | 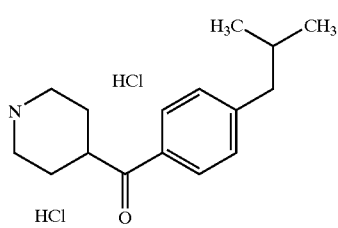 |  | 586 |

-continued
| | | | |
|---|---|---|---|
| 219 | 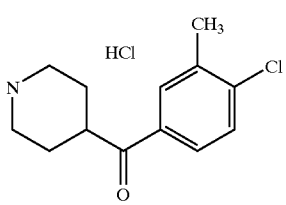 | 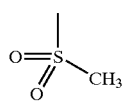 | 598.1441 |
| 220 | 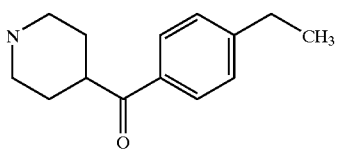 | 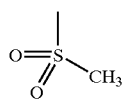 | 578.1966 |
| 221 | 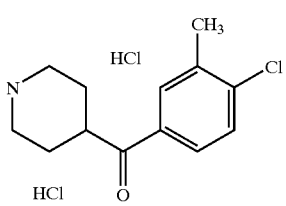 |  | 548.1988 |
| 222 | 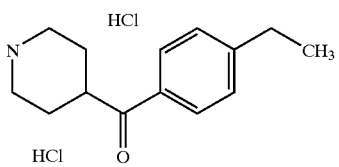 |  | 528.2543 |
| 223 | 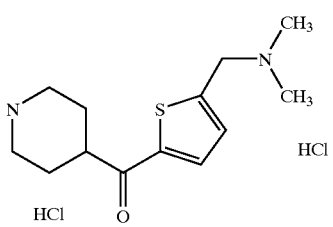 |  | 593.2431 |
| 224 | 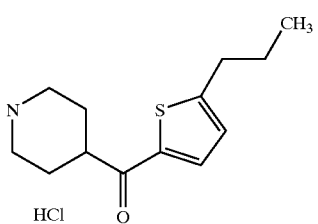 |  | 578.2359 |
| 225 | 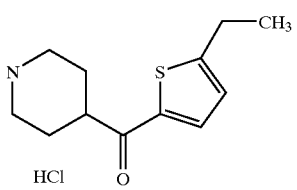 |  | 564.2202 |

| | | | -continued |
|---|---|---|---|
| 226 | 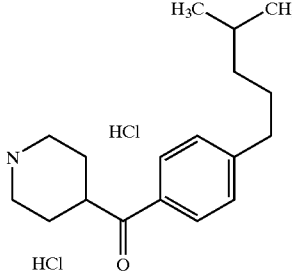 | 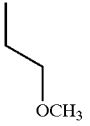 | 614.3261 |
| 227 | 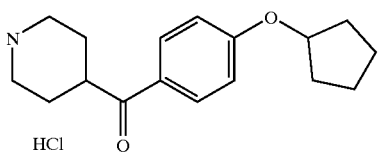 | 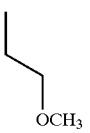 | 614.2932 |
| 228 | 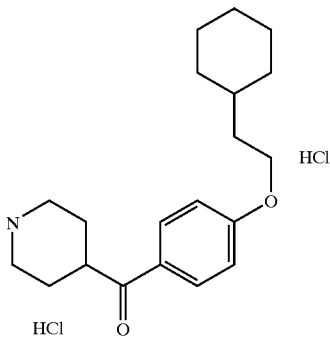 |  | 656.3399 |
| 229 | 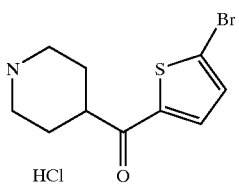 |  | |
| 230 | 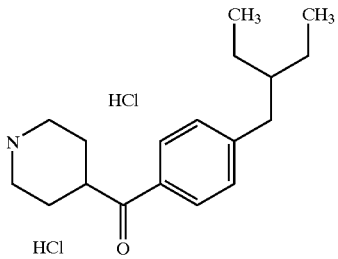 | 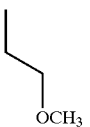 | 614.3273 |
| 231 | 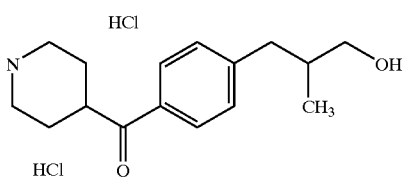 | 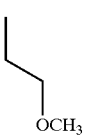 | 602.2901 |
| 232 | 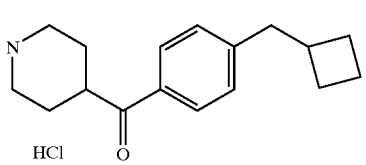 | 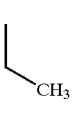 | 568.2876 |

-continued
| | | | |
|---|---|---|---|
| 233 | 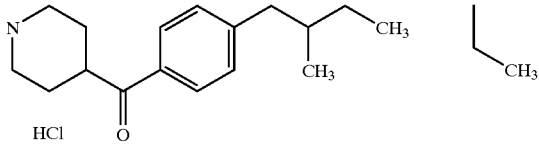 |  | 570.2970 |
| 234 | 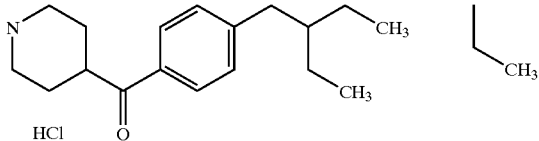 |  | 584.3166 |
| 235 | 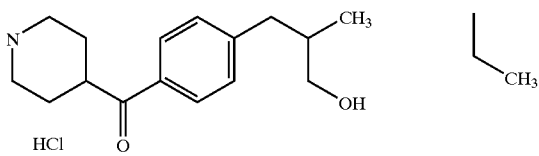 |  | 572.2787 |
| 236 | 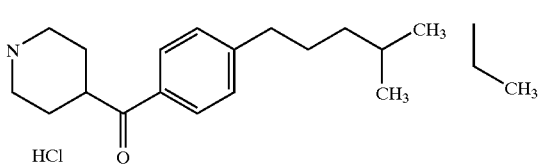 |  | 584.3161 |
| 237 | 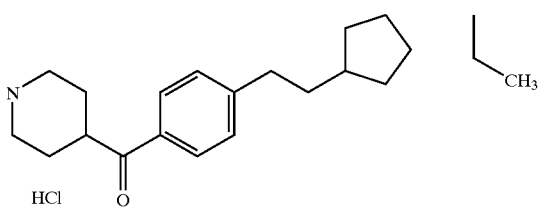 |  | 596.3014 |
| 238 | 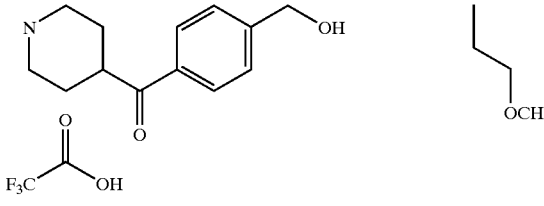 | 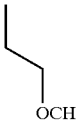 | 560.2437 |
| 239 | 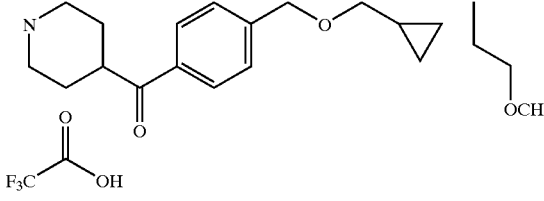 |  | 614.2883 |
| 240 | 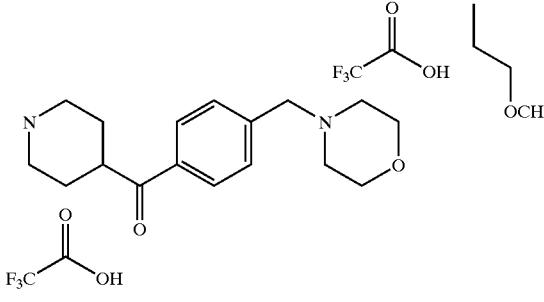 |  | 629.3014 |

-continued
| | | | |
|---|---|---|---|
| 242 | 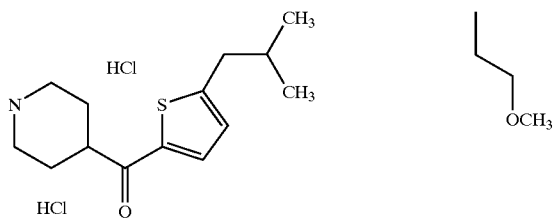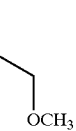 | 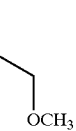 | |
| 243 | 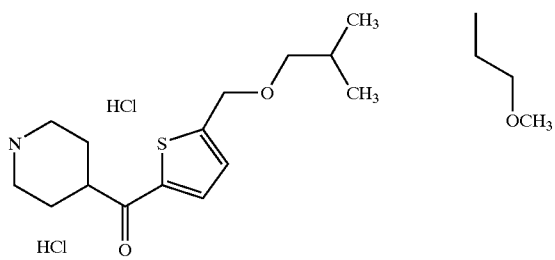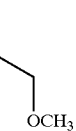 | 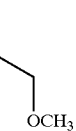 | 622.2636 |
| 244 | 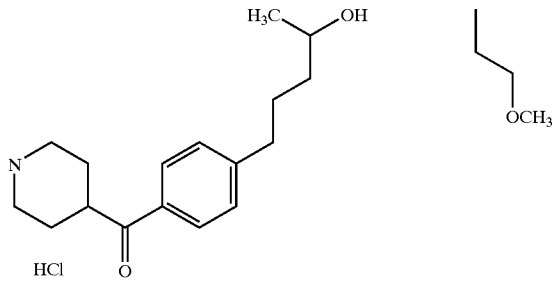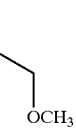 | 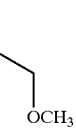 | 616.3040 |
| 245 | 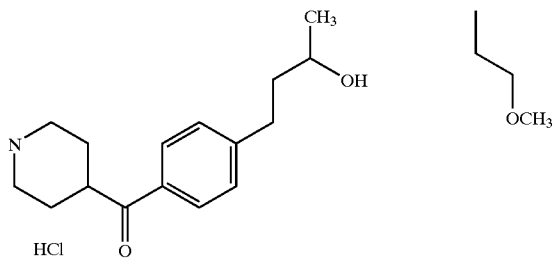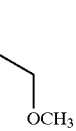 | 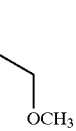 | 602.2876 |
| 246 | 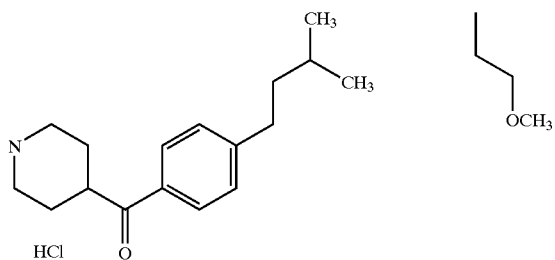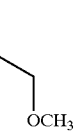 | 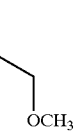 | 600.3109 |
| 247 | 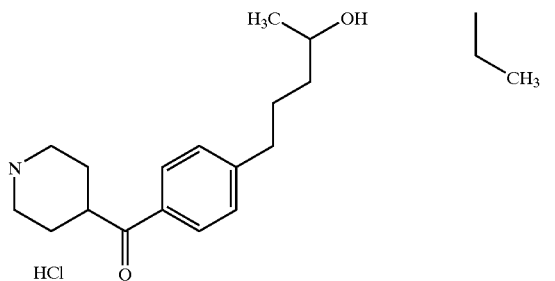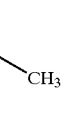 | 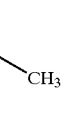 | 586.2949 |

-continued
| | | | |
|---|---|---|---|
| 248 | 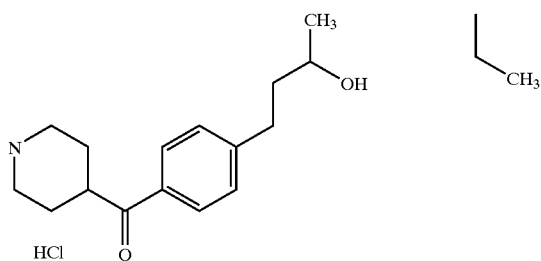 | CH₃ | 572.2778 |
| 249 | 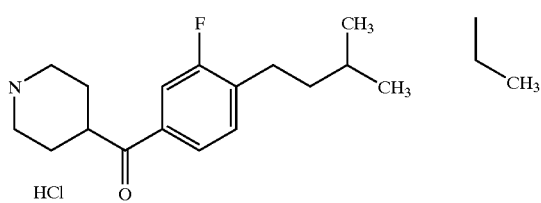 | CH₃ | 570.3007 |
| 250 | 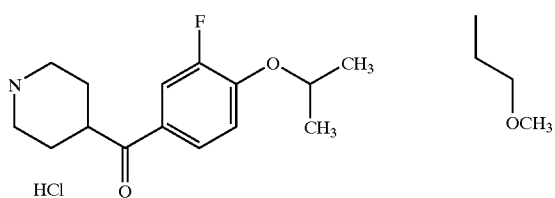 | OCH₃ | 606.2664 |
| 252 | 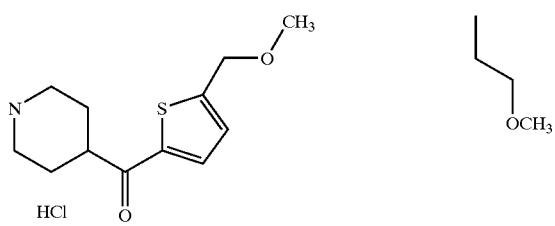 | OCH₃ | 580.2147 |
| 253 | 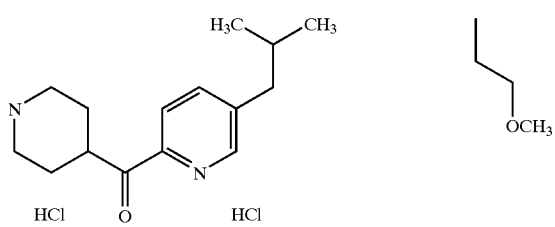 | OCH₃ | 587.2914 |
| 254 | 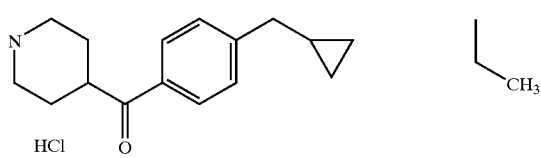 | CH₃ | 554.5692 |
| 256 | 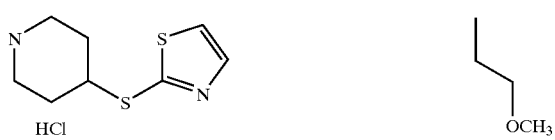 | OCH₃ | 541.1650 |

-continued
| | | | |
|---|---|---|---|
| 257 | 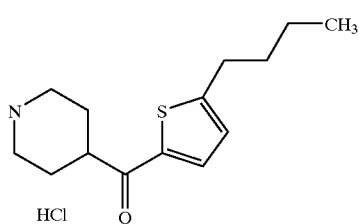 HCl |  | 574.2388 |
| 258 | 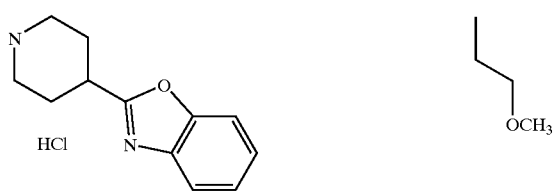 HCl | 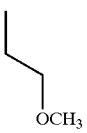 OCH₃ | 543.2291 |
| 259 | 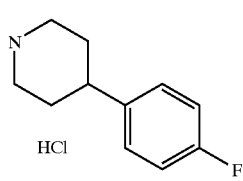 HCl F |  | 500.2019 |
| 260 | 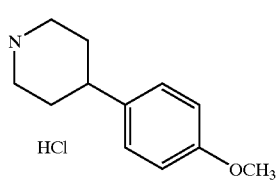 HCl OCH₃ |  | 514.2376 |
| 261 | 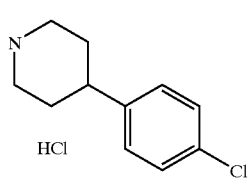 HCl Cl |  | 516.1723 |
| 262 | 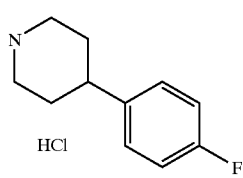 HCl F | 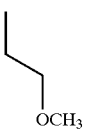 OCH₃ | 518.2130 |
| 263 | 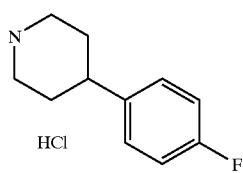 HCl F | 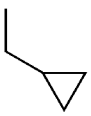 | 514.2194 |
| 264 | 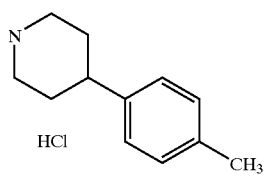 HCl CH₃ | 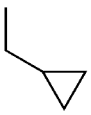 | 518.2432 |

-continued
| | | | |
|---|---|---|---|
| 265 | 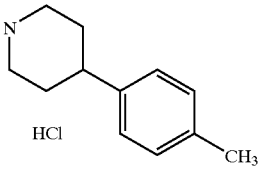 | 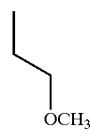 | 514.2375 |
| 266 | 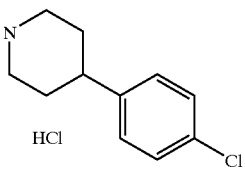 | 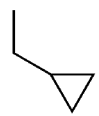 | 530.1880 |
| 267 | 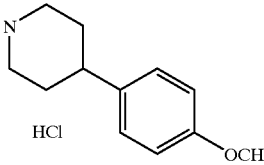 | 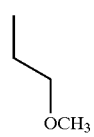 | 532.2307 |
| 268 | 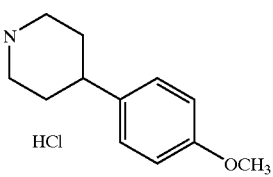 | 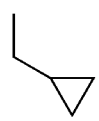 | 528.2557 |
| 269 | 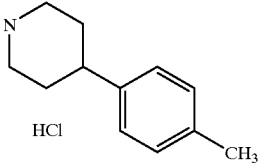 | 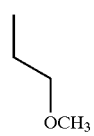 | 516.2557 |
| 270 | 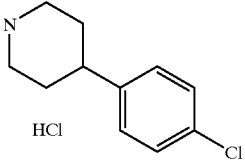 |  | 518.1880 |
| 271 | 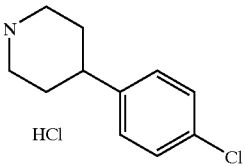 |  | 536.1979 |
| 272 | 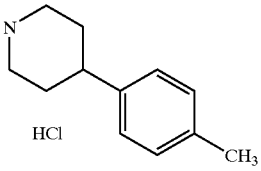 |  | 498.2450 |

-continued
| | | | |
|---|---|---|---|
| 273 | 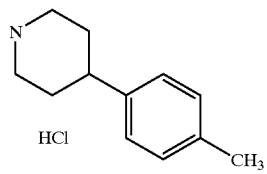 |  | 512.2615 |
| 274 | 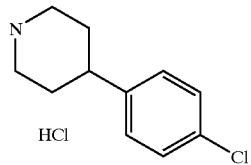 |  | 532.2061 |
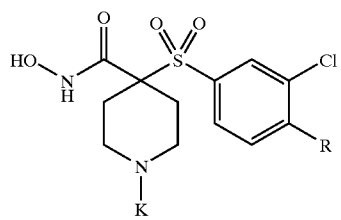
| Example | R | K | MS (ES) m/z |
|---|---|---|---|
| 275 | 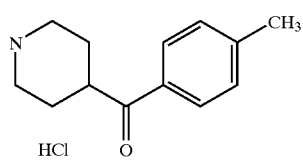 | 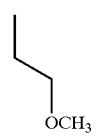 | 578.2068 |
| 276 | 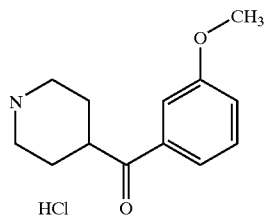 |  | 594.2005 |
| 277 | 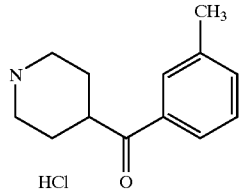 | 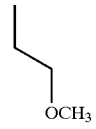 | 578.2053 |
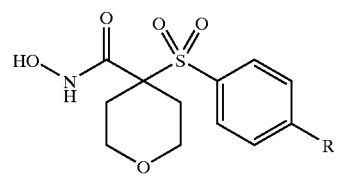
| Example | R | MS (ES) m/z |
|---|---|---|

-continued
| | | |
|---|---|---|
| 278 |  | 463.1704 |
| 279 | 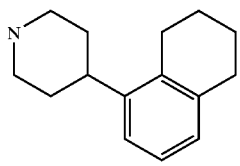 | 499.2304 |
| 280 | 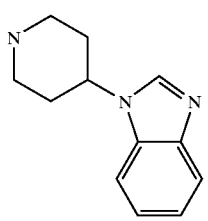 | |
| 281 | 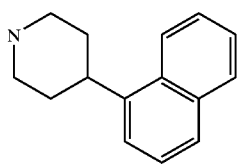 | 495.4984 |
| 282 | 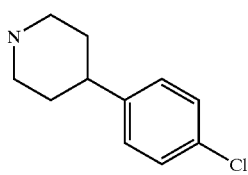 | 479.1416 |
| 283 | 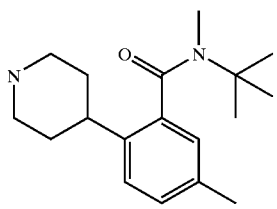 | 572.2800 |
| 284 | 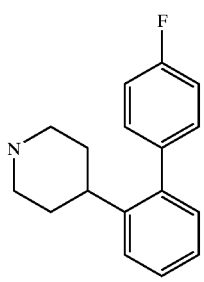 | 539.2017 |

-continued
| | | |
|---|---|---|
| 285 | 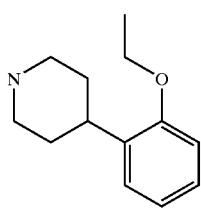 | 489.2049 |
| 286 | 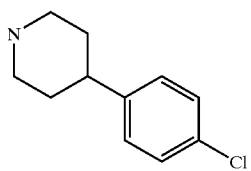 | 477 |
| 287 | 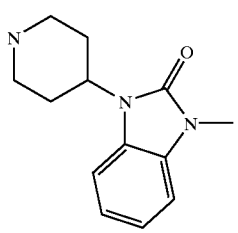 | 515 |
| 288 | 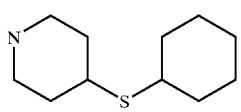 | 483.1992 |
| 289 | 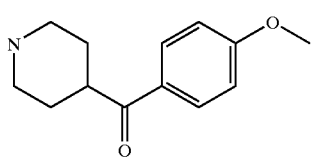 | 503 |
| 290 | 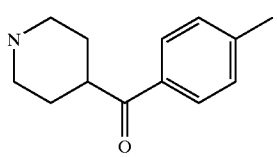 | 487 |
| 291 | 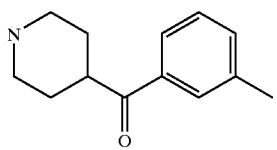 | 487 |
| 292 | 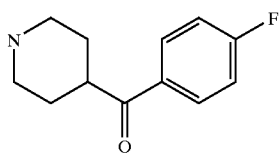 | 491 |
| 293 | 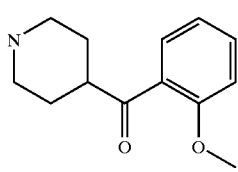 | 503 |

-continued
| | | |
|---|---|---|
| 294 | 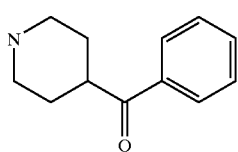 | 473 |
| 295 | 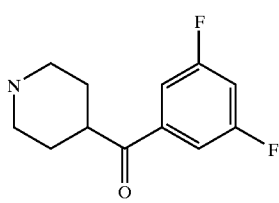 | 509 |
| 296 | 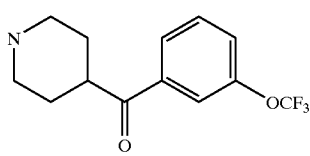 | 557 |
| 297 | 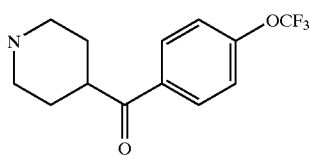 | 557 |
| 298 | 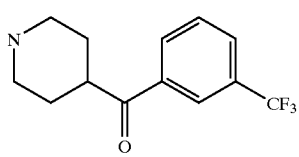 | 541 |
| 299 | 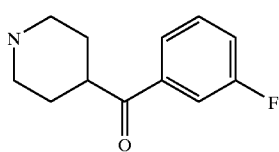 | 491 |
| 300 | 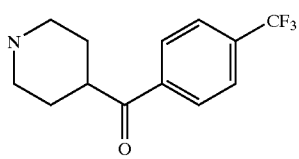 | 541 |
| 301 | 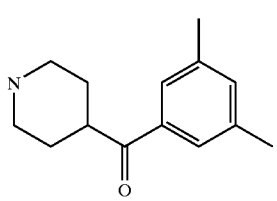 | 501 |
| 302 | 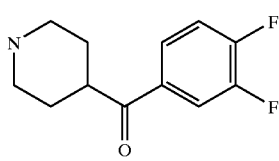 | 509 |

-continued

| | | |
|---|---|---|
| 303 | [piperidine-C(O)-phenyl-ethyl (3-ethyl)] | 501 |
| 304 | [piperidine-C(O)-phenyl-ethyl (4-ethyl)] | 501 |
| 305 | [piperidine-C(O)-phenyl (4-OCH₃, 3-CH₃)] | 517 |
| 306 | [piperidine-C(O)-phenyl (4-OCH₃, 3-F)] | 521 |
| 307 | [piperidine-C(O)-phenyl (4-CH₃, 3-F)] | 505 |
| 308 | [piperidine-C(O)-phenyl (3,4-diCH₃)] | 501 |
| 309 | [piperidine-C(O)-phenyl (4-CF₃, 3-F)] | 559 |
| 310 | [piperidine-C(O)-phenyl (4-N(CH₃)₂)] | 501 |
| 311 | [piperidine-C(O)-phenyl (3-vinyl)] | 499 |

-continued
| | | |
|---|---|---|
| 312 | 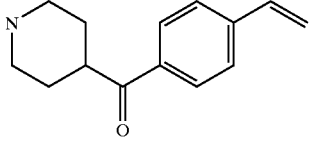 | 499 |
| 313 | 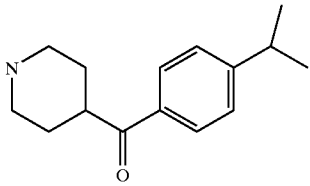 | 515 |
| 314 | 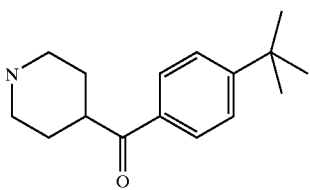 | 529 |
| 315 | 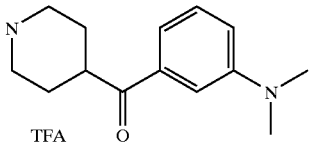
TFA | 516 |
| 316 | 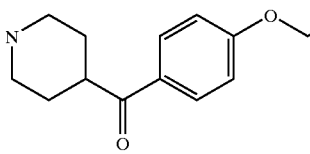 | 517 |
| 317 | 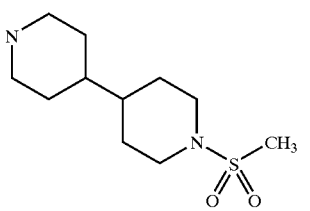 | |
| 318 | 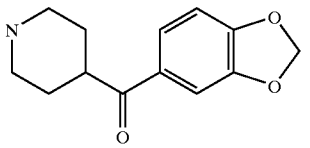 | 517 |
| 319 | 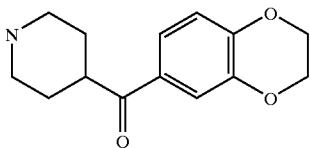 | |
| 320 | 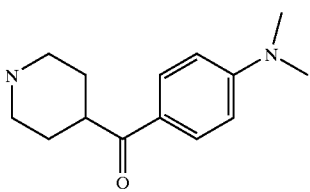 | |

-continued
321 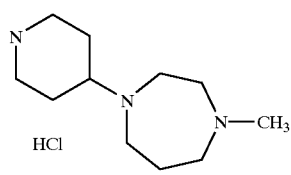
HCl
322 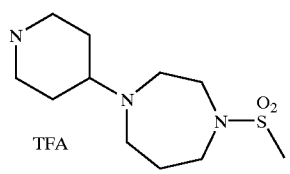
TFA
323 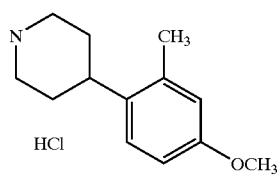
HCl
324 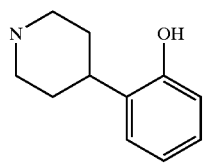
325 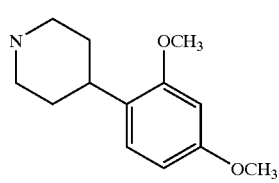
326 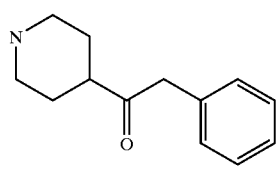
327 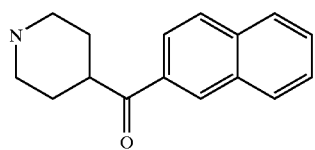
328 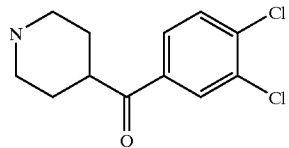
329 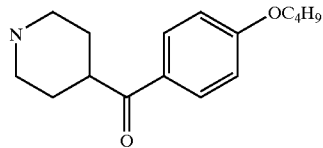

-continued
| | | |
|---|---|---|
| 330 | 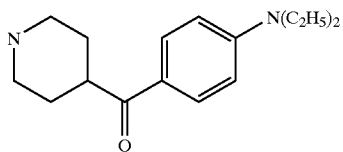 | |
| 331 | 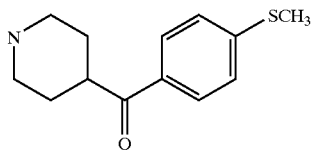 | |
| 332 | 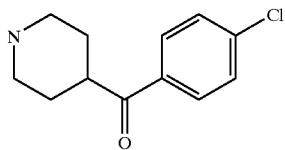 | |
| 333 | 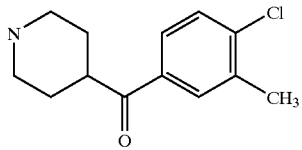 | |
| 334 | 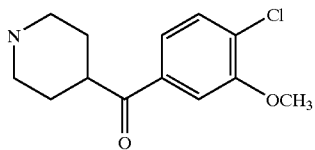 | |
| 335 | 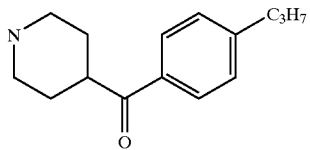 | |
| 336 | 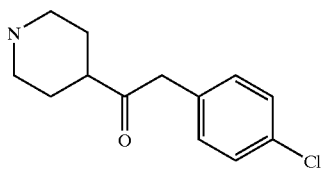 | |
| 337 | 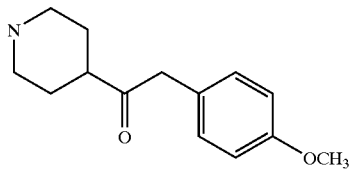 | |
| 338 | 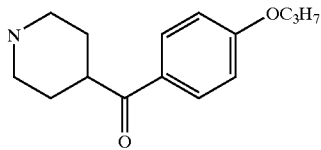 | |

-continued
339
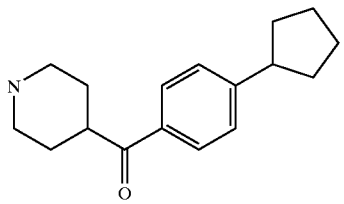
340
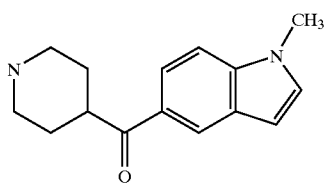
341
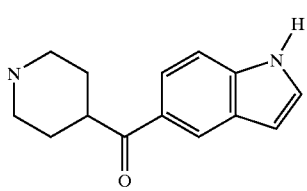
342
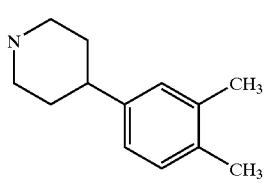
343
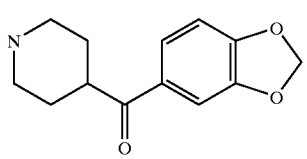
344
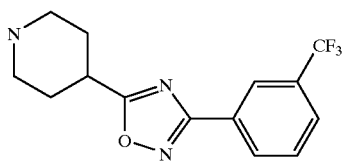
345
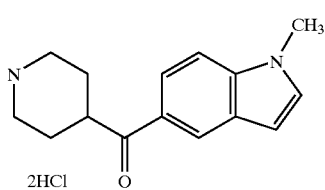
2HCl
346
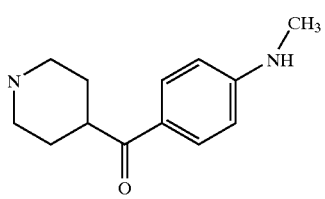

-continued
437 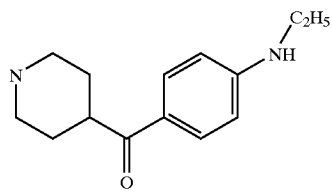
348 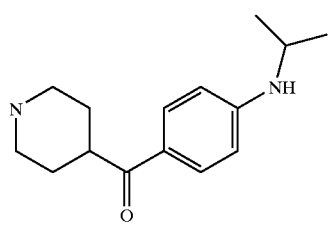
349 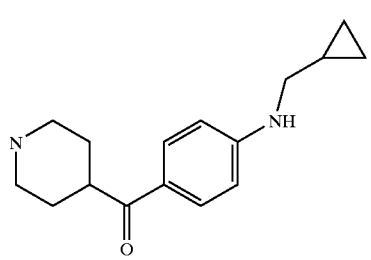
350 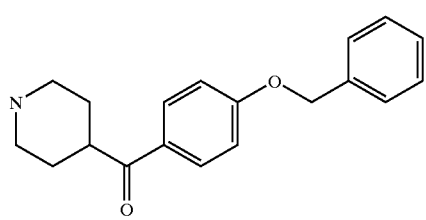
351 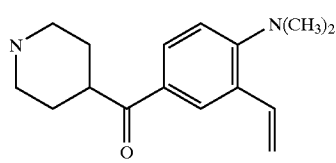
352 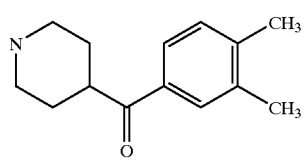
353 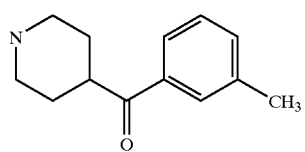
354 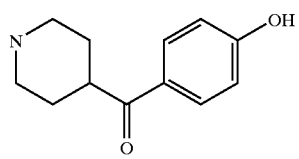

-continued
| | |
|---|---|
| 355 | 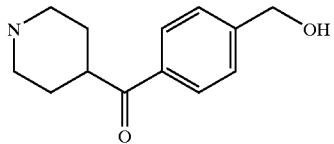 |
| 356 | 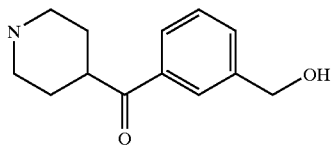 |
| 357 | 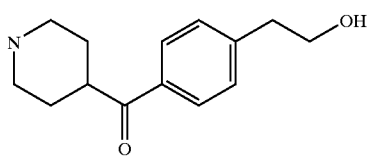 |
| 358 | 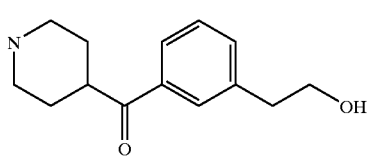 |
| 359 | 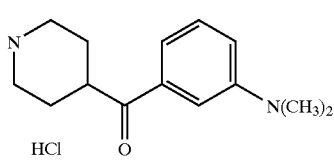 |
| 360 | 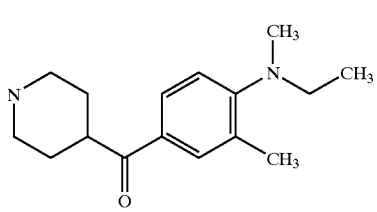 |
| 361 | 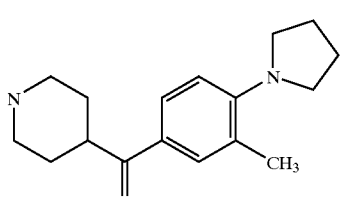 |
| 362 | 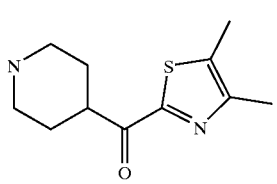 |
| 363 | 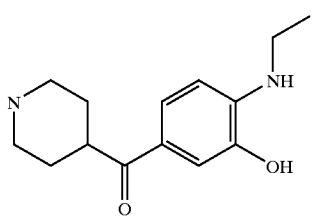 |

| | |
|---|---|
| 364 | 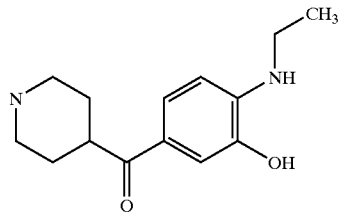 |
| 365 | 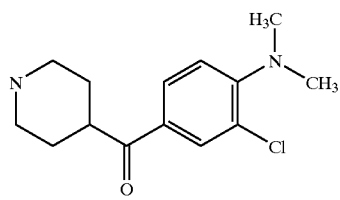 |
| 366 | 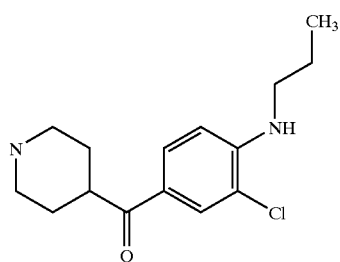 |
| 367 | 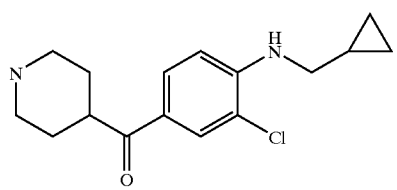 |
| 368 | 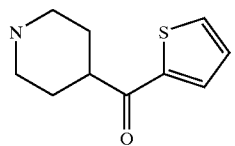 |
| 369 | 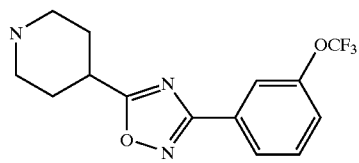 |
| 370 | 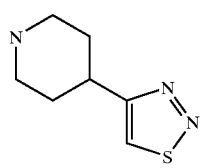 |
| 371 | 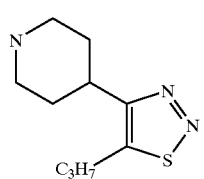 |

-continued
| | | |
|---|---|---|
| 372 | 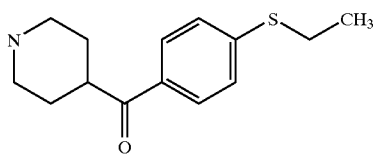 | |
| 373 | 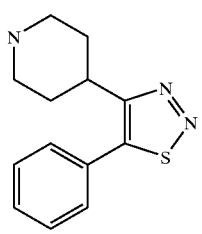 | |
| 374 | 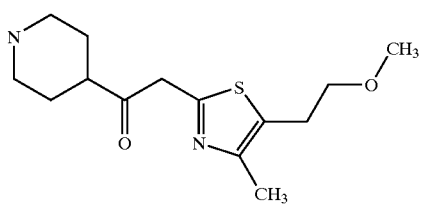 | |
| 375 | 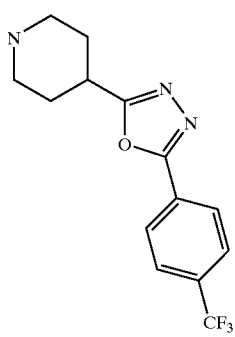 | 581 |
| 376 | 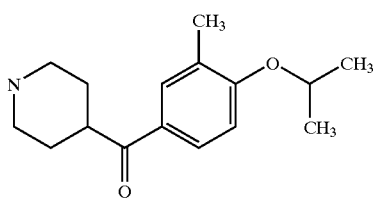 | 545.2320 |
| 377 | 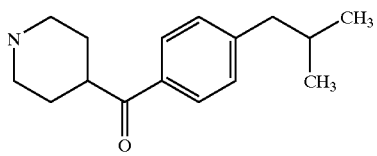 | 529.2383 |
| 378 | 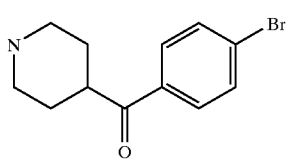 | 551.0854 |

-continued
| | | |
|---|---|---|
| 379 | 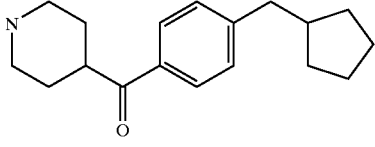 | 555.252 |
| 380 | 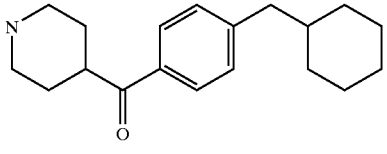 | 569.2687 |
| 381 | 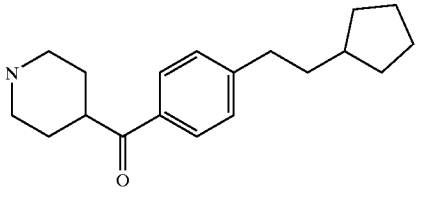 | 569.2676 |
| 382 | 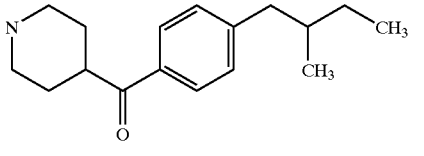 | 543.2524 |
| 383 | 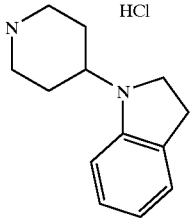 | |
| 384 | 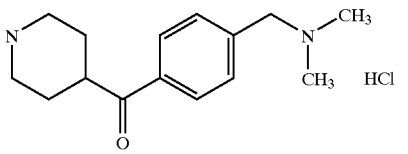 | 530.2315 |
| 385 | 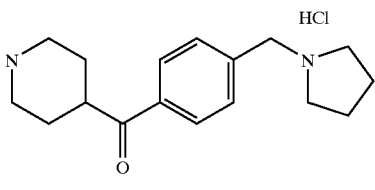 | 556.2482 |
| 386 | 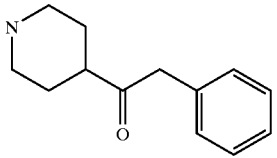 | |
| 387 | 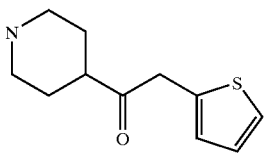 | |

Example 388

In Vitro Metalloprotease Inhibition

Several hydroxamates and salts thereof were assayed for MMP inhibition activity by an in vitro assay generally following the procedures outlined in Knight et al., *FEBS Lett.*, 296(3), 263 (1992).

Recombinant human MMP-1, MMP-2, MMP-9, MMP-13, and MMP-14 were used in this assay. These enzymes were prepared in the Assignee's laboratories following usual laboratory procedures. Specifics for preparing and using these enzymes can be found in the scientific literature describing these enzymes, See, e.g., *Enzyme Nomenclature* (Academic Press, San Diego, Calif., 1992) (and the citations therein). See also, Frije et al., *J Biol. Chem.*, 26(24), 16766–73 (1994).

The MMP-1 was obtained from MMP-1 expressing transfected HT-1080 cells provided by Dr. Harold Welgus of Washington University in St. Louis, Mo. The MMP-1 was activated using 4-aminophenylmercuric acetate (APMA), and then purified over a hydroxamic acid column.

The MMP-2 was obtained from MMP-2 expressing transfected cells provided by Dr. Gregory Goldberg of Washington University.

The MMP-9 was obtained from MMP-9 expressing transfected cells provided by Dr. Gregory Goldberd.

The MMP-13 was obtained as a proenzyme from a full-length cDNA clone using baculovirus, as described by V. A. Luckow, "Insect Cell Expression Technology," *Protein Engineering: Principles and Practice*, pp. 183–218 (edited by J. L. Cleland et al., Wiley-Liss, Inc., 1996). The expressed proenzyme was first purified over a heparin agarose column, and then over a chelating zinc chloride column. The proenzyme was then activated by APMA for use in the assay. Further details on baculovirus expression systems may be found in, for example, Luckow et al., *J. Virol.*, 67, 4566–79 (1993). See also, O'Reilly et al, *Baculovirus Expression Vectors: A Laboratory Manual* (W. H. Freeman and Co., New York, N.Y., 1992). See also, King et al., *The Baculovirus Expression System: A Laboratory Guide* (Chapman & Hall, London, England, 1992).

The enzyme substrate was a methoxycoumarin-containing polypeptide having the following sequence:

MCA-ProLeuGlyLeuDpaAlaArgNH$_2$

Here, "MCA" is methoxycoumarin and "Dpa" is 3-(2,4-dinitrophenyl)-L-2,3-diaminopropionyl alanine. This substrate is commercially available from Baychem (Redwood City, Calif.) as product M-1895.

The subject hydroxamate (or salt thereof) was dissolved at various concentrations using 1% dimethyl sulfoxide (DMSO) in a buffer containing 100 mM Tris-HCl, 100 mM NaCl, 10 mM CaCl$_2$, and 0.05% polyethyleneglycol (23) lauryl ether at a pH of 7.5. These solutions were then compared to a control (which contained equal amount of DMSO/buffer solution, but no hydroxamate compound) using Microfluor™ White Plates (Dynatech, Chantilly, Va.). Specifically, The MMPs were activated with APMA or trypsin. Then the various hydroxamate/DMSO/buffer solutions were incubated in separate plates at room temperature with the activated MMP and 4 um of the MMP substrate. The control likewise was incubated at room temperature in separate plates with the MMP and 4 uM of the MMP substrate. In the absence of inhibitor activity, a fluorogenic peptide was cleaved at the gly-leu peptide bond of the substrate, separating the highly fluorogenic peptide from a 2,4-dinitrophenyl quencher, resulting in an increase of fluoresent intensity (excitation at 328 nm/emission at 415). Inhibition was measured as a reduction in fluorescent intensity as a function of inhibitor concentration using a Perkin Elmer (Norwalk, Conn.) L550 plate reader. The IC$_{50}$'s were the calculated from these measurements. The results are set forth in the following Table A.

| Inhibition Table A (nM) | | | |
|---|---|---|---|
| Example Number | MMP-13 IC$_{50}$ (nM) | MMP-2 IC$_{50}$ (nM) | MMP-1 IC$_{50}$ (nM) |
| 4 | 15.6 | 2,900 | >10000 |
| 5 | 15.6 | 2,900 | >10000 |
| 6 | 18.1 | >10000 | >10000 |
| 7 | 18.0 | 4,500 | >10000 |
| 8 | 50.0 | 2,500 | >10000 |
| 9 | 12.2 | 5,600 | >10000 |
| 10 | 40.0 | 6,000 | >10000 |
| 11 | 37.0 | 2,700 | >10000 |
| 12 | 6.70 | 1,400 | >10000 |
| 13 | 31.6 | 3,500 | >10000 |
| 14 | 45.0 | >10000 | >10000 |
| 15 | 28.0 | 5,500 | >10000 |
| 16 | 42.5 | 4,800 | >10000 |
| 17 | 70.0 | 7,000 | >10000 |
| 18 | >10000 | >10000 | >10000 |
| 19 | 90.0 | 10,000 | >10000 |
| 20 | 23.5 | 4,500 | >10000 |
| 21 | 6.00 | 1,600 | >10000 |
| 22 | 10.7 | 3,600 | >10000 |
| 23 | 6.40 | 1,600 | >10000 |
| 24 | 6.70 | 700 | >10000 |
| 25 | 4.00 | 445 | >10000 |
| 28 | 10.0 | 800 | >10000 |
| 29 | 20.0 | 4,500 | >10000 |
| 30 | 18.1 | >10000 | >10000 |
| 31 | 15.8 | 2,100 | >10000 |
| 32 | 30.0 | 1,750 | >10000 |
| 33 | 67.4 | 6,000 | 67.4 |
| 34 | 19.3 | 3,700 | >10000 |
| 35 | 26.8 | 900 | >10000 |
| 36 | 70.0 | 5,400 | >10000 |
| 37 | 82.5 | >10000 | >10000 |
| 38 | 17.9 | 5,000 | >10000 |
| 39 | 19.0 | 1,050 | >10000 |
| 40 | 80.0 | 5,700 | >10000 |
| 41 | 11.4 | 6,000 | >10000 |
| 42 | 20.0 | 6,500 | >10000 |
| 44 | 40.0 | 5,700 | >10000 |
| 45 | 10.0 | >10000 | >10000 |
| 46 | 20.0 | 2,000 | >10000 |
| 47 | 4.10 | 562 | >10000 |
| 48 | 0.2 | 0.3 | 3,000 |
| 49 | 2.00 | 59.0 | >10000 |
| 50 | 50.0 | 5,000 | >10000 |
| 51 | 2.20 | 0.45 | >10000 |
| 52 | 32.6 | 900 | >10000 |
| 53 | 27.8 | 7,000 | >10000 |
| 58 | 28.8 | 900 | >10000 |
| 59 | 110 | 1,000 | >10000 |
| 60 | 11.4 | 1,200 | >10000 |
| 70 | 43.5 | 2,050 | >10000 |
| 72 | 80.0 | 10,000 | >10000 |
| 73 | 9.00 | 8,300 | >10000 |
| 74 | 76.9 | 10,000 | >10000 |
| 75 | 4.80 | >10000 | >10000 |
| 76 | 32.7 | 2,700 | >10000 |
| 77 | 160 | >10000 | >10000 |
| 78 | 70.0 | >10000 | >10000 |
| 79 | 37.3 | >10000 | >10000 |
| 80 | 70.0 | >10000 | >10000 |
| 81 | 19.3 | >10000 | >10000 |
| 82 | 20.0 | 7,300 | >10000 |
| 83 | 90.0 | >10000 | >10000 |
| 84 | 105 | >10000 | >10000 |

-continued

Inhibition Table A (nM)

| Example Number | MMP-13 IC$_{50}$ (nM) | MMP-2 IC$_{50}$ (nM) | MMP-1 IC$_{50}$ (nM) |
|---|---|---|---|
| 85  | 14.8 | 9,000  | >10000 |
| 86  | 13.8 | >10000 | >10000 |
| 87  | 130  | >10000 | >10000 |
| 88  | 19.3 | 9,000  | >10000 |
| 89  | 60.0 | >10000 | >10000 |
| 90  | 150  | >10000 | >10000 |
| 91  | 35.0 | >10000 | >10000 |
| 92  | 50.0 | >10000 | >10000 |
| 93  | 50.0 | >10000 | >10000 |
| 95  | 100  | >10000 | >10000 |
| 96  | 63.1 | >10000 | >10000 |
| 97  | 59.1 | >10000 | >1,000 |
| 98  | 50.0 | >10000 | >10000 |
| 99  | 50.0 | >10000 | >10000 |
| 100 | 34.9 | >10000 | >10000 |
| 101 | 40.0 | >10000 | >10000 |
| 102 | 30.6 | 9,000  | >10000 |
| 103 | 37.3 | >10000 | >10000 |
| 104 | 90.0 | >10000 | >10000 |
| 105 | 175  | >10000 | >10000 |
| 106 | 115  | >10000 | >10000 |
| 107 | 30.6 | 7,000  | >10000 |
| 108 | 28.6 | >10000 | >10000 |
| 109 | 60.0 | >10000 | >10000 |
| 110 | 40.0 | >10000 | >10000 |
| 111 | 40.0 | 10,000 | >10000 |
| 112 | 48.5 | >10000 | >10000 |
| 113 | 60.0 | 10,000 | >10000 |
| 114 | 120  | >10000 | >10000 |
| 115 | 200  | >10000 | >10000 |
| 116 | 77.0 | >10000 | >10000 |
| 117 | 65.0 | >10000 | >10000 |
| 118 | 420  | >10000 | >10000 |
| 119 | 1.0  | 200    | >10000 |
| 120 | 0.85 (an average of 2 experiments) | 126 (an average of 2 experiments) | >10000 |
| 121 | 0.1  | 58.8   | >10000 |
| 122 | 0.1  | 106.5  |        |
| 123 | 0.1  | 46.3   | >10000 |
| 124 | 0.4  | 56.4   | >10000 |
| 126 | 11.1 | 400    |        |
| 127 | 3.0  | 80.0   |        |
| 128 | 5.5  | 230    |        |
| 129 | 11.4 | 260    |        |
| 130 | 3.0  | 700    | >10000 |
| 132 | 50.0 | 430    |        |
| 133 | 1.7  | 16.1   | >10000 |
| 134 | 4.5  | 427    | >10000 |
| 135 | 0.5  | 8.0    |        |
| 136 | 50.4 | 246    | >10000 |
| 137 | 0.7  | 4.5    | >10000 |
| 138 | 5.9  | 1500   | >10000 |
| 139 | 1.8  | 330    | >10000 |
| 140 | 18.1 | 800    | >10000 |
| 141 | 1.4  | 160    | >10000 |
| 142 | 6.0  | 420    | >10000 |
| 143 | 2.1  | 100    | >10000 |
| 145 | 210  | 2100   | >10000 |
| 146 | 4.0  | 200    | >10000 |
| 147 | 20.0 | 145    | >10000 |
| 148 | 2.9  | 80.0   | >10000 |
| 149 | 16.9 | 210    | >10000 |
| 151 | 1.3  | 127.6  | >10000 |
| 152 | 0.6  | 56.3   | >10000 |
| 153 | 0.2  | 30.6   | >10000 |
| 154 | 2.4  | 176.5  | >10000 |
| 155 | 1.4  | 43.8   | >10000 |
| 156 | 0.7  | 1335.9 | >10000 |
| 157 | 2.7  | 781.6  | >10000 |
| 158 | 2.4  | 217.8  | >10000 |
| 159 | 0.5  | 32.2   |        |
| 160 | 0.4  | 197.5  | >10000 |
| 161 | 0.3  | 234.7  |        |
| 162 | 2.7  | 494.6  | >10000 |
| 163 | 3.4  | 3231.9 | >10000 |
| 164 | 5.4  | 942.3  | >10000 |
| 165 | 85.9 | 1754   |        |
| 166 | 438  | >10000 |        |
| 167 | 4.7  | 2949   |        |
| 168 | 2.1  | 2181.2 | >10000 |
| 169 | 2.6  | 1061.7 |        |
| 170 | 1.3  | 134.1  | >10000 |
| 171 | 1.9  | 405.4  | >10000 |
| 172 | 3.1  | 649.1  |        |
| 173 | 0.9  | 117.3  |        |
| 174 | 1.1  | 1069.1 | >10000 |
| 175 | 0.7  | 136.6  | >10000 |
| 176 | 0.4  | 122.3  | >10000 |
| 177 | 1.4  | 166.8  |        |
| 178 | 3.0  | 1976.5 |        |
| 179 | 0.7  | 161.3  | >10000 |
| 180 | 0.3  | 52.7   | >10000 |
| 181 | 2.3  | 935.7  | >10000 |
| 182 | 1.1  | 115.4  | >10000 |
| 183 | 0.7  | 37.9   | >10000 |
| 184 | 1.5  | 360.2  | >10000 |
| 185 | 5.1  | 87.4   | >10000 |
| 186 | 3.5  | 94.4   | >10000 |
| 187 | 2.7  | 242.4  | >10000 |
| 188 | 2.0  | 249.9  | >10000 |
| 189 | <0.1 | 258    | >10000 |
| 190 | 0.2  | 23.1   | >10000 |
| 191 | 3.0  | 2286.9 | >10000 |
| 192 | 1.3  | 103.3  | >10000 |
| 193 | 0.4  | 98.7   | >10000 |
| 194 | 9.1  | 1229.7 | >10000 |
| 195 | 0.3  | 462.8  | >10000 |
| 196 | 1.0  | 750.1  | >10000 |
| 197 | 1.4  | 1720.1 | >10000 |
| 198 | 12.0 | 2565.6 |        |
| 199 | 11.7 | 3390.0 | >10000 |
| 200 | 0.5  | 1398.8 | >10000 |
| 201 | 0.2  | 6315.4 | >10000 |
| 202 | 0.4  | 1017.6 | >10000 |
| 203 | 0.6  | 816.4  | 2367   |
| 204 | 0.2  | 1045.8 | >10000 |
| 205 | <0.1 | 411.5  | >10000 |
| 206 | 1.8  | 199.4  | >10000 |
| 207 | 1.1  | 4.4    | >10000 |
| 208 | 0.1  | 19.6   | >10000 |
| 210 | 1.1  | 13.1   | >10000 |
| 211 | 1.2  | 122.3  | >10000 |
| 212 | 0.2  | 109.7  | >10000 |
| 213 | 0.5  | 25.8   | >10000 |
| 214 | 1.7  | 159.8  | >10000 |
| 215 | 0.9  | 22.7   | >10000 |
| 216 | 1.5  | 46.4   | >10000 |
| 217 | 1.3  | 270.0  | >10000 |
| 218 | 0.2  | 75.7   | >10000 |
| 219 | 4.9  | 258.2  | >10000 |
| 220 | 1.7  | 289.8  | >10000 |
| 221 | 3.4  | 301.1  | >10000 |
| 222 | 1.0  | 196.6  | >10000 |
| 223 | 2.5  | 80.4   | >10000 |
| 224 | 0.4  | 72.9   | >10000 |
| 225 | 0.2  | 40.8   | >10000 |
| 226 | <0.1 | 1024   | >10000 |
| 227 | 1.4  | 132.1  | >10000 |
| 228 | 19.5 | 154.6  |        |
| 229 | 0.2  | 8.5    | >10000 |
| 230 | 0.1  | 745.0  | >10000 |
| 231 | 0.5  | 39.4   | >10000 |
| 232 | 1.3  | 624.4  | >10000 |
| 233 | 1.2  | 1046.1 | >10000 |
| 234 | 7.5  | 2444.7 | >10000 |
| 235 | 0.8  | 118.0  | >10000 |
| 236 | 1.5  | 1848.4 | >10000 |

-continued

Inhibition Table A (nM)

| Example Number | MMP-13 IC$_{50}$ (nM) | MMP-2 IC$_{50}$ (nM) | MMP-1 IC$_{50}$ (nM) |
|---|---|---|---|
| 237 | 2.1 | 1914.8 | >10000 |
| 238 | 1.8 | 62.1 | |
| 239 | 0.6 | 75.8 | |
| 240 | 2.8 | 86.0 | |
| 242 | 1.0 | 87.5 | |
| 243 | 0.3 | 56.0 | >10000 |
| 244 | 0.2 | 15.2 | |
| 245 | 1.1 | 38.6 | |
| 246 | 1.0 | 2712.9 | >10000 |
| 247 | 0.3 | 111.4 | >10000 |
| 248 | 0.6 | 141.0 | >10000 |
| 249 | 5.8 | >10000 | >10000 |
| 250 | 2.1 | 107.2 | |
| 252 | 0.4 | 14.3 | |
| 253 | 1.7 | 38.7 | >10000 |
| 254 | 1.3 | 132.0 | >10000 |
| 256 | 7.5 | 35.4 | |
| 257 | | | |
| 258 | 14.1 | 45.4 | |
| 259 | 0.4 | 0.6 | |
| 260 | 0.4 | 1.2 | >10000 |
| 261 | 0.8 | 1.0 | |
| 262 | 1.0 | 1.7 | |
| 263 | 1.5 | 2.6 | >10000 |
| 264 | 0.8 | 3.1 | |
| 265 | 0.5 | 3.2 | |
| 266 | 1.7 | 4.5 | |
| 267 | 0.4 | 1.7 | >10000 |
| 268 | 1.2 | 5.0 | >10000 |
| 269 | 1.4 | 4.5 | >10000 |
| 270 | 1.1 | 1.9 | >10000 |
| 271 | 0.8 | 1.7 | >10000 |
| 272 | 1.3 | 5.9 | >10000 |
| 273 | 2.5 | 13.4 | |
| 274 | 2.1 | 5.2 | >10000 |
| 275 | 183.6 | 6736.9 | |
| 276 | 126.7 | 2733.4 | |
| 277 | 274.5 | >10000 | |
| 279 | 160 | 3300 | >10000 |
| 280 | 27.1 | 500 | >10000 |
| 281 | 11.4 | 500 | >10000 |
| 282 | 0.7 | 2.0 | >10000 |
| 284 | 33.7 | 5400 | >10000 |
| 285 | 35.0 | 3100 | >10000 |
| 287 | 70.0 | >10000 | >10000 |
| 288 | 4.4 | 60.7 | >10000 |
| 289 | 6.0 | 160 | >10000 |
| 290 | 0.4 | 82.0 | >10000 |
| 291 | 0.8 | 160 | >10000 |
| 292 | 3.2 | 35.0 | >10000 |
| 293 | 37.3 | 1400 | >10000 |
| 294 | 3.1 | 120 | >10000 |
| 295 | 28.6 | 300 | >10000 |
| 296 | 25.1 | 210 | >10000 |
| 297 | 15.8 | 250 | >10000 |
| 298 | 34.9 | 240 | >10000 |
| 299 | 9.4 | 106 | >10000 |
| 300 | 14.8 | 240 | >10000 |
| 301 | 37 | 3000 | >10000 |
| 302 | 1.9 | 35 | >10000 |
| 303 | 3.1 | 590 | >10000 |
| 304 | 1.6 | 270 | >10000 |
| 305 | 6.0 | 3300 | >10000 |
| 306 | 9.0 | 800 | >10000 |
| 307 | 0.9 | 145 | >10000 |
| 308 | 3.0 | 1280 | >10000 |
| 309 | 22.0 | 270 | >10000 |
| 310 | 6.0 | 4500 | >10000 |
| 311 | 3.7 | 700 | >10000 |
| 312 | 1.2 | 175 | >10000 |
| 313 | 3.0 | 445 | >10000 |
| 314 | 12.2 | 3700 | >10000 |
| 315 | 4.5 | 700 | >10000 |
| 316 | 2.0 | 700 | >10000 |
| 317 | 4.0 | 23.5 | >10000 |
| 318 | 5.7 | 130 | >10000 |
| 319 | 4.0 | 175 | >10000 |
| 320 | 2.3 | 10,000 | >10000 |
| 321 | 200 | 1400 | >10000 |
| 322 | 140 | 1400 | >10000 |
| 323 | 7.0 | 505 | >10000 |
| 324 | 11.3 | 70.0 | >10000 |
| 325 | 11.0 | 1750 | >10000 |
| 326 | 3.0 | 70.0 | >10000 |
| 327 | 5.0 | 4700 | >10000 |
| 328 | 4.5 | 186 | >10000 |
| 329 | 20.0 | 1800 | ND |
| 330 | — | — | ND |
| 331 | 1.2 | 250 | ND |
| 332 | 1.3 | 120 | ND |
| 333 | 3.7 | 600 | >10000 |
| 334 | 5.5 | 440 | ND |
| 335 | 2.7 | 1500 | >10000 |
| 336 | 2.0 | 34.9 | ND |
| 337 | 1.7 | 40.0 | ND |
| 338 | — | — | ND |
| 339 | — | — | ND |
| 340 | 16.5 | 10,000 | >10000 |
| 341 | — | — | ND |
| 342 | 2.0 | 76.9 | ND |
| 374 | 5.6 | 970 | >10000 |
| 375 | 34.4 | 2663 | |
| 376 | 6.4 | 2185.4 | >10000 |
| 377 | 0.4 | 361.4 | >10000 |
| 378 | 0.3 | 28.4 | >10000 |
| 379 | 0.6 | 1266.4 | >10000 |
| 380 | 9.7 | 2287.6 | >10000 |
| 381 | 3.5 | 639.9 | >10000 |
| 382 | 0.3 | 1305.4 | >10000 |
| 383 | 36.9 | 382.4 | |
| 384 | 2.9 | 52.9 | |
| 385 | 3.2 | 34.6 | |
| 386 | 15.2 | 1901.1 | |
| 387 | 4.5 | 344.4 | |

Example 389

In Vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, *A Model of Angiogenesis in the Mouse Cornea;* Kenyon, B M, et al., Investigative Ophthalmology & Visual Science, July 1996, Vol. 37, No. 8.

In this assay, uniformly sized Hydron™ pellets containing bFGF and sucralfate were prepared and surgically implanted into the stroma mouse cornea adjacent to the temporal limbus. The pellets were formed by making a suspension of 20 μL sterile saline containing 10 μg recombinant bFGF, 10 mg of sucralfate and 10 μL of 12 percent Hydron™ in ethanol. The slurry was then deposited on a 10×10 mm piece of sterile nylon mesh. After drying, the nylon fibers of the mesh were separated to release the pellets.

The corneal pocket is made by anesthetizing a 7 week old C57B1/6 female mouse, then proptosing the eye with a jeweler's forceps. Using a dissecting microscope, a central, intrastromal linear keratotomy of approximately 0.6 mm in length is performed with a #15 surgical blade, parallel to the insertion of the lateral rectus muscle. Using a modified cataract knife, a lamellar micropocket is dissected toward the temporal limbus. The pocket is extended to within 1.0 mm of the temporal limbus. A single pellet was placed on the corneal surface at the base of the pocket with a jeweler's forceps. The pellet was then advanced to the temporal end of the pocket. Antibiotic ointment was then applied to the eye.

Mice were dosed on a daily basis for the duration of the assay. Dosing of the animals was based on bioavailability and overall potency of the compound an exemplary dose was 10 or 50 mg/kg (mpk) bid, po. Neovascularization of the corneal stroma begins at about day three and was permitted to continue under the influence of the assayed compound until day five. At day five, the degree of angiogenic inhibition was scored by viewing the neovascular progression with a slit lamp microscope.

The mice were anesthetized and the studied eye was once again proptosed. The maximum vessel length of neovascularization, extending from the limbal vascular plexus toward the pellet was measured. In addition, the contiguous circumferential zone of neovascularization was measured as clock hours, where 30 degrees of arc equals one clock hour. The area of angiogenesis was calculated as follows.

$$area = \frac{(0.4 \times clock\ hours \times 3.14 \times vessel\ length\ (in\ mm))}{2}$$

Five to six mice were utilized for each compound in each study. The studied mice were thereafter compared to control mice and the difference in the area of neovascularization was recorded as an averaged value. Each group of mice so studied constitutes an "n" value of one, so that "n" values greater than one represent multiple studies whose averaged result is provided in the table. A contemplated compound typically exhibits about 25 to about 75 percent inhibition, whereas the vehicle control exhibits zero percent inhibition.

Example 390

In Vivo PC-3 Tumor Reduction

PC-3 human pancreatic cancer cells (ATCC CRL 1435) were grown to 90% confluence in F12/MEM (Gibco) containing 7% FBS (Gibco). Cells were mechanically harvested using a rubber scraper, and then washed twice with cold medium. The resulting cells were resuspended in cold medium with 30% matrigel (Collaborative Research) and the cell-containing medium was maintained on ice until used.

Balb/c nu/nu mice at 7–9 weeks of age were anesthetized with avertin [2,2,2-tribromethanol/t-amyl alcohol (1 g/1 mL) diluted 1:60 into phosphate-buffered sline] and $3-5 \times 10^6$ of the above cells in 0.2 mL of medium were injected into the left flank of each mouse. Cells were injected in the morning, whereas dosing with an inhibitor began at 6 PM. The animals were gavaged BID from day zero (cell injection day) to day 25–30, at which time the animals were euthanized and tumors weighed.

Compounds were dosed at 10 mg/mL in 0.5% methylcellulose/0.1% polysorbate 80 to provide a 50 mg/kg (mpk) dose twice each day, or diluted to provide a 10 mg/kg (mpk) dose twice each day. Tumor measurements began on day 7 and continued every third or fourth day until completion of the study. Groups of ten mice were used in each study and nine to ten survived. Each group of mice so studied constitutes an "n" value of one, so that "n" values greater than one represent multiple studies whose averaged result is provided in the table.

Example 391

Tumor Necrosis Factor Assays

Cell Culture

The cells used in the assay are the human moncytic line U-937 (ATCC CRL-1593). The cells are grown in RPMI w/10% FCS and PSG supplement (R-10) and are not permitted to overgrow. The assay is carried out as follows:

1. Count, then harvest cells by centrifugation. Resuspend the pellet in R-10 supplement to a concentration of $1.540 \times 10^6$ cells/mL.

2. Add test compound in 65 uL R-10 to the appropriate wells of a 96-well flat bottom tissue culture plate. The initial dilution from a DMSO stock (100 mM compound) provides a 400 uM solution, from which five additional three-fold serial dilutions are made. Each dilution of 65 ul (in triplicate) yields final compound test concentrations of 100 $\mu$M, 33.3 $\mu$M, 11.1 $\mu$M, 3.7 $\mu$M, 1.2 $\mu$M and 0.4 $\mu$M.

3. The counted, washed and resuspended cells (200,000 cells/well) in 130 $\mu$L are added to the wells.

4. Incubation is for 45 min to 1 hr at 37° C. in 5% CO2 in a water saturated container.

5. R-10 (65 uL)containing 160 ng/mL PMA (Sigma) is added to each well.

6. The test system is incubated at 37° C. in 5% CO2 overnight (18–20 hr) under 100% humidity.

7. Supernatant, 150 $\mu$L, is carefully removed from each well for use in the ELISA assay.

8. For toxicity, a 50 $\mu$L aliquot of working solution containing 5 mL R-10, 5 mL MTS solution [CellTiter 96 AQueous One Solution Cell Proliferation Assay Cat.#G358/ 0,1 (Promega Biotech)] and 250 ul PMS solution are added to each well containing the remaining supernatant and cells and the cells incubated at 37° C. in 5% $CO_2$ until the color develops. The system is excited at 570 nm and read at 630 nm.

TNF Receptor II ELISA Assay

1. Plate 100 $\mu$L/well 2 ug/mL mouse anti-human TNFrII antibody (R&D Systems #MAB226) in 1×PBS (pH 7.1, Gibco) on NUNC-Immuno Maxisorb plate. Incubate the plate at 4° C. overnight (about 18–20 hr).

2. Wash the plate with PBS-Tween (1×PBS w/0.05% Tween).

3. Add 200 $\mu$L 5% BSA in PBS and block at 37° C. in a water saturated atmosphere for 2 hr.

4. Wash the plate with PBS-Tween.

5. Add sample and controls (100 $\mu$l of each) to each well. The standards are 0, 50, 100, 200, 300 and 500 pg recombinant human TNFrII (R&D Systems #226-B2) in 100 $\mu$L 0.5% BSA in PBS. The assay is linear to between 400–500 pg of standard.

6. Incubate at 37° C. in a saturated atmosphere for 1.5 hr.

7. Wash the plate with PBS-Tween.

8. Add 100 $\mu$L goat anti-human TNFrII polyclonal (1.5 1 $\mu$g/mL R&D Systems #AB226-PB in 0.5% BSA in PBS). Incubate at 37° C. in a saturated atmosphere for 1 hr.

10. Wash the plate with PBS-Tween.

11. Add 100 $\mu$L anti-goat IgG-peroxidase (1:50,000 in 0.5% BSA in PBS, Sigma #A5420).

11. Incubate at 37° C. in a saturated atmosphere for 1 hr.

12. Wash the plate with PBS-Tween.

13. Add 10 μL KPL TMB developer, develop at room temperature (usually about 10 min), then terminate with phosphoric acid and excite at 450 nm and read at 570 nm.

TNFα ELISA Assay

Coat Immulon® plates with 0.1 mL/well of 1 ug/mL Genzyme mAb in 0.1 M NaHCO3 pH 8.0 buffer overnight (about 18–20 hr) at 4° C., wrapped tightly in Saran® wrap.

Flick out coating solution and block plates with 0.3 mL/well blocking buffer overnight at 4° C., wrapped in Saran® wrap.

Wash wells thoroughly 4x with wash buffer and completely remove all wash buffer. Add 0.1 mL/well of either samples or rhTNFα standards. Dilute samples if necessary in appropriate diluant (e.g. tissue culture medium). Dilute standard in same diluant. Standards and samples should be in triplicates.

Incubate at 37° C. for 1 hr in humidified container.

Wash plates as above. Add 0.1 mL/well of 1:200 dilution of Genzyme rabbit anti-hTNFa.

Repeat incubation.

Repeat wash. Add 0.1 mL/well of 1 μg/mL Jackson goat anti-rabbit IgG (H+L)-peroxidase.

Incubate at 37° C. for 30 min.

Repeat wash. Add 0.1 mL/well of peroxide-ABTS solution.

Incubate at room temperature for 5–20 min.

Read OD at 405 nm.

12 Reagents are:

Genzyme mouse anti-human TNF? monoclonal (Cat. #80-3399-01)

Genzyme rabbit anti-human TNF? polyclonal (Cat. #IP-300)

Genzyme recombinant human TNF? (Cat. #TNF-H).

Jackson Immunoresearch peroxide-conjugated goat anti-rabbit IgG (H+L) (Cat. #111-035-144).

Kirkegaard/Perry peroxide ABTS solution (Cat #50-66-01).

Immulon 2 96-well microtiter plates.

Blocking solution is 1 mg/mL gelatin in PBS with 1×thimerasol.

Wash buffer is 0.5 mL Tween®20 in 1 liter of PBS.

Example 392

In Vitro Aggrecanase Inhibition Assay

Assays for measuring the potency ($IC_{50}$) of a compound toward inhibiting aggrecanase are known in the art.

One such assay, for example, has been reported in European Patent Application Publ. No. EP 1 081 137 A1. In that assay, primary porcine chondrocytes from articular joint cartilage are isolated by sequential trypsin and collagenase digestion followed by collagenase digestion overnight and are plated at $2 \times 10^5$ cells per well into 48 well plates with 5 μCi/ml$^{35}$S (1000 Ci/mmol) sulphur in type 1 collagen coated plates. Cells are allowed to incorporate label into their proteoglycan matrix (approximately 1 week) at 37° C. under an atmosphere of 5% $CO_2$. The night before initiating the assay, chondrocyte monolayers are washed 2 times in DMEM/1% PSF/G and then allowed to incubate in fresh DMEM/1% FBS overnight. The next morning, chondrocytes are washed once in DMEM/1% PSF/G. The final wash is allowed to sit on the plates in the incubator while making dilutions. Media and dilutions are made as described in the following Table C:

TABLE C

| | |
|---|---|
| control media | DMEM alone |
| IL-1 media | DMEM + IL-1 (5 ng/ml) |
| drug dilutions | Make all compound stocks at 10 mM in DMSO. Make a 100 μM stock of each compound in DMEM in 96-well plate. Store in freezer overnight. The next day, perform serial dilutions in DMEM with IL-1 to 5 μM, 500 nM, and 50 nM. Aspirate final wash from wells and add 50 μM of compound from above dilutions to 450 μL of IL-1 media in appropriate wells of the 48 well plates. Final compound concentrations equal 500 nM, 50 nM, and 5 nM. All samples completed in triplicate with control and IL-1 alone on each plate. |

Plates are labeled and only the interior 24 wells of the plate are used. On one of the plates, several columns are designated as IL-1 (no drug) and control (no IL-1, no drug). These control columns are periodically counted to monitor 35S-proteoglycan release. Control and IL-1 media are added to wells (450 μL) followed by compound (50 μL) so as to initiate the assay. Plates are incubated at 37° C. with 5% $CO_2$ atmosphere. At 40–50% release (when CPM from IL-1 media is 4–5 times control media) as assessed by liquid scintillation counting (LSC) of media samples, the assay is terminated (about 9 to about 12 hours). Media is removed from all wells and placed into scintillation tubes. Scintillate is added and radioactive counts are acquired (LSC). To solubilize cell layers, 500 μL of papain digestion buffer (0.2 M Tris, pH 7.0, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC). The percent of released counts from the total present in each well is determined. Averages of the triplicates are made with control background subtracted from each well. The percent of compound inhibition is based on IL-1 samples as 0% inhibition (100% of total counts).

Another assay for measuring aggrecanase inhibition has been reported in WIPO Int'l Publ. No. WO 00/59874. That assay reportedly uses active aggrecanase accumulated in media from stimulated bovine cartilage (BNC) or related cartilage sources and purified cartilage aggrecan monomer or a fragment thereof as a substrate. Aggrecanase is generated by stimulation of cartilage slices with interleukin-1 (IL-1), tumor necrosis factor alpha (TNF-α), or other stimuli. To accumulate BNC aggrecanase in culture media, cartilage reportedly is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. To decrease the amounts of matrix metalloproteinases released into the media during aggrecanase accumulation, agents which inhibit MMP-1, -2, -3, and -9 biosynthesis are included during stimulation. This BNC conditioned media containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, et al., *Biochem J*, 306:799–804 (1995)). This antibody reportedly recognizes aggrecan fragments with the N-terminus, 374ARGSVIL, generated upon cleavage by aggrecanase. The BC-3 antibody reportedly recognizes this neoepitope only when it is at the N-terminus and not when it is present internally within aggrecan fragments or within the aggrecan protein core. Only products produced upon cleavage by aggrecanase reportedly are detected. Kinetic studies using this assay reportedly yield a Km of 1.5+/−0.35 $\mu$M for aggrecanase. To evaluate inhibition of aggrecanase, compounds are prepared as 10 mM stocks in DMSO, water, or other solvents and diluted to appropriate concentrations in water. Drug (50 $\mu$L) is added to 50 $\mu$L of aggrecanase-containing media and 50 $\mu$L of 2 mg/ml aggrecan substrate and brought to a final volume of 200 $\mu$L in 0.2 M Tris, pH 7.6, containing 0.4 M NaCl and 40 mM $CaCl_2$. The assay is run for 4 hr at 37° C., quenched with 20 mM EDTA, and analyzed for aggrecanase-generated products. A sample containing enzyme and substrate without drug is included as a positive control and enzyme incubated in the absence of substrate serves as a measure of background. Removal of the glycosaminoglycan side chains from aggrecan reportedly is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 $\mu$g GAG) for 2 hr at 37° C. and then with keratanase (0.1 units/10 $\mu$g GAG) and keratanase II (0.002 units/10 $\mu$g GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 $\mu$L of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A compound or a salt thereof, wherein:
the compound corresponds in structure to the Formula X:

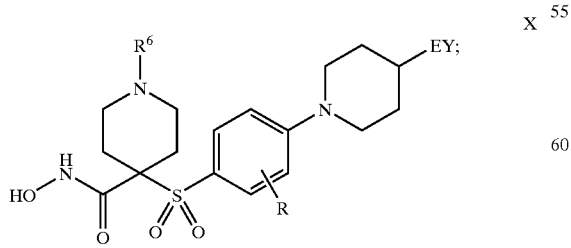

X $R^6$ is selected from the group consisting of hydrogen, formyl, sulfonic-$C_1$–$C_6$-alkyl, $C_1$–$C_6$-alkoxycarbonyl-$C_1$–$C_6$-alkyl, carboxy-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, carboxy-$C_1$–$C_6$-alkylcarbonyl, $C_1$–$C_6$-alkylcarbony-$C_1$–$C_6$-alkylcarbonyl, $C_1$–$C_6$-alkoxycarbonyl, carboxy, $C_1$–$C_6$-alkylcarbonyl, $R^8R^9$-aminocarbonyl, aryl-$C_1$–$C_6$-alkyl, arylcarbonyl, bis($C_1$–$C_6$-alkoxy-$C_1$–$C_6$-alkyl)-$C_1$–$C_6$-alkyl, $C_1$–$C_6$-alkyl, halo-$C_1$–$C_6$-alkyl, trifluoromethyl-$C_1$–$C_6$ alkyl, perfluoro-$C_1$–$C_6$-alkoxy-$C_1$–$C_6$-alkyl, $C_1$–$C_6$-alkoxy-$C_1$–$C_6$-alkyl, $C_3$–$C_6$-cycloalkyl, heteroarylcarbonyl, heterocyclylcarbonyl, aryl, heterocyclyl, heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, aminocarbonyl, $C_1$–$C_6$-alkylimino($R^{10}$)carbonyl, arylimino($R^{10}$)carbonyl, $C_5$–$C_6$-heterocyclylimino($R^{10}$)carbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkylcarbonyl, hydroxy-$C_1$–$C_6$-alkylcarbonyl, thiol-$C_1$–$C_6$-alkylcarbonyl, $C_3$–$C_6$-alkenyl, $C_3$–$C_6$-alkynyl, aryloxycarbonyl, $R^8R^9$-aminoimino($R^{10}$)methyl, $R^8R^9$-amino-$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfonyl-$C_1$–$C_6$-alkyl, $R^8R^9$-amino-$C_1$–$C_6$-alkylsulfonyl, and $R^8R^9$-amino-$C_1$–$C_6$-alkyl;

as to $R^8$ and $R^9$:
$R^8$ and $R^9$ are independently selected from the group consisting of hydrogen, hydroxy, $C_1$–$C_6$-alkyl, $C_1$–$C_6$-alkylcarbonyl, arylcarbonyl, aryl, aryl-$C_1$–$C_6$-alkyl, heteroaryl, heteroaryl-$C_1$–$C_6$-alkyl, $C_2$–$C_6$-alkynyl $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocyclyl-$C_1$–$C_6$-alkyl, $C_1$–$C_6$-alkoxy-$C_1$–$C_6$-alkyl, aryl-$C_1$–$C_6$-alkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, carboxy-$C_1$–$C_6$-alkyl, carboxyaryl-$C_1$–$C_6$-alkyl, aminocaxbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$ alkyl a sulfoxide of any said thio substituents, a sulfone of any said thio substituents, trifluoromethyl-$C_1$–$C_6$-alkyl, halo-$C_1$–$C_6$-alkyl, alkoxycarbonylamino-$C_1$–$C_6$-alkyl and amino-$C_1$–$C_6$-alkyl, wherein:
the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl, or $R^8$ and $R^9$, together with the atom to which they are bonded, form a 5- to 8-membered heterocyclic or heteroaryl ring containing up to 2 heteroatoms independently selected from the group consisting of nitrogen, oxygen, and sulfur; only one of $R^8$ and $R^9$ is hydroxy;

$R^{10}$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocyclyl-$C_1$–$C_6$-alkyl, $C_1$–$C_6$-alkoxy-$C_1$–$C_6$- alkyl, aryl-$C_1$–$C_6$-alkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, carboxy-$C_1$–$C_6$-alkyl, carboxyaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfaxide of any said thio substituents, a sulfone of any said thio substituents, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:
  the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl;
E is selected from the group consisting of a bond, —C(O)—, and —S—;
Y is selected from the group consisting of hydrogen, alkyl, alkoxy, haloalkyl, aryl, arylalkyl, cycloalkyl, heteroaryl, hydroxy, aryloxy, arylalkoxy, heteroaryloxy, heteroarylalkyl, perfluoroalkoxy, perfluoroalkylthio, trifluoromethylalkyl, alkenyl, heterocyclyl, cycloalkyl, trifluormethyl, alkoxycarbonyl, and aminoalkyl, wherein:
  the aryl, heteroaryl, arylalkyl, or heterocyclyl optionally is substituted with up to 2 substituents independently selected from the group consisting of alkylcarbonyl, halo, nitro, arylalkyl, aryl, alkoxy, trifluoroalkyl, trifluoroalkoxy, and amino, wherein:
    the amino nitrogen optionally is substituted with up to 2 substituents independently selected from the group consisting of alkyl and arylalkyl; and
R is selected from the group consisting of hydrogen, cyano, perfluoroalkyl, trifluoromethoxy, trifluoromethyithlo, haloalkyl, trifluoromethylalkyl, arylalkoxycarbonyl, aryloxycarbonyl, hydroxy, halo, alkyl, alkoxy, nitro, thiol, hydroxycarbonyl, aryloxy, arylthio, arylalkyl, aryl, arylcarbonylamino, heteroaryloxy, heteroarylthio, heteroarylalkyl, cycloalkyl, heterocyclyloxy, heterocyclylthio, heterocyclylamino, cycloalkyloxy, cycloalkylthio, heteroarylalkoxy, heteroarylalkylthio, arylalkoxy, arylalkylthio, arylalkylamino, heterocyclyl, heteroaryl, arylazo, hydroxycarbonylalkoxy, alkoxycarbonylalkoxy, alkylcarbonyl, arylcarbonyl, arylalkylcarbonyl, alkylcarbonyloxy, arylalkylcarbonyloxy, hydroxysilcyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, aminocarbonyl, and aminoalkyl, wherein:
  the amino nitrogen optionally is substituted with:
    up two substituents that are independently selected from the group consisting of alkyl, aryl, heteroaryl, arylalkyl, cycloalkyl, arylalkoxycarbonyl, alkoxycarbonyl, arylcarbonyl, arylalkylcarbonyl, heteroarylcarbonyl, heteroarylalkylcarbonyl, and alkylcarbonyl, or
    two substituents such that the two substituents, together with the amino nitrogen, form a 5- to 8-member heterocyclyl or heteroaryl ring that:
      contains from zero to two additional heteroatoms that are independently selected from the group consisting of nitrogen, oxygen, and sulfur,
      optionally is substituted with up to two substituents independently selected from the group consisting of aryl, alkyl, heteroaryl, arylalkyl, heteroarylalkyl, hydroxy, alkoxy, alkylcarbonyl, cycloalkyl, heterocyclylalkyl, alkoxycarbonyl, hydroxyalkyl, trifluoromethyl, benzofused heterocyclylalkyl, hydroxyalkoxyalkyl, arylalkoxycarbonyl, hydroxycarbonyl, aryloxycarbonyl, benzofused heterocyclylalkoxy, benzofused cycloalkylcarbonyl, heterocyclylalkylcarbonyl, and cycloalkylcarbonyl,
  the aminocarbonyl nitrogen is:
    unsubstituted,
    the reacted amine of an amino acid,
    substituted with one or two substituents independently selected from the group consisting of alkyl, hydroxyalkyl, hydroxyheteroarylalkyl, cycloalkyl, arylalkyl, trifluoromethylalkyl, heterocyclylalkyl, benzofused heterocyclylalkyl, benzofused cycloalkyl, and N,N-dialkylsubstituted alkylamino-alkyl, or
    substituted with two substituents such that the two substituents, together with the aninocarbonyl nitrogen, form a 5- to 8-member heterocyolyl or heteroaryl ring that optionally is substituted with up to two substituents independently selected from the group consisting of alkyl, alkoxycarbonyl, nitro, heterocyclylalkyl, hydroxy, hydroxycarbonyl, aryl, arylalkyl, heteroaralkyl, and amino, wherein the amino nitrogen optionally is substituted with:
      two substituents independently selected from the group consisting of alkyl, aryl, and heteroaryl; or
      two substituents such that the two substituents, together with the amino nitrogen, form a 5- to 8-member heterocyclyl or heteroaryl ring, and
  the aminoalkyl nitrogen optionally is substituted with:
    up to two substituents independently selected from the group consisting of alkyl, aryl, arylalkyl, cycloalkyl, arylalkoxycarbonyl, alkoxycarbonyl, and alkylcarbonyl, or
    two substituents such that the two substituents, together with the aminoalkyl nitrogen, form a 5- to 8-member heterocyclyl or heteroaryl ring.
2. A compound or salt according to claim 1, wherein R is halo.
3. A compound or salt according to claim 1, wherein the compound corresponds in structure to Formula XA:

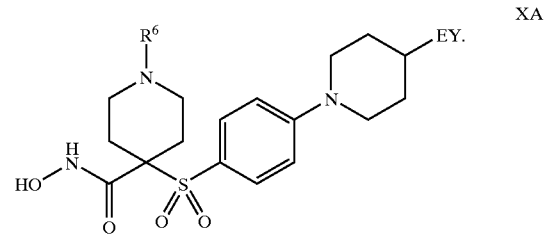

4. A compound or salt according to claim 3, wherein the salt is a pharmaceutically acceptable salt.
5. A compound or salt according to claim 3, wherein Y is selected from the group consisting of aryl, arylalkyl, cycloalkyl, heteroaryl, aryloxy, arylalkoxy, heteroaryloxy, heteroarylalkyl, heterocyclyl, and cycloalkyl, wherein:

the aryl, heteroaryl, arylalkyl, or heterocyclyl optionally is substituted with up to 2 substituents independently selected from the group consisting of alkylcarbonyl, halo, nitro, arylalkyl, aryl, alkoxy, trifluoroalkyl, trifluoroalkoxy, and amino, wherein:
the amino nitrogen optionally is substituted with up to 2 substituents independently selected from the group consisting of alkyl and arylalkyl.

6. A compound or salt according to claim 3, wherein E is a bond.

7. A compound or salt according to claim 3, wherein E is —C(O)—.

8. A compound or salt according to claim 3, wherein E is —S—.

9. A compound or salt according to claim 3, wherein $R^6$ is selected from the group consisting of $C_1$–$C_6$-alkyl, $C_1$–$C_6$-alkoxy-$C_1C_6$-alkyl, $C_3$–$C_6$-cycloalkyl, $C_3$–$C_8$-cycloalkyl-$C_1$–$C_6$-alkyl, $C_1$–$C_6$-alkylsulfonyl, $C_3$–$C_6$-alkenyl, and $C_3$–$C_6$-alkynyl.

10. A compound or salt according to claim 3, wherein $R^6$ is perfluoro-$C_1$–$C_6$-alkyl.

11. A compound or salt according to claim 3, wherein $R^8$, $R^9$, or $R^{10}$ is perfluoro-$C_1$–$C_6$-alkyl.

12. A compound or a salt thereof, wherein:
the compound corresponds in structure to Formula X:

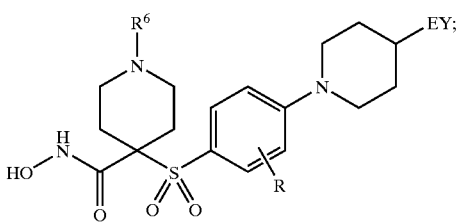

X

E is selected from the group consisting of a bond, —C(O)—, and —S—;
$R^6$ is selected from the group consisting of hydrogen, arylalkoxycarbonyl, alkylcarbonyl, alkyl, alkoxyalkyl, cycloalkyl, heteroarylcarbonyl, heteroaryl, cycloalkylalkyl, alkylsulfonyl, haloalkylcarbonyl, alkenyl, allkynyl, and $R^8R^9$-aminoalkylcarbonyl;
as to $R^8$ and $R^9$:
$R^8$ and $R^9$ are independently selected from the group consisting of hydrogen, alkyl, alkoxy, hydroxyalkyl, alkoxyalkyl, hydroxyalkoxyalkyl, heteroaylalkyl, cycloalkylalkyl, heterocyclylcarbonyl, haloalkyl, and aminoalkyl, wherein:
the aminoalkyl nitrogen optionally is substituted with up to two substituents independently selected from the group consisting of alkyl, or
$R^8$ and $R^9$, together with the atom to which they are bonded, form a 5- to 8-membered heterocyclyl or heteroaryl containing up to 3 hetero atoms independently selected from the group consisting of nitrogen, oxygen, and sulfur, wherein:
any such heterocyclyl optionally is substituted with one or more substituents independently selected from the group consisting of hydroxy, keto, carboxy, alkoxyalkyl, hydroxyalkyl, hydroxyalkoxyalky, alkoxycarbonylalkyl, heterocyclylalkyl, alkoxycarbonyl, and aminoalkyl, wherein:
the aminoalkyl nitrogen optionally is substituted with up to two substituents independently selected from the group consisting of alkyl; and Y is selected from the group consisting of cycloalkyl, 2,3-dihydroindolyl, heterocyclyl, aryl, heteroaryl, arylalkyl, and heteroarylalkyl, wherein:
any such substituent optionally is substituted with one or more optionally substituted substituents independently selected from the group consisting of halogen, hydroxy, keto, alkyl, haloalkyl, hydroxyalkyl, alkenyl, alkoxy, alkylcarbonyl, haloalkoxy, alkylthio, alkoxyalkyl, alkoxycarbonylalkyl, cycloalkyl, cycloalkylalkyl, cycloalkyloxy, cycloalkylalkoxy, cycloalkylalkoxyalkyl, aryl, arylalkyl, arylalkoxy, heterocyclyl, heterocyclylalkyl, heteroaryl, heteroarylcarbonyl, heterocyclylcarbonylalkyl, alkylsulfonyl, amino, aminoalkyl, and aminocarbonyl, wherein:
any such substituent optionally is substituted with one or more substituents independently selected from the group consisting of halogen, nitro, alkyl, haloalkyl, alkoxy, haloalkoxy, and alkylcarbonyl, and
the nitrogen of the amino, aminoalkyl, or aminocarbonyl optionally is substituted with up to two substituents independently selected from the group consisting of alkyl and cycloalkylalkyl; and R is selected from the group consisting of hydrogen and halogen.

13. A compound or salt according to claim 12, wherein the compound corresponds in struture to Formula XA:

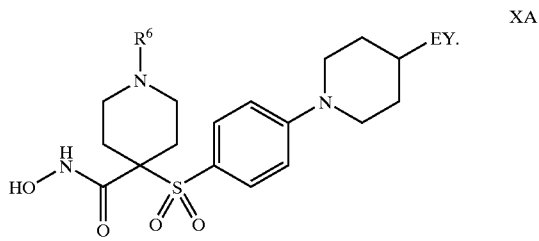

XA

14. A compound or salt according to claim 13, wherein the salt is a pharmaceutically acceptable salt.

15. A compound or salt according to claim 13, wherein $R^6$ is $C_1$–$C_6$-alkyl.

16. A compound or salt according to claim 13, wherein $R^6$ is $C_1$–$C_6$-alkoxy-$C_1$–$C_6$-alkyl.

17. A compound or salt according to claim 13, wherein $R^6$ is $C_3$–$C_6$-cycloalkyl.

18. A compound or salt according to claim 13, wherein $R^6$ is $C_3$–$C_8$-cycloalkyl-$C_1$–$C_6$-alkyl.

19. A compound or salt according to claim 13, wherein $R^6$ is $C_3$–$C_6$-alkenyl.

20. A compound or salt according to claim 13, wherein $R^6$ is $C_3$–$C_6$-alkynyl.

21. A compound or salt according to claim 13, wherein $R^6$ is $C_1$–$C_6$-alkylsulfonyl.

22. A compound or salt according to claim 13, wherein E is —C(O)—.

23. A compound or salt according to claim 22, wherein:
$R^6$ is selected from the group consisting of hydrogen, aryl-$C_1$–$C_6$-alkoxycarbonyl, $C_1$–$C_6$-alkoxycarbonyl, $C_1$–$C_6$-alkyl, $C_1$–$C_6$-alkoxy-$C_1$–$C_6$-alkyl, $C_3$–$C_6$-cycloalkyl, heteroaryl, heteroarylcarbonyl, halo-$C_1$–$C_6$-alkylcarbonyl and $R^8R^9$-amino-$C_1$–$C_6$-alkylcarbonyl;
as to $R^8$ and $R^9$:
$R^8$ and $R^9$ are independently selected from the group consisting of hydrogen, $C_1$–$C_6$-alkyl, $C_1$–$C_6$-alkoxy, hydroxy-$C_1$–$C_6$-alkyl, $C_1$–$C_6$-alkoxy-$C_1$–$C_6$-alkyl, heteroaryl-$C_1$–$C_6$-alkyl, $C_3$–$C_6$-cycloalkyl-$C_1$–$C_6$-alkyl, heterocyclylcarbonyl, halo-$C_1$-$C_6$-alkyl, hydroxy-$C_1$–$C_6$-alkoxy-$C_1$–$C_6$-alkyl, and amino-$C_1$–$C_6$-alkyl, wherein:

the amino-$C_1$–$C_6$-alkyl nitrogen optionally is substituted with up to two substituents independently selected from the group consisting of $C_1$–$C_6$-alkyl, or $R^8$ and $R^9$, together with the atom to which they are bonded, form a heterocyclyl or heteroaryl containing up to 3 heteroatoms independently selected from the group consisting of nitrogen, oxygen, and sulfur, wherein:

any such heterocyclyl optionally is substituted with one or more substituents independently selected from the group consisting of hydroxy, keto, carboxy, hydroxy-$C_1$–$C_6$-alkyl, hydroxy-$C_1$–$C_6$-alkoxy-$C_1$–$C_6$-alkyl, $C_1$–$C_6$-alkoxycarbonyl-$C_1$-$C_6$-alkyl, heterocyclyl-$C_1$–$C_6$-alkyl, -$C_1$–$C_6$-alkoxycaxbonyl, $C_1$–$C_6$-alkoxy-$C_1$–$C_6$-alkyl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl; and Y is selected from the group consisting of heterocyclyl, aryl, heteroaryl, and arylmethyl, wherein:

any such substituent optionally is substituted with one or more substituents independently selected from the group consisting of halogen, hydroxy, $C_1$–$C_6$alkyl, halo-$C_1$–$C_6$-alkyl, hydroxy-$C_1$–$C_6$-alkyl, $C_2$–$C_6$-alkenyl, $C_1$–$C_6$-alkoxy, $C_1$–$C_6$-alkylcarbonyl, halo-$C_1$–$C_6$-alkoxy, $C_1$–$C_6$-alkylthio, $C_1$–$C_6$-alkoxy-$C_1$–$C_6$-alkyl, $C_1$–$C_6$-alkoxycarbonyl-$C_1$–$C_6$-alkyl, $C_3$–$C_6$-cycloalkyl, aryl, aryl-$C_1$–$C_6$-alkyl, aryl-$C_1$–$C_6$-alkoxy, heterocyclyl, heterocyclyl-$C_1$–$C_6$-alkyl, heteroaryl, heteroarylcarbonyl, heterocyclylcarbonyl-$C_1$–$C_6$-alkyl, amino, and amino-$C_1$–$C_6$-alkyl, wherein:

any such substituent optionally is substituted with one or more substituents independently selected from the group consisting of halogen, nitro, $C_1$–$C_6$-alkyl, halo-$C_1$–$C_6$-alkyl, $C_1$–$C_6$-alkoxy, and $C_1$–$C_6$-alkylcarbonyl, and the nitrogen of the amino or amino-$C_1$–$C_6$-alkyl optionally is substituted with up to two substituents independently selected from the group consisting of $C_1$–$C_6$-alkyl and $C_3$–$C_6$-cycloalkyl-$C_1$–$C_6$-alkyl.

24. A compound or salt according to claim 23, wherein Y is phenyl optionally substituted with one or more substituents independently selected from the group consisting of halogen, hydroxy, $C_1$–$C_6$-alkyl, halo-$C_1$–$C_6$-alkyl, hydroxy-$C_1$–$C_6$-alkyl, $C_2$–$C_6$-alkenyl, $C_1$–$C_6$-alkoxy, $C_1$–$C_6$-alkylcarbonyl, halo-$C_1$–$C_6$-alkoxy, $C_1$–$C_6$-alkylthio, $C_1$–$C_6$-alkoxy-$C_1$–$C_6$-alkyl, $C_1$–$C_6$-alkoxycarbonyl-$C_1$–$C_6$-alkyl, $C_3$–$C_6$-cycloalkyl, aryl, aryl-$C_1$–$C_6$-alkyl, aryl-$C_1$–$C_6$-alkoxy, heterocyclyl, heterocyclyl-$C_1$–$C_6$-alkyl, heteroaryl, heteroarylcarbonyl, heterocyclylcarbonyl-$C_1$–$C_6$-alkyl, amino, and amino-$C_1$–$C_6$-alkyl, wherein:

any such substituent optionally is substituted with one or more substituents independently selected from the group consisting of halogen, nitro, $C_1$–$C_6$-alkyl, halo-$C_1$–$C_6$-alkyl, $C_1$–$C_6$-alkoxy, and $C_1$–$C_6$-alkylcarbonyl, and the nitrogen of the amino or amino-$C_1$–$C_6$-alkyl optionally is substituted with up to two substituents independently selected from the group consisting of $C_1$–$C_6$-alkyl and $C_3$–$C_6$-cycloalkyl-$C_1$–$C_6$-alkyl.

25. A compound or salt according to claim 23, wherein Y is thienyl optionally substituted with one or more substituents independently selected from the group consisting of halogen, hydroxy, $C_1$–$C_6$-alkyl, halo-$C_1$–$C_6$-alkyl, hydroxy-$C_1$–$C_6$-alkyl, $C_2$-$C_6$-alkenyl, $C_1$–$C_6$-alkoxy, $C_1$–$C_6$-alkylcarbonyl, halo-$C_1$–$C_6$-alkoxy, $C_1$–$C_6$-alkylthio, $C_1$–$C_6$-alkoxy-$C_1$–$C_6$-alkyl, $C_1$–$C_6$-alkoxycarbonyl-$C_1$–$C_6$-alkyl, $C_3$–$C_6$-cycloalkyl, aryl, aryl-$C_1$–$C_6$-alkyl, aryl-$C_1$–$C_6$-alkoxy, heterocyclyl, heterocyclyl-$C_1$–$C_6$-alkyl, heteroaryl, heteroarylcarbonyl, heterocyclylcarbonyl-$C_1$–$C_6$-alkyl, amino, and amino-$C_1$–$C_6$-alkyl, wherein:

any such substituent optionally is substituted with one or more substituents independently selected from the group consisting of halogen, nitro, $C_{1-6}$-alkyl, halo-$C_1$–$C_6$-alkyl, $C_1$–$C_6$-alkoxy, and $C_1$–$C_6$-alkylcarbonyl, and the nitrogen of the amino or amino-$C_1$–$C_6$-alkyl optionally is substituted with up to two substituents independently selected from the group consisting of $C_{1-6}$-alkyl and $C_3$–$C_6$-cycloalkyl-$C_1$–$C_6$-alkyl.

26. A compound or salt according to claim 22, wherein:

$R^6$ is selected from the group consisting of $C_1$–$C_6$-alkyl, $C_1$–$C_6$-alkoxy-$C_1$–$C_6$-alkyl, $C_3$–$C_6$-cycloalkyl, $C_3$–$C_8$-cycloalkyl-$C_1$–$C_6$-alkyl, $C_3$–$C_6$-alkenyl, $C_3$–$C_6$-alkynyl, and $C_1$–$C_6$-alkylsulfonyl; and Y is selected from the group consisting of aryl, heteroaryl, arylmethyl, and heteroarylmethyl, wherein:

any such substituent optionally is substituted with one or more substituents independently selected from the group consisting of halogen, $C_1$–$C_6$-alkyl, hydroxy-$C_1$–$C_6$-alkyl, $C_2$–$C_6$-alkenyl, $C_1$–$C_6$-alkoxy, $C_{1-6}$-alkoxy-$C_1$–$C_6$-alkyl, $C_3$–$C_6$-cycloalkyl-$C_1$–$C_6$-alkyl, $C_3$–$C_6$-cycloalkyloxy, $C_3$–$C_6$-cycloalkyl-$C_1$–$C_6$-alkoxy, $C_3$–$C_6$-cycloalkyl-$C_1$–$C_6$-alkoxy-$C_1$–$C_6$-alkyl, heterocyclyl-$C_1$–$C_6$-alkyl, amino, and amino-$C_1$–$C_6$-alkyl, wherein:

the nitrogen of the amino or amino-$C_1$–$C_6$-alkyl optionally is substituted with up to two substituents independently selected from the group consisting of $C_1$–$C_6$-alkyl.

27. A compound or salt according to claim 26, wherein Y is phenyl or phenylrnethyl, wherein:

the phenyl or phenylmethyl optionally is substituted with one or more substituents independently selected from the group consisting of halogen, $C_1$–$C_6$-alkyl, hydroxy-$C_1$–$C_6$-alkyl, $C_2$–$C_6$-alkenyl, $C_{1-6}$-alkoxy, $C_1$–$C_6$-alkoxy-$C_{1-6}$-alkyl, $C_3$–$C_6$-cycloalkyl-$C_1$–$C_6$-alkyl, $C_3$–$C_6$-cycloalkyloxy, $C_3$–$C_6$-cycloalkyl-$C_1$–$C_6$-alkoxy, $C_3$–$C_6$-cycloalkyl-$C_1$–$C_6$-alkoxy-$C_1$–$C_6$-alkyl, heterocyclyl-$C_1$–$C_6$-alkyl, amino, and amino-$C_{1-6}$-alkyl, wherein:

the nitrogen of the amino or amino-$C_{1-6}$-alkyl optionally is substituted with up to two substituents independently selected from the group consisting of $C_{1-6}$-alkyl.

28. A compound or salt according to claim 27, wherein the compound corresponds in structure to the following formula:

29. A compound or salt according to claim 27, wherein the compound corresponds in structure to the following formula:

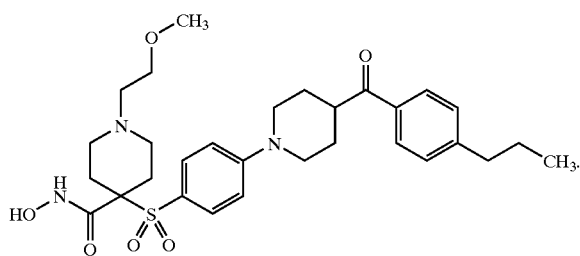

30. A compound or salt according to claim 27, wherein the compound corresponds in structure to the following formula:

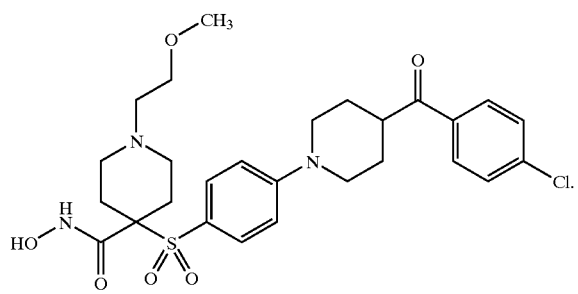

31. A compound or salt according to claim 27, wherein the compound corresponds in structure to the following formula:

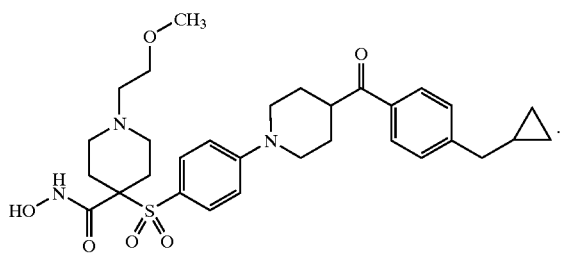

32. A compound or salt according to claim 26, wherein Y is thienyl or thienylmethyl, wherein:

the thienyl or thienylmethyl optionally is substituted with one or more substituents independently selected from the group consisting of halogen, $C_1$–$C_6$-alkyl, hydroxy-$C_1$–$C_6$-alkyl, $C_2$–$C_6$-alkenyl, $C_1$–$C_6$-alkoxy, $C_1$–$C_6$-alkoxy-$C_1$–$C_6$-alkyl, $C_3$–$C_6$-cycloalkyl-$C_1$–$C_6$-alkyl, $C_3$–$C_6$-cycloalkyloxy, $C_3$–$C_6$-cycloalkyl-$C_1$–$C_6$-alkoxy, $C_3$–$C_6$-cycloalkyl-$C_1$–$C_6$-alkoxy-$C_1$–$C_6$-alkyl, heterocyclyl-$C_1$–$C_6$-alkyl, amino, and amino-$C_1$–$C_6$-alkyl, wherein:

the nitrogen of the amino or amino-$C_1$–$C_6$-alkyl optionally is substituted with up to two substituents independently selected from the group consisting of $C_1$–$C_6$-alkyl.

33. A compound or salt according to claim 32, wherein the compound corresponds in structure to the following formula:

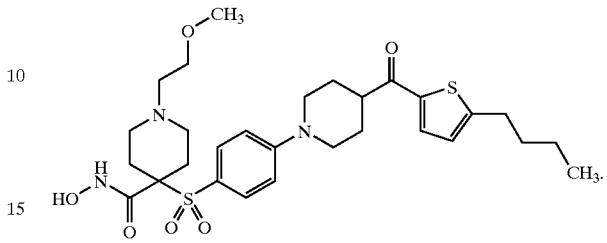

34. A compound or salt according to claim 32, wherein the compound corresponds in structure to the following formula:

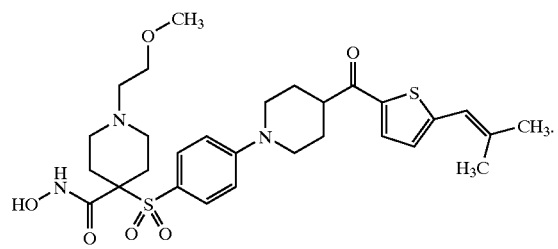

35. A compound or salt according to claim 13, wherein E is a bond.

36. A compound or salt according to claim 35, wherein:

$R^6$ is selected from the group consisting of hydrogen, aryl-$C_1$–$C_6$-alkoxycarbonyl, $C_1$–$C_6$-alkoxycarbonyl, $C_1$–$C_6$-alkyl, $C_1$–$C_6$-alkoxy-$C_1$–$C_6$-alkyl, $C_3$–$C_6$-cycloalkyl, heteroaryl, heteroarylcarbonyl, halo-$C_1$–$C_6$-alkylcarbonyl, and $R^8R^9$-amino-$C_1$–$C_6$-alkylcaxbonyl;

as to $R^8$ and $R^9$:

$R^8$ and $R^9$ are independently selected from the group consisting of hydrogen, $C_1$–$C_6$-alkyl, $C_1$–$C_6$-alkoxy, hydroxy-$C_1$–$C_6$-alkyl, $C_1$–$C_6$-alkoxy-$C_1$–$C_6$-alkyl, heteroaryl-$C_1$–$C_6$-alkyl, $C_3$–$C_6$-cycloalkyl-$C_1$–$C_6$-alkyl, heterocyclylcarbonyl, halo-$C_1$–$C_6$-alkyl, hydroxy-$C_1$–$C_6$-alkoxy-$C_1$–$C_6$-alkyl, and amino-$C_1$–$C_6$-alkyl, wherein:

the amino-$C_1$–$C_6$-alkyl nitrogen optionally is substituted with up to two substituents independently selected from the group consisting of $C_1$–$C_6$-alkyl, or $R^8$ and $R^9$, together with the atom to which they are bonded, form a heterocyclyl or heteroaryl containing up to 3 heteroatoms independently selected from the group consisting of nitrogen, oxygen, and sulfur, wherein:

any such heterocyclyl optionally is substituted with one or more substituents independently selected from the group consisting of hydroxy, keto, carboxy, hydroxy-$C_1$–$C_6$-alkyl, hydroxy-$C_1$–$C_6$-alkoxy-$C_1$–$C_6$-alkyl, $C_1$–$C_6$-alkoxycarbonyl-$C_1$–$C_6$-alkyl, heterocyclyl-$C_1$–$C_6$-alkyl, $C_1$–$C_6$-alkoxycarbonyl, $C_1$–$C_6$-alkoxy-$C_1$–$C_6$-alkyl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl;

Y is selected from the group consisting of aryl, 2,3-dihydroindolyl, heterocyclyl, and heteroaryl, wherein:
any such substituent optionally is substituted with one or more substituents independently selected from the group consisting of halogen, keto, hydroxy, $C_1$–$C_6$-alkyl, $C_1$–$C_6$-alkoxy, halo-$C_1$–$C_6$-alkyl, halo-$C_1$–$C_6$-alkoxy, aryl, aminocarbonyl, and $C_1$–$C_6$-alkylsulfonyl, wherein:
any such substituent optionally is substituted with one or more substituents independently selected from the group consisting of halogen, halo-$C_1$–$C_6$-alkyl, and halo-$C_1$–$C_6$-alkoxy, and
the nitrogen of the aminocarbonyl optionally is substituted with up to 2 substituents independently selected from the group consisting of $C_1$–$C_6$-alkyl.

37. A compound or salt according to claim 36, wherein Y is phenyl optionally substituted with one or more substituents independently selected from the group consisting of halogen, keto, hydroxy, $C_1$–$C_6$-alkyl, $C_1$–$C_6$-alkoxy, halo-$C_1$–$C_6$-alkyl, halo-$C_1$–$C_6$-alkoxy, aryl, aminocarbonyl, and $C_1$–$C_6$-alkylsulfonyl, wherein:
any such substituent optionally is substituted with one or more substituents independently selected from the group consisting of halogen, halo-$C_1$–$C_6$-alkyl, and halo-$C_1$–$C_6$-alkoxy, and
the nitrogen of the aminocarbonyl optionally is substituted with up to 2 substituents independently selected from the group consisting of $C_1$–$C_6$-alkyl.

38. A compound or salt according to claim 36, wherein:
$R^6$ is selected from the group consisting of $C_1$–$C_6$-alkyl, $C_1$–$C_6$-alkoxy-$C_1$–$C_6$-alkyl, $C_3$–$C_6$-cycloalkyl, $C_3$–$C_8$-cycloalkyl-$C_1$–$C_6$-alkyl, $C_3$–$C_6$-alkenyl, $C_3$–$C_6$-alkynyl, and $C_1$–$C_6$-alkylsulfonyl; and
Y is selected from the group consisting of heteroryl, aryl, and heterocyclyl, wherein:
any such substituent optionally is substituted with one or more substituents independently selected from the group consisting of halogen, $C_1$–$C_6$-alkyl, $C_1$–$C_6$-alkoxy, and aryl, wherein:
the aryl optionally is substituted with one or more substituents independently selected from the group consisting of halo-$C_1$–$C_6$-alkyl.

39. A compound or salt according to claim 36, wherein Y is phenyl optionally substituted with one or more substituents independently selected from the group consisting of halogen, $C_1$–$C_6$-alkyl, $C_1$–$C_6$-alkoxy, and aryl, wherein:
the aryl optionally is substituted with one or more substituents independently selected from the group consisting of halo-$C_1$–$C_6$-alkyl.

40. A compound or salt according to claim 13, wherein E is —S—.

41. A compound or salt according to claim 40, wherein:
$R^6$ is selected from the group consisting of hydrogen, aryl-$C_1$–$C_6$-alkoxycarbonyl, $C_1$–$C_6$-alkoxycarbonyl, $C_1$–$C_6$-alkyl, $C_1$–$C_6$-alkoxy-$C_1$–$C_6$-alkyl, $C_3$–$C_6$-cycloalkyl, heteroaryl, heteroarylcarbonyl, halo-$C_1$–$C_6$-alkylcarbonyl, and $R^8R^9$-amino-$C_1$–$C_6$-alkylcarbonyl;
as to $R^8$ and $R^9$:
$R^8$ and $R^9$ are independently selected from the group consisting of hydrogen, $C_1$–$C_6$-alkyl, $C_1$–$C_6$-alkoxy, hydroxy-$C_1$–$C_6$-alkyl, $C_1$–$C_6$-alkoxy-$C_1$–$C_6$-alkyl, heteroaryl-$C_1$–$C_6$-alkyl, $C_3$–$C_6$-cycloalkyl-$C_1$–$C_6$-alkyl, heterocyclylcarbonyl, halo-$C_1$–$C_6$-alkyl, hydroxy-$C_1$–$C_6$-alkoxy-$C_1$–$C_6$-alkyl, and amino-$C_1$–$C_6$-alkyl, wherein:
the amino-$C_1$–$C_6$-alkyl nitrogen optionally is substituted with up to two substituents independently selected from the group consisting of $C_1$–$C_6$-alkyl, or
$R^8$ and $R^9$, together with the atom to which they are bonded, form a heterocyclyl or heteroaryl containing up to 3 hetero atoms independently selected from the group consisting of nitrogen, oxygen, and sulfur, wherein:
any such heterocyclyl optionally is substituted with one or more substituents independently selected from the group consisting of hydroxy, keto, carboxy, hydroxy-$C_1$–$C_6$-alkyl, hydroxy-$C_1$–$C_6$-alkoxy-$C_1$–$C_6$-alkyl, $C_1$–$C_6$-alkoxycarbonyl-$C_1$–$C_6$-alkyl, heterocyclyl-$C_1$–$C_6$-alkyl, $C_1$–$C_6$-alkoxycarbonyl, $C_1$–$C_6$-alkoxy-$C_1$–$C_6$-alkyl, and amino-$C_1$–$C_6$-alkyl, wherein:
the amino-$C_1$–$C_6$-alkyl nitrogen optionally is substituted with up to 2 substituents independently selected from the group consisting of $C_1$–$C_6$-alkyl;

Y is selected from the group consisting of cycloalkyl, aryl, arylmethyl, and heteroaryl, wherein:
any such substituent optionally is substituted with one or more substituents independently selected from the group consisting of halogen, halo-$C_1$–$C_6$-alkyl, and halo-$C_1$–$C_6$-alkoxy.

42. A compound or salt according to claim 40, wherein:
$R^6$ is selected from the group consisting of $C_1$–$C_6$-alkyl, $C_1$–$C_6$-alkoxy-$C_1$–$C_6$-alkyl, $C_3$–$C_6$-cycloalkyl, $C_3$–$C_8$-cycloalkyl-$C_1$–$C_6$-alkyl, $C_3$–$C_6$-alkenyl, $C_3C_6$-alkynyl, and $C_1$–$C_6$-alkylsulfonyl; and
Y is heteroaryl.

43. A method for treating a pathological condition in an animal, wherein:
the method comprises administering a compound recited in claim 1, or a pharmaceutically acceptable salt thereof, to the animal in an amount effective to treat the condition;
the condition is treatable by inhibiting matrix metalloprotease activity; and
the condition is selected from the group consisting of tissue destruction, a fibrotic disease, matrix weakening, defective injury repair, a cardiovascular disease, a pulmonary disease, a kidney disease, and a central nervous system disease.

44. A method according to claim 43, wherein the compound corresponds in structure to Formula XA:

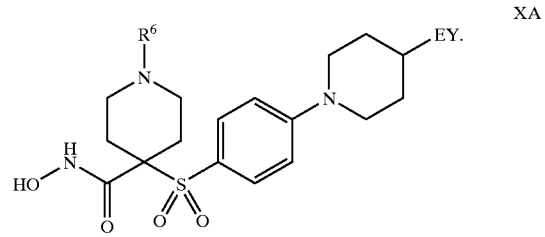

45. A method according to claim 43, wherein the condition is selected from the group consisting of osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermolysis bullosa, aortic aneurysm, weak injury repair, an adhesion, scarring, congestive heart failure, coronary thrombosis, emphysema, proteinuria, and Alzheirmer's disease.

46. A method according to claim 43, wherein the condition is selected from the group consisting of rheumatoid arthritis, osteoarthritis, septic arthritis, corneal ulceration, epidermal ulceration, gastric ulceration, tumor metastasis, tumor invasion, tumor angiogenesis, periodontal disease, proteinuria, Alzheimer's disease, coronary thrombosis, bone disease, and defective injury repair.

47. A method according to claim 45, wherein the condition is atherosclerosis.

48. A method for treating a pathological condition in an animal, wherein:

the condition is treatable by inhibiting matrix metalloprotease-2, matrix metalloprotease-9, and/or matrix metalloprotease-13 activity; and the method comprising administering a compound recited in claim 1, or a pharmaceutically-acceptable salt thereof, to the animal in an amount effective to inhibit matrix metalloprotease-2, matrix metalloprotease-9, and/or matrix metalloprotease-13.

49. A method according to claim 48, wherein the compound corresponds in structure to Formula XA:

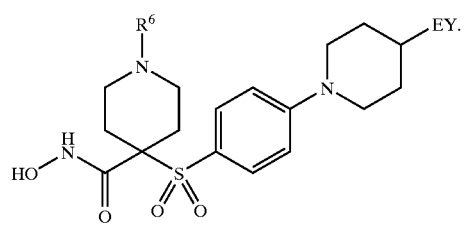

50. A method according to claim 48, wherein the compound inhibits matrix metalloprotease-13 selectively over both matrix metalloprotease-1 and matrix metalloprotease-14.

51. A method according to claim 48, wherein the compound inhibits matrix metalloprotease-9 selectively over both matrix metalloprotease-1 and matrix metalloprotease-14.

52. A method according to claim 48, wherein the compound inhibits matrix metalloprotease-9 selectively over both matrix metalloprotease-1 and matrix metalloprotease-14.

53. A method for treating a pathological condition in an animal, wherein;

the method comprises administering a compound recited in claim 1, or a pharmaceutically-acceptable salt thereof, to the animal in an amount effective to treat the condition, and the condition is treatable by inhibiting TNF-α convertase activity.

54. A method according to claim 53, wherein the compound corresponds in structure to Formula XA:

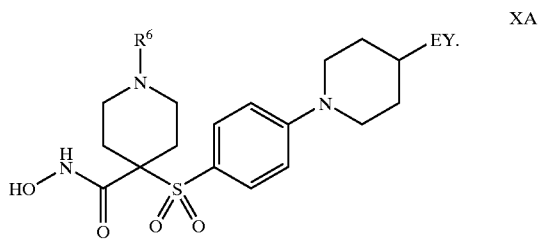

55. A method according to claim 53, wherein the condition is selected from the group consisting of inflammation, a pulmonary disease, a cardiovascular disease, an autoimmune disease, graft rejection, a fibrotic disease, cancer, an infectious disease, fever, psoriasis, hermorrage, coagulation, radiation damage, acute-phase responses of shock and sepsis, anorexia, and cachexia.

56. A method for treating a pathological condition in an animal, wherein:

the condition is treatable by inhibiting aggrecanase activity; and the method comprises administering a compound of claim 1, or a pharmaceutically-acceptable salt thereof, to the animal in an amount effective to treat the condition.

57. A method according to claim 56, wherein the compound corresponds in structure to Formula XA:

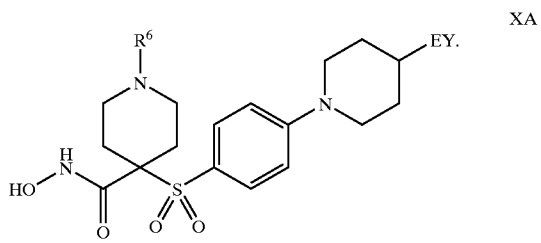

58. A method according to claim 56, wherein the condition is an inflammation condition.

59. A method according to claim 58, wherein the condition is selected from the group consisting of osteoarthritis, rheumatoid arthritis, joint injury, reactive arthritis, acute pyrophosphate arthritis, and psoriatic arthritis.

60. A method according to claim 56, wherein the condition is cancer.

61. A method for treating a pathological condition in an animal, wherein:

the method comprises administering a compound recited in claim 12, or a pharmaceutically acceptable salt thereof, to the animal in an amount effective to treat the condition;

the condition is treatable by inhibiting matrix metalloprotease activity; and the condition is selected from the group consisting of tissue destruction, a fibrotic disease, matrix weakening, defective injury repair, a cardiovascular disease, a pulmonary disease, a kidney disease, and a central nervous system disease.

62. A method according to claim 61, wherein the compound corresponds in structure to Formula XA:

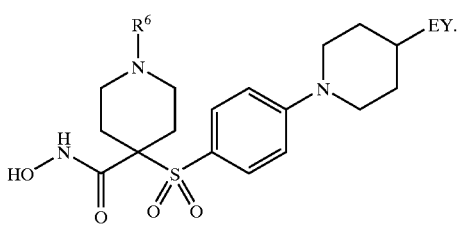
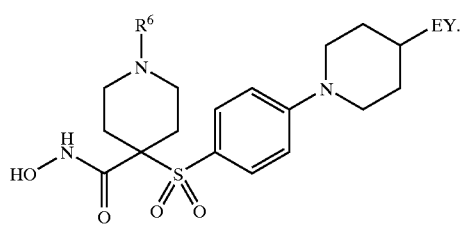

63. A method for treating a pathological condition in an animal, wherein:
   the method comprises administering a compound recited in claim 23, or a pharmaceutically acceptable salt thereof, to the animal in an amount effective to treat the condition;
   the condition is treatable by inhibiting matrix metalloprotease activity; and
   the condition is selected from the group cousisting of tissue destruction, a fibrotic disease, matrix weakening, defective injury repair, a cardiovascular disease, a pulmonary disease, a kidney disease, and a central nervous system disease.

64. A method for treating a pathological condition in an animal, wherein:
   the method comprises administering a compound recited in claim 26, or a pharmaceutically accentable salt thereof, to the animal in an amount effective to treat the condition:
   the condition is treatable by inhibiting matrix metalloprotease activity; and
   the condition is selected from the group consisting of tissue destruction, a fibrotic disease, matrix weakening, defective injury repair, a cardiovascular disease, a pulmonary disease, a kidney disease, and a central nervous system disease.

65. A method according to claim 61, wherein the condition is selected from the group consisting of osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermolysis bullosa, aortic aneurysm, weak injury repair, an adhesion, scarring, congestive heart failure, coronary thrombosis, emphysema, proteinuria, and Alzheimer's disease.

66. A method for treating a pathological condition in an animal, wherein:
   the condition is treatable by inhibiting matrix metalloprotease-2, matrix metalloprotease-9, and/or matrix metalloprotease-13; and
   the method comprising administering a compound recited in claim 12, or a pharmaceutically-acceptable salt thereof, to the animal in an amount effective to inhibit matrix metalloprotease-2, matrix metalloprotease-9, and/or matrix metalloprotease-13.

67. A method according to claim 66, wherein the compound corresponds in structure to Formula XA:

68. A method for treating a pathological condition in an animal, wherein:
   the condition is treatable by inhibiting matrix metalloprotease-2, matrix metallonrotease-9, and/or matrix metalloprotease-13, and
   the method comprising administering a compound recited in claim 23, or a pharmacentically-acceutable salt thereof, to the animal in an amount effective to inhibit matrix metalloprotease-2, matrix metallourotease-9, and/or matrix metallovrotease-13.

69. A method for treating a pathological condition in an animal, wherein:
   the condition is treatable by inhibiting matrix metalloprotease-2, matrix metalloprotease-9, and/or matrix metalloprotease-13, and
   the method comprising administering a compound recited in claim 26, or a pharmacentically-acceutable salt thereof, to the animal in an amount effective to inhibit matrix metalloprotease-2, matrix metalloprotease-9, and/or matrix metalloprotease-13.

70. A method according to claim 66, wherein the compound inhibits matrix metalloprotease-13 selectively over both matrix metalloprotease-1 and matrix metalloprotease-14.

71. A method according to claim 66, wherein the compound inhibits matrix metalloprotease-9 selectively over both matrix metalloprotease-1 and matrix metalloprotease-14.

72. A method according to claim 66, wherein the compound inhibits matrix metalloprotease-9 selectively over both matrix metalloprotease-1 and matrix metalloprotease-14.

73. A method for treating a pathological condition in an animal, wherein:
   the method comprises administering a compound recited in claim 12, or a pharmaceutically-acceptable salt thereof, to the animal in an amount effective to treat the condition, and
   the condition is treatable by inhibiting TNF-α convertase activity.

74. A method according to claim 73, wherein the compound corresponds in structure to Formula XA:

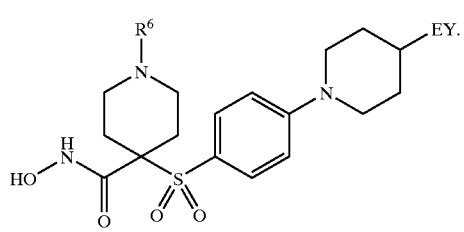

75. A method for treating a pathological condition in an animal, wherein:
the method comprises administering a compound recited in claim 23, or a pharmaceutically-acceptable salt thereof, to the animal in an amount effective to treat the condition, and
the condition is treatable by inhibiting TNF-α convertase activity.

76. A method for treating a pathological condition in an animal, wherein:
the method comprises administering a compound recited in claim 26, or a pharmaceutically-acceptable salt thereof, to the animal in an amount effective to treat the condition, and
the condition is treatable by inhibiting TNF-α convertase activity.

77. A method according to claim 73, wherein the condition is selected from the group consisting of inflammation, a pulmonary disease, a cardiovascular disease, an autoimmune disease, graft rejection, a fibrotic disease, cancer, an infectious disease, fever, psoriasis, hemorrhage, coagulation, radiation damage, acute-phase responses of shock and sepsis, anorexia, and cachexia.

78. A method for treating a pathological condition in an animal, wherein:
the condition is treatable by inhibiting aggrecanase activity; and
the method comprises administering a compound of claim 12, or a pharmaceutically-acceptable salt thereof, to the animal in an amount effective to treat the condition.

79. A method according to claim 78, wherein the compound corresponds in structure to Formula XA:

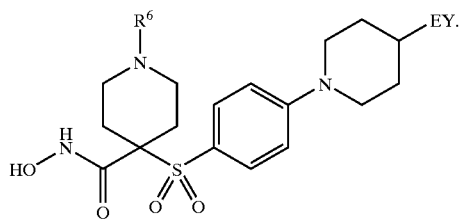

XA

80. A method for treating a pathological condition in an animal wherein:
the condition is treatable by inhibiting aggrecanase activity; and
the method comprises administering a compound of claim 23, or a pharmaceutically-acceptable salt thereof to the anunal in an amount effective to treat the condition.

81. A method for treating a pathological condition in an animal wherein:
the condition is treatable by inhibiting aggrecanase activity; and
the method comprises administering a compound of claim 26, or a pharmaceutically-acceptable salt thereof to the anunal in an amount effective to treat the condition.

82. A method according to claim 78, wherein the condition is an inflammation condition.

83. A method according to claim 82, wherein the condition is selected from the group consisting of osteoarthritis, rheumatoid arthritis, joint injury, reactive arthritis, acute pyrophosphate arthritis, and psoriatic arthritis.

84. A method according to claim 78, wherein the condition is cancer.

85. A pharmaceutical composition comprising a therapeutically effective amount of a compound recited in claim 1 or a pharmaceutically acceptable salt thereof.

86. A pharmaceutical composition according to claim 85, wherein the compound corresponds in structure to Formula XA:

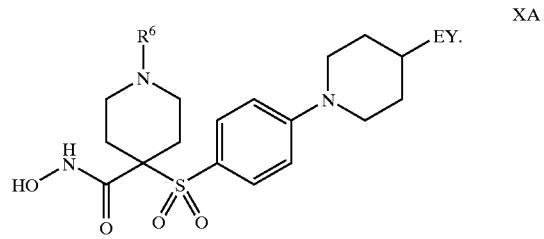

XA

87. A pharmaceutical composition comprising a therapeutically effective amount of a compound recited in claim 12 or a pharmaceutically acceptable salt thereof.

88. A pharmaceutical composition according to claim 87, wherein the compound corresponds in structure Formula XA:

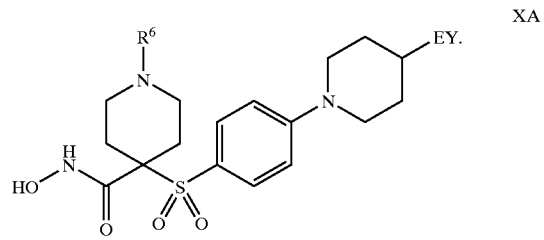

XA

89. A pharmaceutical composition comprising a therapeutically effective amount of a compound recited in claim 23 or a pharmaceutically acceptable salt thereof.

90. A pharmaceutical composition comprising a therapeutically effective amount of a compound recited in claim 26 or a pharmaceutically acceptable salt thereof.

91. A compound or a salt thereof, wherein:
the compound corresponds in structure to Formula X:

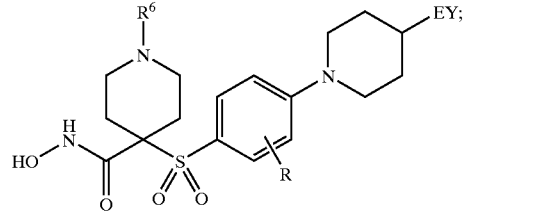

X

E is selected from the group consisting of a bond, —C(O)—, and —S—;
$R^6$ is selected from the group consisting of hydrogen, arylalkoxycarbonyl, alkylcarbonyl, alkyl, alkoxyalkyl, cycloalkyl, heteroarylcarbonyl, heteroaryl, cycloalkylalkyl, alkylsulfonyl, haloalkylcarbonyl, alkenyl, alkynyl, and $R^8R^9$-aminoalkylcarbonyl;
as to $R^8$ and $R^9$:
$R^8$ and $R^9$ are independently selected from the group consisting of hydrogen, alkyl, alkoxy, hydroxyalkyl, alkoxyalkyl, hydroxyalkoxyalkyl, hetewarylalkyl, cycloalkylalkyl, heterocyclylcarbonyl, haloalkyl, and aminoalkyl, wherein:

the aminoalkyl nitrogen optionally is substituted with up to two substituents independently selected from the group consisting of alkyl, or $R^8$ and $R^9$, together with the atom to which they are bonded, form a 5- to 8-membered heterocyclyl or heteroaryl containing up to 3 heteroatorns independently selected from the group consisting of nitrogen, oxygen, and sulfur, wherein:

any such heterocyclyl optionally is substituted with one or more substituents independently selected from the group consisting of hydroxy, keto, carboxy, alkoxyalkyl, hydroxyalkyl, hydroxyalkoxyalkyl, alkoxycaxbonylalkyl, heterocyclylalkyl, alkoxycarbonyl, and aminoalkyl, wherein:

the aminoalkyl nitrogen optionally is substituted with up to two substituents independently selected from the group consisting of alkyl; and Y is selected from the group consisting of cycloalkyl, 2,3-dihydroindolyl, heterocyclyl, aryl (other than phenyl), heteroaryl, arylalkyl, and heteroarylalkyl, wherein:

any such substituent optionally is substituted with one or more optionally substituted substituents independently selected from the group consisting of halogen, hydroxy, keto, alkyl, haloalkyl, hydroxyalkyl, alkenyl, alkoxy, alkylcarbonyl, haloalkoxy, alkylthio, alkoxyalkyl, alkoxycarbonylalkyl, cycloalkyl, cycloalkylalkyl, cycloalkyloxy, cycloalkylalkoxy, cycloalkylalkoxyalkyl, aryl, arylalkyl, arylalkoxy, heterocyclyl, heterocyclylalkyl, heteroaryl, heteroarylcarbonyl, heterocyclylcarbonylalkyl, alkylsulfonyl, amino, aminoalkyl, and aminocarbonyl, wherein:

any such substituent optionally is substituted with one or more substituents independently selected from the group consisting of halogen, nitro, alkyl, haloalkyl, alkoxy, haloalkoxy, and alkylcarbonyl, and the nitrogen of the amino, aminoalkyl, or aminocarbonyl optionally is substituted with up to two substituents independently selected from the group consisting of alkyl and cycloalkylalkyl; and R is selected from the group consisting of hydrogen and halogen.

92. A compound or salt according to claim 91, wherein Y is selected from the group consisting of cycloalkyl, 2,3-dihydroindolyl, heterocyclyl (other than piperazinyl), aryl (other than phenyl), heteroaryl, arylalkyl, and heteroarylallryl, wherein:

any such substituent optionally is substituted with one or more optionally substituted substituents independently selected from the group consisting of halogen, hydroxy, keto, alkyl, haloalkyl, hydroxyalkyl, alkenyl, alkoxy, alkylcarbonyl, haloalkoxy, alkylthio, alkoxyalkyl, alkoxycarbonylalkyl, cycloalkyl, cycloalkylalkyl, cycloalkyloxy, cycloalkylalkoxy, cycloalkylalkoxyalkyl, aryl, arylalkyl, arylallkoxy, heterocyclyl, heterocyclylalkyl, heteroaryl, heteroarylcarbonyl, heterocyclylcarbonylalkyl, alkylsulfonyl, amino, aminoalkyl, and aminocarbonyl, wherein:

any such substituent optionally is substituted with one or more substituents independently selected from the group consisting of halogen, nitro, alkyl, haloalkyl, alkoxy, haloalkoxy, and alkylcarbonyl, and the nitrogen of the amino, aminoalkyl, or aminocarbonyl optionally is substituted with up to two substituents independently selected from the group consisting of alkyl and cycloalkylalkyl.

93. A compound or a salt thereof, wherein:

the compound corresponds in structuxe to Formula X:

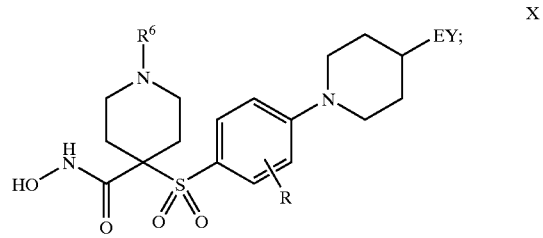

E is selected from the group consisting of a bond, —C(O)—, and —S—;

$R^6$ is selected from the group consisting of hydrogen, arylalkoxycarbonyl, alkylcarbonyl, alkyl, alkoxyalkyl, cycloalkyl, heteroarylcarbonyl, heteroaryl, cycloalkylalkyl, alkylsulfonyl, haloalkylcarbonyl, alkenyl, alkynyl, and $R^8R^9$-aminoalkylcarbonyl;

as to $R^8$ and $R^9$:

$R^8$ and $R^9$ are independently selected from the group consisting of hydrogen, alkyl, alkoxy, hydroxyalkyl, alkoxyalkyl, hydroxyalkoxyalkyl, heteroarylalkyl, cycloalkylalkyl, heterocyclylcarbonyl, haloalkyl, and aminoalkyl, wherein:

the aminoalkyl nitrogen optionally is substituted with up to two substituents independently selected from the group consisting of alkyl, or $R^8$ and $R^9$, together with the atom to which they are bonded, form a 5- to 8-membered heterocyclyl or heteroaryl containing up to 3 heteroasoms independently selected from the group consisting of nitrogen, oxygen, and sulfur, wherein:

any such heterocyclyl optionally is substituted with one or more substituents independently selected from the group consisting of hydroxy, keto, carboxy, alkoxyalkyl, hydroxyalkyl, hydroxyalkoxyalkyl, alkoxycarbonylalkyl, heterocyclylalkyl, alkoxycarbonyl, and aminoalkyl, wherein:

the aminoalkyl nitrogen optionally is substituted with up to two substituents independently selected from the group consisting of alkyl; and Y is selected from the group consisting of cycloalkyl, 2,3-dihydroindolyl, heterocyclyl (other than piperazinyl), aryl, heteroaryl, arylalkyl, and heteroarylalkyl, wherein:

any such substituent optionally is substituted with one or more optionally substituted substituents independently selected from the group consisting of halogen, hydroxy, keto, alkyl, haloalkyl, hydroxyalkyl, alkenyl, alkoxy, alkylcarbonyl, haloalkoxy, alkylthio, alkoxyalkyl, alkoxycarbonylalkyl, cycloalkyl, cycloalkylalkyl, cycloalkyloxy, cycloalkylalkoxy, cycloalkylalkoxyalkyl, aryl, arylalkyl, arylalkoxy, heterocyclyl, heterocyclylalkyl, heteroaryl, heteroarylcarbonyl, heterocyclylcarbonylancyl, alkylsulfonyl, amino, aminoalkyl, and aminocarbonyl, wherein:

any such substituent optionally is substituted with one or more substituents independently selected from the group consisting of halogen, nitro, alkyl, haloalkyl, alkoxy, haloalkoxy, and alkylcarbonyl, and the nitrogen of the amino, aminoalkyl, or aminocarbonyl optionally is substituted with up to two substituents independently selected from the group consisting of alkyl and cycloalkylalkyl; and R is selected from the group consisting of hydrogen and halogen.

* * * * *